US009632013B2

(12) United States Patent
Rivas et al.

(10) Patent No.: US 9,632,013 B2
(45) Date of Patent: Apr. 25, 2017

(54) FLUID INJECTION AND SAFETY SYSTEM

(75) Inventors: Gil Rivas, Danville, CA (US); Michael Butler, Dublin, CA (US); Jeffrey T. Chiou, Union City, CA (US); Eugene Lim, Lafayette, CA (US)

(73) Assignee: Optiscan Biomedical Corporation, Hayward, CA (US)

( * ) Notice: Subject to any disclaimer, the term of this patent is extended or adjusted under 35 U.S.C. 154(b) by 472 days.

(21) Appl. No.: 13/619,432

(22) Filed: Sep. 14, 2012

(65) Prior Publication Data

US 2013/0160532 A1 Jun. 27, 2013

Related U.S. Application Data

(63) Continuation of application No. 12/123,422, filed on May 19, 2008, now Pat. No. 8,470,241.

(60) Provisional application No. 60/939,023, filed on May 18, 2007, provisional application No. 60/979,374, filed on Oct. 11, 2007.

(51) Int. Cl.
| | | |
|---|---|---|
| A61B 5/00 | (2006.01) | |
| A61B 5/153 | (2006.01) | |
| G01N 1/10 | (2006.01) | |
| G06F 19/10 | (2011.01) | |
| A61B 5/145 | (2006.01) | |
| A61B 5/1455 | (2006.01) | |
| A61M 39/02 | (2006.01) | |
| A61M 39/10 | (2006.01) | |
| A61B 5/15 | (2006.01) | |
| A61B 5/157 | (2006.01) | |
| A61M 5/14 | (2006.01) | |
| A61M 5/172 | (2006.01) | |

(52) U.S. Cl.
CPC ............ *G01N 1/10* (2013.01); *A61B 5/1455* (2013.01); *A61B 5/14532* (2013.01); *A61B 5/14546* (2013.01); *A61B 5/153* (2013.01); *A61B 5/15003* (2013.01); *A61B 5/157* (2013.01); *A61B 5/150221* (2013.01); *A61B 5/150229* (2013.01); *A61B 5/150236* (2013.01); *A61B 5/150244* (2013.01); *A61B 5/150267* (2013.01); *A61B 5/150305* (2013.01); *A61B 5/150755* (2013.01); *A61B 5/150824* (2013.01); *A61B 5/150854* (2013.01); *A61M 39/02* (2013.01); *A61M 39/10* (2013.01); *G06F 19/10* (2013.01); *A61B 5/14557* (2013.01); *A61B 5/150786* (2013.01); *A61M 5/1415* (2013.01); *A61M 5/1723* (2013.01); *A61M 2039/1077* (2013.01); *A61M 2039/1094* (2013.01); *A61M 2230/201* (2013.01); *Y10T 436/11* (2015.01); *Y10T 436/144444* (2015.01)

(58) Field of Classification Search
None
See application file for complete search history.

(56) References Cited

U.S. PATENT DOCUMENTS

| | | |
|---|---|---|
| 2,797,149 A | 6/1957 | Skeggs |
| 3,251,229 A | 5/1966 | Isreeli et al. |
| 3,252,327 A | 5/1966 | Ferrrari |
| 3,266,322 A | 8/1966 | Negersmith et al. |
| 3,282,651 A | 11/1966 | Ferrari et al. |
| 3,352,303 A | 11/1967 | Delaney |
| 3,562,234 A | 2/1971 | Resz et al. |
| 3,565,062 A | 2/1971 | Kuris |
| 3,634,039 A | 1/1972 | Brondy |
| 3,910,256 A | 10/1975 | Clark et al. |
| 3,972,614 A | 8/1976 | Johansen et al. |
| 4,127,111 A | 11/1978 | Drolet |
| 4,151,845 A | 5/1979 | Clemens |
| 4,240,438 A | 12/1980 | Updike et al. |
| 4,245,634 A | 1/1981 | Albisser et al. |
| 4,370,983 A | 2/1983 | Lichtenstein |
| 4,519,792 A | 5/1985 | Dawe |
| 4,526,568 A | 7/1985 | Clemens et al. |
| 4,526,569 A | 7/1985 | Bernardi |

(Continued)

FOREIGN PATENT DOCUMENTS

| | | |
|---|---|---|
| EP | 0549341 | 12/1992 |
| JP | 01-170031 | 6/2001 |

(Continued)

OTHER PUBLICATIONS

Berger et al., "An Enhanced Algorithm for Linear Multivariate"; Analytical Chemistry, vol. 70, No. 3, pp. 623-627, Feb. 1, 1998.

(Continued)

*Primary Examiner* — Karen Canella

(74) *Attorney, Agent, or Firm* — Knobbe Martens Olson & Bear LLP

(57) ABSTRACT

Various medical systems and methods are described, including a medical monitoring system. The medical monitoring system can have a fluid system configured to receive bodily fluid and optically analyze said fluid to determine analyte concentration. The fluid system can have a removable portion. The removable portion can have an opening with a port. The system can also have a container configured to contain anticoagulant. The container can have a portion configured to mate with the port of the removable portion. The container can be further configured to not fit into a conventional luer fitting. An anti-coagulant insertion apparatus is also described. The apparatus can have a syringe, a dock with a port, and an adapter configured to connect the syringe to the port. The dock can also have a tab configured to move with the port.

13 Claims, 57 Drawing Sheets

(56) References Cited

U.S. PATENT DOCUMENTS

| | | |
|---|---|---|
| 4,535,786 A | 8/1985 | Kater |
| 4,537,561 A | 8/1985 | Xanthopoulos |
| 4,568,545 A | 2/1986 | Mihara et al. |
| 4,573,968 A | 3/1986 | Parker |
| 4,613,322 A | 9/1986 | Edelson |
| 4,657,027 A | 4/1987 | Paulsen |
| 4,657,529 A | 4/1987 | Prince et al. |
| 4,784,157 A | 11/1988 | Halls et al. |
| 4,786,394 A | 11/1988 | Enzer et al. |
| 4,796,644 A | 1/1989 | Polaschegg |
| 4,818,190 A | 4/1989 | Pelmulder et al. |
| 4,850,980 A | 7/1989 | Lentz et al. |
| 4,870,953 A | 10/1989 | DonMicheall et al. |
| 4,883,483 A | 11/1989 | Lindmayer |
| 4,919,596 A | 4/1990 | Slate et al. |
| 4,934,369 A | 6/1990 | Maxwell |
| 4,940,527 A | 7/1990 | Kazlauskas |
| 4,974,592 A | 12/1990 | Branco et al. |
| 4,976,270 A | 12/1990 | Parl et al. |
| 5,097,834 A | 3/1992 | Skrabal |
| 5,109,850 A | 5/1992 | Blanco et al. |
| 5,134,079 A | 7/1992 | Cusack et al. |
| 5,149,501 A | 9/1992 | Babson et al. |
| 5,165,406 A | 11/1992 | Wong |
| 5,269,291 A | 12/1993 | Carter |
| 5,279,576 A | 1/1994 | Loo et al. |
| 5,295,484 A | 3/1994 | Marcus et al. |
| 5,300,779 A | 4/1994 | Hillman et al. |
| 5,307,816 A | 5/1994 | Hashimoto et al. |
| 5,316,730 A | 5/1994 | Blake |
| 5,335,658 A | 8/1994 | Bedingham |
| 5,377,674 A | 1/1995 | Kuestner |
| 5,380,665 A | 1/1995 | Cusack et al. |
| 5,399,158 A | 3/1995 | Lauer et al. |
| 5,421,328 A | 6/1995 | Bedingham |
| 5,431,663 A | 7/1995 | Carter |
| 5,437,635 A | 8/1995 | Fields et al. |
| 5,454,409 A | 10/1995 | McAffer et al. |
| 5,505,828 A | 4/1996 | Wong et al. |
| 5,524,620 A | 6/1996 | Rosenschein |
| 5,609,572 A | 3/1997 | Lang |
| 5,620,409 A | 4/1997 | Venuto et al. |
| 5,685,845 A | 11/1997 | Grimard |
| 5,695,460 A | 12/1997 | Siegel et al. |
| 5,697,366 A | 12/1997 | Kimball et al. |
| 5,697,899 A | 12/1997 | Hillman et al. |
| 5,722,397 A | 3/1998 | Eppstein |
| 5,758,643 A | 6/1998 | Wong et al. |
| 5,769,138 A | 6/1998 | Sadowski et al. |
| 5,772,652 A | 6/1998 | Zielinski |
| 5,773,832 A * | 6/1998 | Sayed et al. ............ 250/370.09 |
| 5,817,007 A | 10/1998 | Fodgaard et al. |
| 5,817,082 A | 10/1998 | Niedospial, Jr. et al. |
| 5,827,746 A | 10/1998 | Duic |
| 5,891,129 A | 4/1999 | Daubert et al. |
| 5,893,397 A | 4/1999 | Peterson et al. |
| 5,902,253 A | 5/1999 | Pfeiffer et al. |
| 5,944,660 A | 8/1999 | Kimball et al. |
| 5,947,911 A | 9/1999 | Wong et al. |
| 6,007,499 A | 12/1999 | Martin et al. |
| 6,017,318 A | 1/2000 | Gauthier |
| 6,025,597 A | 2/2000 | Sterling et al. |
| 6,040,578 A | 3/2000 | Malin |
| 6,077,055 A | 6/2000 | Vilks |
| 6,086,573 A | 7/2000 | Siegel et al. |
| 6,090,093 A | 7/2000 | Thibault et al. |
| 6,101,406 A | 8/2000 | Hacker et al. |
| 6,107,280 A | 8/2000 | White et al. |
| 6,113,570 A | 9/2000 | Siegel et al. |
| 6,117,290 A | 9/2000 | Say et al. |
| 6,200,287 B1 | 3/2001 | Keller et al. |
| 6,258,078 B1 | 7/2001 | Thilly |
| 6,261,065 B1 | 7/2001 | Nayak et al. |
| 6,261,519 B1 | 7/2001 | Harding et al. |
| 6,262,798 B1 | 7/2001 | Shepherd et al. |
| 6,358,534 B1 | 3/2002 | Schwarz et al. |
| 6,433,464 B2 | 8/2002 | Jones |
| 6,461,586 B1 | 10/2002 | Unger |
| 6,478,765 B2 | 11/2002 | Siegel et al. |
| 6,478,788 B1 | 11/2002 | Aneas |
| 6,491,656 B1 | 12/2002 | Morris |
| 6,521,182 B1 | 2/2003 | Shartle et al. |
| 6,614,873 B1 * | 9/2003 | Taylor et al. ............ 378/62 |
| 6,652,136 B2 | 11/2003 | Marziali |
| 6,652,509 B1 | 11/2003 | Helgren et al. |
| 6,656,433 B2 | 12/2003 | Sasso |
| 6,685,657 B2 | 2/2004 | Jones |
| 6,715,520 B2 | 4/2004 | Andreasson et al. |
| 6,716,412 B2 | 4/2004 | Unger |
| 6,733,450 B1 | 5/2004 | Alexandrov et al. |
| 6,890,291 B2 | 5/2005 | Robinson et al. |
| 6,958,809 B2 | 10/2005 | Sterling |
| RE38,869 E | 11/2005 | Polaschegg et al. |
| 6,989,891 B2 | 1/2006 | Braig |
| 7,061,593 B2 | 6/2006 | Braig |
| 7,115,205 B2 | 10/2006 | Robinson et al. |
| 7,126,676 B2 | 10/2006 | Greco |
| 7,220,226 B2 | 5/2007 | Rovegno |
| 7,241,285 B1 | 7/2007 | Dikeman |
| 7,364,562 B2 | 4/2008 | Braig et al. |
| 7,479,123 B2 | 1/2009 | Briggs |
| 7,479,131 B2 | 1/2009 | Mathias et al. |
| 8,034,015 B2 | 10/2011 | Braig et al. |
| 8,470,241 B2 | 6/2013 | Rivas et al. |
| 2002/0045525 A1 | 4/2002 | Marziali |
| 2002/0076354 A1 | 6/2002 | Cohen |
| 2002/0098528 A1 | 7/2002 | Gordon et al. |
| 2002/0198528 A1 | 12/2002 | Engh et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0153895 A1 | 8/2003 | Leinsing |
| 2003/0178569 A1 | 9/2003 | Sterling et al. |
| 2003/0199803 A1 | 10/2003 | Robinson et al. |
| 2004/0019431 A1 | 1/2004 | Sterling et al. |
| 2004/0044327 A1 | 3/2004 | Hasegawa |
| 2004/0082899 A1 | 4/2004 | Mathias et al. |
| 2004/0127841 A1 | 7/2004 | Briggs |
| 2004/0147034 A1 | 7/2004 | Gore et al. |
| 2004/0236305 A1 | 11/2004 | Jansen et al. |
| 2004/0241736 A1 | 12/2004 | Hendee et al. |
| 2004/0249308 A1 | 12/2004 | Forssell |
| 2005/0036147 A1 | 2/2005 | Sterling et al. |
| 2005/0038357 A1 | 2/2005 | Hartstein et al. |
| 2005/0203360 A1 | 9/2005 | Brauker et al. |
| 2005/0284815 A1 | 12/2005 | Sparks et al. |
| 2006/0009727 A1 | 1/2006 | O'Mahony et al. |
| 2006/0029923 A1 | 2/2006 | Togawa et al. |
| 2006/0079809 A1 | 4/2006 | Goldberger et al. |
| 2006/0089594 A1 | 4/2006 | Landau |
| 2006/0166276 A1 | 7/2006 | Doyle et al. |
| 2006/0189925 A1 | 8/2006 | Gable et al. |
| 2006/0189926 A1 | 8/2006 | Hall et al. |
| 2006/0200070 A1 | 9/2006 | Callicoat et al. |
| 2006/0229531 A1 | 10/2006 | Goldberger et al. |
| 2007/0060872 A1 | 3/2007 | Hall et al. |
| 2007/0060904 A1 | 3/2007 | Vedrine et al. |
| 2007/0104616 A1 | 5/2007 | Keenan et al. |
| 2007/0142720 A1 | 6/2007 | Ridder et al. |
| 2007/0167904 A1 | 7/2007 | Zinger et al. |
| 2007/0173783 A1 | 7/2007 | Haindl |
| 2007/0225675 A1 | 9/2007 | Robinson et al. |
| 2007/0239096 A1 | 10/2007 | Keenan et al. |
| 2010/0273738 A1 | 10/2010 | Valcke et al. |

FOREIGN PATENT DOCUMENTS

| | | |
|---|---|---|
| WO | WO 02/38201 | 5/2002 |
| WO | WO 02/43866 | 6/2002 |
| WO | WO 03/016882 | 2/2003 |
| WO | WO 03/039362 | 5/2003 |
| WO | WO 2004/086971 | 10/2004 |
| WO | WO 2004/092715 A1 | 10/2004 |

(56) References Cited

FOREIGN PATENT DOCUMENTS

| WO | WO 2005/005044 | 1/2005 |
|---|---|---|
| WO | WO 2005/110601 A1 | 11/2005 |
| WO | WO 2006/039310 | 4/2006 |

OTHER PUBLICATIONS

Billman et. al., "Clinical Performance of an In line Ex-Vivo Point of Care Monitor: A Multicenter Study," Clinical Chemistry 48:11, pp. 2030-2043, 2002.
Finkleman et al., "Agreement Between Bedside Blood and Plasma Glucose Measurement in the ICU Setting"; retrieved from http://www.chestjournal.org; CHEST/127/5/May 2005.
Fogt et al., "Development and Evaluation of a Glucose Analyzer for a Glucose-Controlled Insulin Infusion System (Biostator)"; Clinical Chemistry, vol. 24, No. 8, pp. 1366-1372, 1978.
Franchini, Massimo, "Heparin-induced thrombocytopenia: an update", Thrombosis Journal, Oct. 4, 2005, vol. 3, Issue 14.
Glucon Critical Care Blood Glucose Monitor; Glucon; retrieved from http://www.glucon.com.
International Search Report and Written Opinion of the ISA in International Application No. PCT/US2008/063996.
Raelene E. Maser PhD., et al.; Critical Care Medicine, vol. 22/No. 4, Apr. 1994; "Use of arterial blood with bedside glucose reflectance meters in an intensive care unit: Are they accurate?".
Ray, et al.; Critical Care Medicine, vol. 29, No. 11 (Nov. 2001) Reference Collection WI CR216K Nov. 20, 2001 07:00:41; "Pilot study of the accuracy of bedside glucometry in the intensive care unit.".
Vonach et al., "Application of Mid-Infrared Transmission Spectrometry to the Direct Determination of Glucose in Whole Blood," Applied Spectroscopy, vol. 52, No. 6, 1998, pp. 820-822.
Widness et al., "Clinical Performance on an In-Line Point-of-Care Monitor in Neonates"; Pediatrics, vol. 106, No. 3, pp. 497-504, Sep. 2000.
Written Opinion of the ISA in International Application No. PCT/US2006/039201.
Andrew J. Berger, "Measurement of Analytes in Human Serum and Whole Blood Samples by Near Infrared Raman Spectroscopy," Chapter 4, Ph. D. thesis, Massachusetts Institute of Technology, 1998,.

* cited by examiner

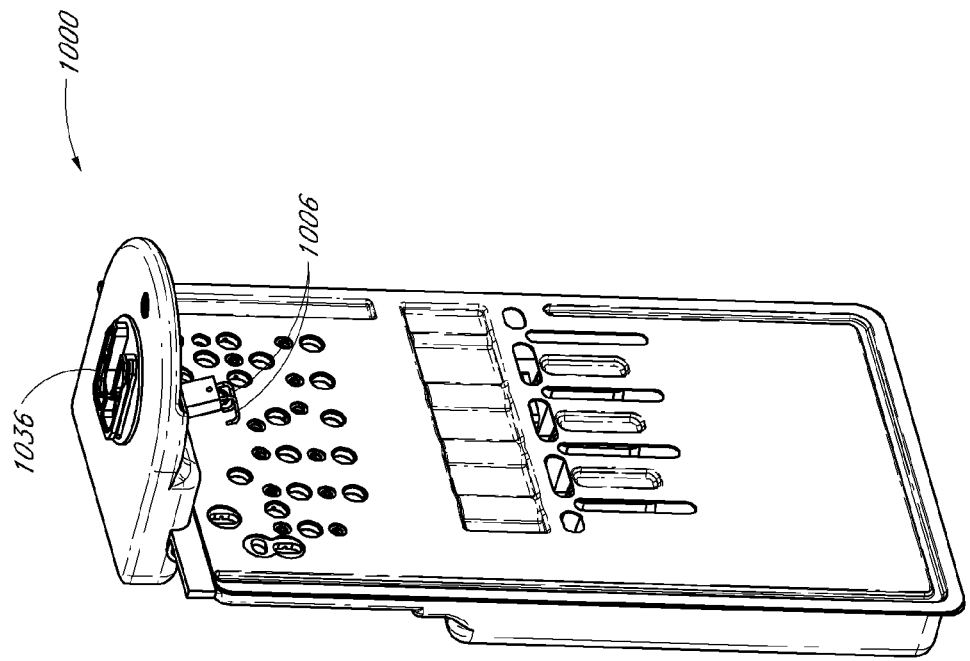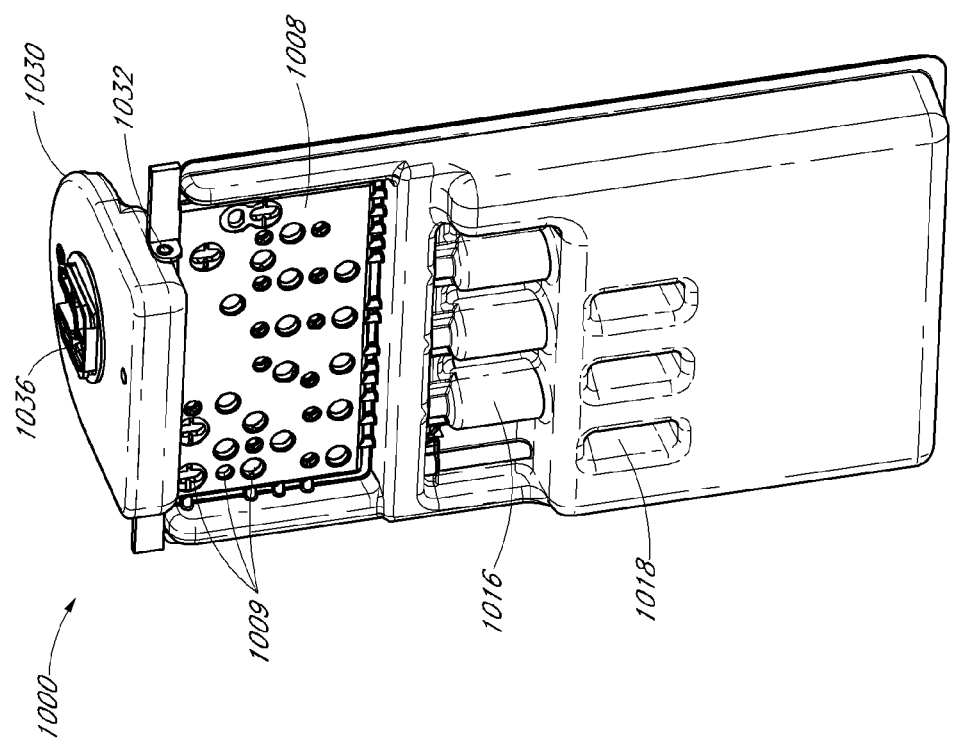
FIG. 10

FLUID INJECTION AND SAFETY SYSTEM

CROSS-REFERENCE TO RELATED APPLICATIONS

This application is a continuation of U.S. application Ser. No. 12/123,422, filed May 19, 2008, entitled "FLUID INJECTION AND SAFETY SYSTEM," which claims the benefit under 35 U.S.C. §119(e) of U.S. Provisional Patent Application No. 60/939,023, entitled "FLUID INJECTION AND SAFETY SYSTEM," filed May 18, 2007, and U.S. Provisional Patent Application No. 60/979,374, entitled "FLUID INJECTION AND SAFETY SYSTEM," filed Oct. 11, 2007. Each of the above-listed applications is hereby incorporated by reference in its entirety and made part of this specification.

BACKGROUND

Field

Some embodiments of the disclosure relate generally to methods and devices for determining a concentration of an analyte in a sample, such as an analyte in a sample of bodily fluid, as well as methods and devices which can be used to support the making of such determinations. For example, some embodiments allow anticoagulant to be injected into such a system, while minimizing associated risks.

Description of Related Art

It is advantageous to measure the levels of certain analytes, such as glucose, in a bodily fluid, such as blood). This can be done, for example, in a hospital or clinical setting when there is a risk that the levels of certain analytes may move outside a desired range, which in turn can jeopardize the health of a patient. Currently known systems for analyte monitoring in a hospital or clinical setting may suffer from various drawbacks. For example, blood can coagulate in fluid lines. Moreover, use of anticoagulants to inhibit such coagulation often involves risks.

SUMMARY

Example embodiments described herein have several features, no single one of which is solely responsible for their desirable attributes. Without limiting the scope of the claims, some of the advantageous features will now be summarized.

In some embodiments, there is provided a medical monitoring system comprising: a fluid system configured to receive bodily fluid and optically analyze said fluid to determine analyte concentration, said fluid system having a removable portion; an opening in said removable portion having a safety port; and a container configured to contain anticoagulant, the container having a portion configured to mate with said safety port, the container further configured to not accommodate a connection with a conventional luer fitting configured to improve safety by preventing a user from introducing anticoagulant into any other ports having conventional luer fittings. In some embodiments, the system can be configured to receive blood. In some embodiments, the system can be further configured to determine glucose concentration in the blood. In some embodiments, the removable portion comprises a disposable cartridge. In some embodiments, the container can be a syringe. In some embodiments, the system can comprise an adapter configured to connect to the container. In some embodiments, the system can further comprise an anticoagulant holder, and the adapter can be further configured to connect the container to the anticoagulant holder. In some embodiments, the anticoagulant holder can be a vial. In some embodiments, the container can be a disposable syringe body. In some embodiments, the removable portion can have an opening sized to receive the container. In some embodiments, the port can comprise a dock. In some embodiments, the dock and container can be configured to connect securely. In some embodiments, the dock can further comprise a tab having a first position and a second position, and the tab can further be configured to prevent the removable portion from inserting into the medical monitoring system when the tab is in the first position. In some embodiments, the tab can be configured to be in the second position when the container is in a receptacle in the removable portion.

In some embodiments, there is provided an anti-coagulant insertion apparatus comprising: a syringe configured to hold medical fluid, the syringe having a tip; a dock having a movable port configured to receive the tip of the syringe, the syringe and port configured to move together from a primary position to a secondary position; and a tab on the dock configured to move with a portion of the port as the syringe is moved, the tab preventing insertion of the dock into a medical device unless the syringe is in the secondary position. In some embodiments, the syringe can have a collar and the dock can have a groove, and the collar can be configured to fit into the groove. In some embodiments, the dock can be configured not to allow the syringe to move the port unless the collar fits into the groove, securing the syringe to the dock. In some embodiments, the movable port can be rotatable.

In some embodiments, there is provided a method of introducing fluid into a removable portion of a medical device. The method can comprise: providing an adapter on a syringe; providing a fluid container; attaching the adapter to the container; withdrawing fluid from the container into the syringe; separating the syringe from the adapter and exposing an end of the adapter having a special shape that prevents connection to a conventional luer fitting; allowing the adapter to remain connected to the container to prevent use of container contents except through an implement having the shape of the adapter; inserting a portion of the syringe into a corresponding portion of a removable portion of a medical device; and expelling fluid from the syringe into the removable portion of the medical device. In some embodiments, providing a fluid container can comprise providing a Heparin vial. In some embodiments, providing an adapter on a syringe can further comprise providing a sterilized adapter-syringe combination. In some embodiments, inserting a portion of the syringe into a corresponding portion of a removable portion of a medical device can comprise docking the syringe with a dock in a disposable cartridge. In some embodiments, the method can further comprise securing the syringe to the removeable portion of the medical device before expelling fluid from the syringe into the removable portion of the medical device.

In some embodiments, there is provided an anti-coagulant insertion apparatus comprising: a syringe; and an adapter configured to connect to the syringe, wherein the adapter comprises one or more tabs that are configured to engage a portion of the anti-coagulant holder, the tabs further configured to deter disconnection of the anti-coagulant holder from the adapter. In some embodiments, the tabs are configured to resiliently deform as the adapter is connected to the syringe. In some embodiments, the anti-coagulant container is a heparin vial. In some embodiments, the syringe is specifically configured to not fit into a conventional luer fitting. In some embodiments, the tabs are further configured to require more force to disconnect the anti-coagulant holder from the adapter than was required to connect the anti-coagulant holder to the adapter. In some embodiments, the tabs are further configured to require a large force to disconnect the anti-coagulant holder from the adapter. In some embodiments, the tabs are further configured to require a tool or machinery to disconnect the anti-coagulant holder from the adapter. In some embodiments, the tabs are further configured to require breaking the adapter or breaking the anti-coagulant holder to disconnect the anti-coagulant holder from the adapter. In some embodiments, the tabs are further configured to resiliently engage the anti-coagulant holder such that without being forced outward, the tabs will not allow removal of the anti-coagulant holder from the adapter without sufficient force being applied to break the tabs. In some embodiments, the adapter is configured such that when the adapter is connected to the anti-coagulant holder, conventional medical tools cannot connect to the adapter to access fluid in the anti-coagulant holder.

In some embodiments, there is provided a method of introducing fluid into a removable portion of a medical device. The method can comprise: providing an adapter on a syringe; providing a fluid container; attaching the adapter to the container; withdrawing fluid from the container into the syringe; separating the syringe from the adapter and exposing an end of the adapter having a special shape that prevents connection to a conventional luer fitting; allowing the adapter to remain connected to the container to prevent use of container contents except through an implement having the shape of the adapter; inserting a portion of the syringe into a corresponding portion of a removable portion of a medical device; and expelling fluid from the syringe into the removable portion of the medical device. In some embodiments, providing a fluid container can comprise providing a Heparin vial. In some embodiments, providing an adapter on a syringe can further comprise providing a sterilized adapter-syringe combination. In some embodiments, inserting a portion of the syringe into a corresponding portion of a removable portion of a medical device can comprise docking the syringe with a dock in a disposable cartridge. In some embodiments, the method can further comprise securing the syringe to the removeable portion of the medical device before expelling fluid from the syringe into the removable portion of the medical device.

In some embodiments, there is provided a method of safely using a medical fluid in an analyte monitoring system and preventing use of the medical fluid for extraneous purposes, the method comprising the steps of: providing a medical fluid container; transferring fluid from the medical fluid container to an intermediate fluid transfer container; inserting the intermediate fluid transfer container into a port in an analyte monitoring system; preventing the intermediate fluid transfer container from connecting with other medical ports by providing a special portion of the intermediate fluid transfer container that deters connection to other medical ports, thereby encouraging the discarding of the intermediate fluid transfer container; and preventing the medical fluid container from connecting with other medical ports by providing a special end that deters connection to other medical ports, thereby encouraging the discarding of the medical fluid container. In some embodiments, the medical fluid container is a heparin vial. In some embodiments, the intermediate fluid transfer container is a disposable syringe. In some embodiments, the special portion of the intermediate fluid transfer container is an end having a special shape that deters connection to other medical ports.

In some embodiments, there is provided a medical device and automated setup instruction system. The system can comprise, for example: a display configured to be visible to a medical device user when the user is preparing the medical device for use in a medical setting; a computer memory configured to store setup information and protocols that are specific to the medical device; and an input module configured to receive input relating to device setup. The input module can comprise, for example: one or more sensors configured to detect a status of the medical device; one or more direct user input portions configured to accept input from the user relating to user-participation aspects of the device setup protocols; an automatic in-service medical device setup controller configured to access the computer memory according to the stored protocols and provide, on the display, sequential instructions to the medical device user, wherein the setup controller determines based on input received from the input module to display a portion of the setup information stored on the computer memory.

BRIEF DESCRIPTION OF THE DRAWINGS

The following drawings and the associated descriptions are provided to illustrate embodiments of the present disclosure and do not limit the scope of the claims.

FIG. 10 illustrates an embodiment of a removable cartridge that can interface with a monitoring device.

Figure 1:
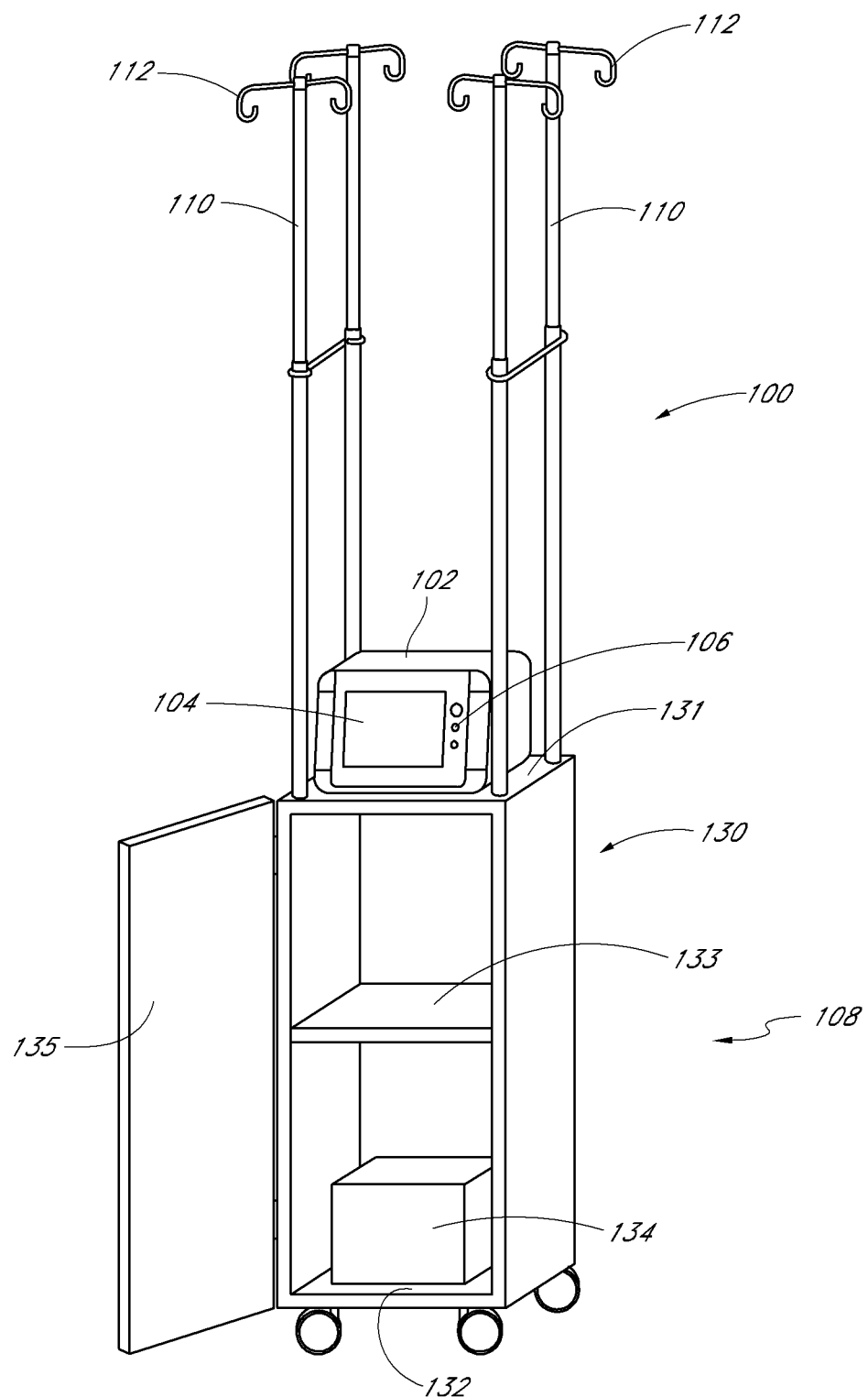
FIG. 1 shows an embodiment of an apparatus for withdrawing and analyzing fluid samples.

These and other features will now be described with reference to the drawings summarized above. The drawings and the associated descriptions are provided to illustrate embodiments and not to limit the scope of any claim. Throughout the drawings, reference numbers may be reused to indicate correspondence between referenced elements. In addition, where applicable, the first one or two digits of a reference numeral for an element generally indicate the figure number in which the element first appears.

DETAILED DESCRIPTION OF PREFERRED EMBODIMENTS

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The systems and methods discussed herein can be used anywhere, including, for example, in laboratories, hospitals, healthcare facilities, intensive care units (ICUs), or residences. Moreover, the systems and methods discussed herein can be used for invasive techniques, as well as non-invasive techniques or techniques that do not involve a body or a patient such as, for example, in vitro techniques.

Analyte Monitoring Apparatus

FIG. 1 shows an embodiment of an apparatus 100 for withdrawing and analyzing fluid samples. The apparatus 100 includes a monitoring device 102. In some embodiments, the monitoring device 102 can be an "OptiScanner®" monitor available from OptiScan Biomedical Corporation of Hayward, Calif. In some embodiments, the device 102 can measure one or more physiological parameters, such as the concentration of one or more substance(s) in a sample fluid. The sample fluid can be, for example, whole blood from a patient 302 (see, e.g., FIG. 3) and/or a component of whole blood such as, e.g., blood plasma. In some embodiments, the device 100 can also deliver an infusion fluid to a patient.

In the illustrated embodiment, the monitoring device 102 includes a display 104 such as, for example, a touch-sensitive liquid crystal display. The display 104 can provide an interface that includes alerts, indicators, charts, and/or soft buttons. The device 102 also can include one or more inputs and/or outputs 106 that provide connectivity and/or permit user interactivity.

In the embodiment shown in FIG. 1, the device 102 is mounted on a stand 108. The stand 108 may comprise a cart such as, for example, a wheeled cart 130 as shown in FIG. 1. In some embodiments, the stand 108 is configured to roll on a wheeled pedestal 240 (shown in FIG. 2). The stand 108 advantageously can be easily moved and includes one or more poles 110 and/or hooks 112. The poles 110 and hooks 112 can be configured to accommodate other medical devices and/or implements, including, for example, infusion pumps, saline bags, arterial pressure sensors, other monitors and medical devices, and so forth. Some stands or carts may become unstable if intravenous (IV) bags, IV pumps, and other medical devices are hung too high on the stand or cart. In some embodiments, the apparatus 100 can be configured to have a low center of gravity, which may overcome possible instability. For example, the stand 108 can be weighted at the bottom to at least partially offset the weight of IV bags, IV pumps and medical devices that may be attached to the hooks 112 that are placed above the monitoring device 102. Adding weight toward the bottom (e.g., near the wheels) may help prevent the apparatus 100 from tipping over.

In some embodiments, the apparatus 100 includes the cart 130, which has an upper shelf 131 on which the monitoring device 102 may be placed (or attached) and a bottom shelf 132 on which a battery 134 may be placed (or attached). The battery 134 may be used as a main or backup power supply for the monitoring device 102 (which may additionally or alternatively accept electrical power from a wall socket). Two or more batteries are used in certain embodiments. The apparatus 100 may be configured so that the upper and lower shelves 131, 132 are close to ground level, and the battery provides counterweight. Other types of counterweights may be used. For example, in some embodiments, portions of the cart 130 near the floor (e.g., a lower shelf) are weighted, formed from a substantial quantity of material (e.g., thick sheets of metal), and/or formed from a relatively high-density metal (e.g., lead). In some embodiments the bottom shelf 132 is approximately 6 inches to 1 foot above ground level, and the upper shelf 131 is approximately 2 feet to 4 feet above ground level. In some embodiments the upper shelf 131 may be configured to support approximately 40 pounds (lbs), and the bottom shelf 132 may be configured to support approximately 20 lbs. One possible advantage of embodiments having such a configuration is that IV pumps, bags containing saline, blood and/or drugs, and other medical equipment weighing approximately 60 lbs, collectively, can be hung on the hooks 112 above the shelves without making the apparatus 100 unstable. The apparatus 100 may be moved by applying a horizontal force on the apparatus 100, for example, by pushing and/or pulling the poles 110. In many cases, a user may exert force on an upper portion of the apparatus 100, for example, close to shoulder-height. By counterbalancing the weight as described above, the apparatus 100 may be moved in a reasonably stable manner.

In the illustrated embodiment, the cart 130 includes the bottom shelf 132 and an intermediate shelf 133, which are enclosed on three sides by walls and on a fourth side by a door 135. The door 135 can be opened (as shown in FIG. 1) to provide access to the shelves 132, 133. In other embodiments, the fourth side is not enclosed (e.g., the door 135 is not used). Many cart variations are possible. In some embodiments the battery 134 can be placed on the bottom shelf 134 or the intermediate shelf 133.

Figure 2:
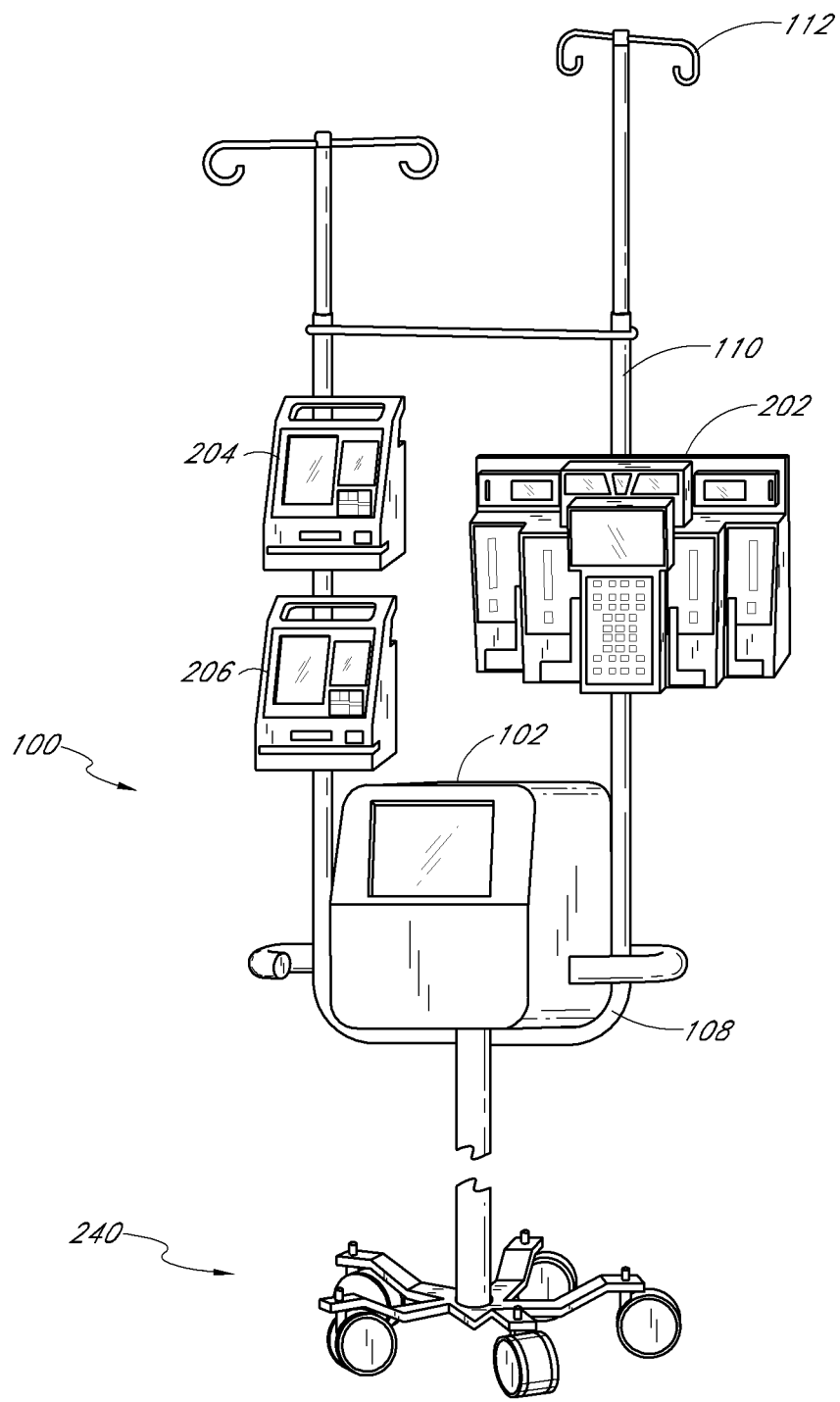
FIG. 2 illustrates how various other devices can be supported on or near an embodiment of apparatus illustrated in FIG. 1.

FIG. 2 illustrates how various other devices can be supported on or near the apparatus 100 illustrated in FIG. 1. For example, the poles 110 of the stand 108 can be configured (e.g., of sufficient size and strength) to accommodate multiple devices 202, 204, 206. In some embodiments, one or more COLLEAGUE® volumetric infusion pumps available from Baxter International Inc. of Deerfield, Ill. can be accommodated. In some embodiments, one or more Alaris® PC units available from Cardinal Health, Inc. of Dublin, Ohio can be accommodated. Furthermore, various other medical devices (including the two examples mentioned here), can be integrated with the disclosed monitoring device 102 such that multiple devices function in concert for the benefit of one or multiple patients without the devices interfering with each other.

Figure 3:
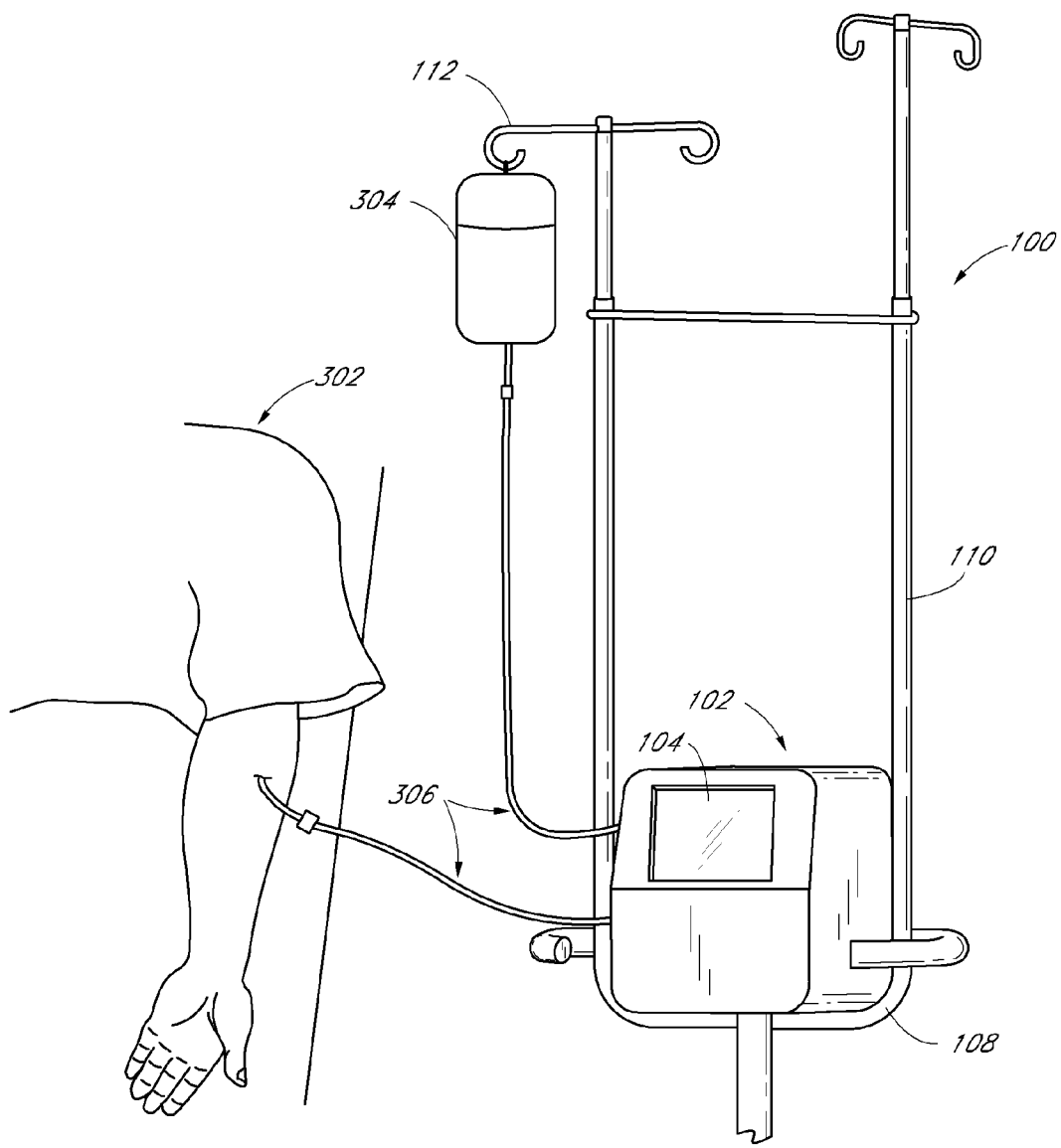
FIG. 3 illustrates an embodiment of the apparatus in FIG. 1 configured to be connected to a patient.
Figure 3A:
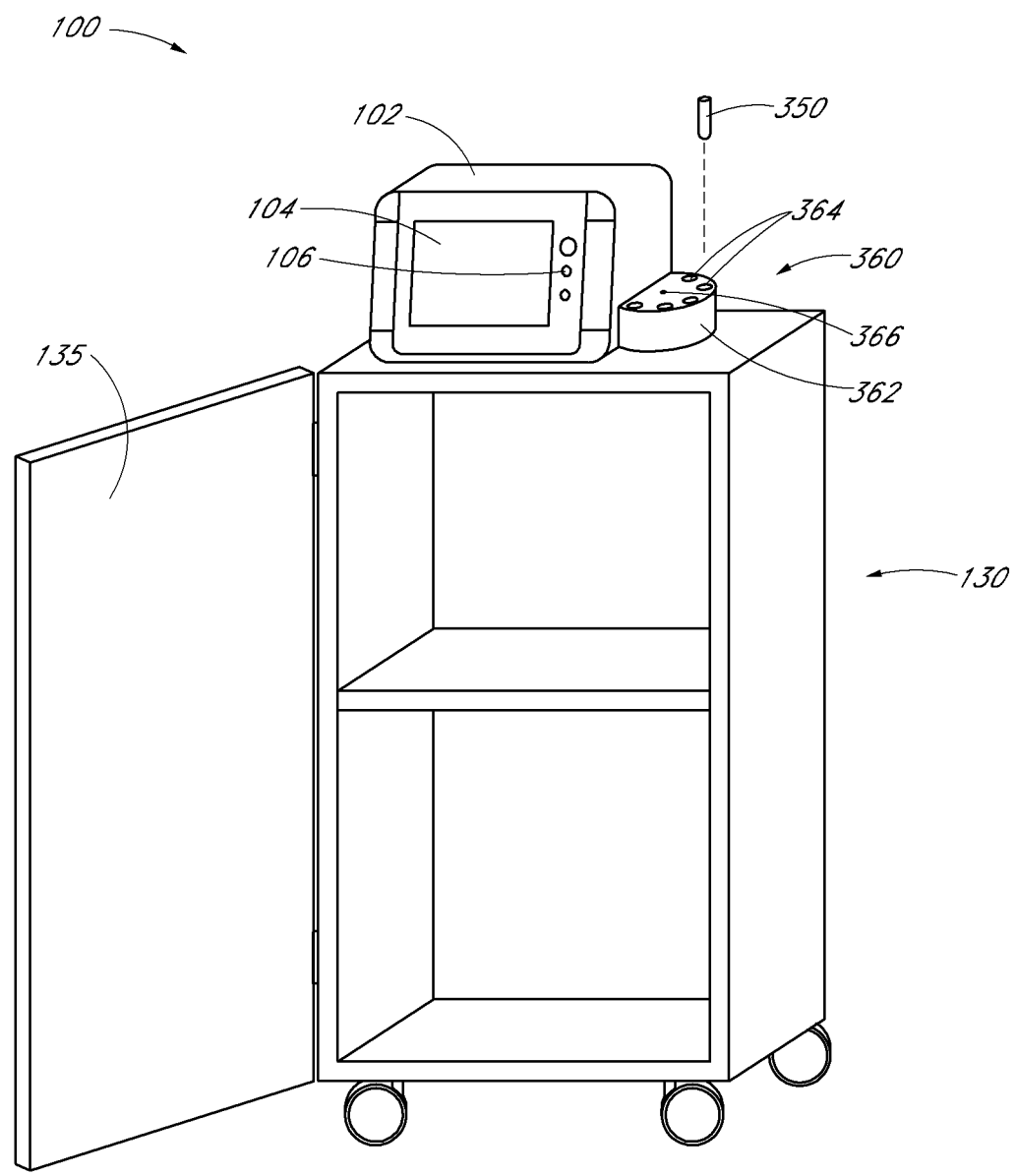
FIG. 3A illustrates an embodiment of the apparatus in FIG. 1 that is not configured to be connected to a patient but which receives a fluid sample from an extracorporeal fluid container such as, for example, a test tube. This embodiment of the apparatus advantageously provides in vitro analysis of a fluid sample.

FIG. 3 illustrates the apparatus 100 of FIG. 1 as it can be connected to a patient 302. The monitoring device 102 can be used to determine the concentration of one or more substances in a sample fluid. The sample fluid can come can come from the patient 302, as illustrated in FIG. 3, or the sample fluid can come from a fluid container, as illustrated in FIG. 3A. In some preferred embodiments, the sample fluid is whole blood.

In some embodiments (see, e.g., FIG. 3), the monitoring device 102 can also deliver an infusion fluid to the patient 302. An infusion fluid container 304 (e.g., a saline bag), which can contain infusion fluid (e.g., saline and/or medication), can be supported by the hook 112. The monitoring device 102 can be in fluid communication with both the container 304 and the sample fluid source (e.g., the patient 302), through tubes 306. The infusion fluid can comprise any combination of fluids and/or chemicals. Some advantageous examples include (but are not limited to): water, saline, dextrose, lactated Ringer's solution, drugs, and insulin.

The example monitoring device 102 schematically illustrated in FIG. 3 allows the infusion fluid to pass to the patient 302 and/or uses the infusion fluid itself (e.g., as a flushing fluid or a standard with known optical properties, as discussed further below). In some embodiments, the monitoring device 102 may not employ infusion fluid. The monitoring device 102 may thus draw samples without delivering any additional fluid to the patient 302. The monitoring device 102 can include, but is not limited to, fluid handling and analysis apparatuses, connectors, passageways, catheters, tubing, fluid control elements, valves, pumps, fluid sensors, pressure sensors, temperature sensors, hematocrit sensors, hemoglobin sensors, colorimetric sensors, gas (e.g., "bubble") sensors, fluid conditioning elements, gas injectors, gas filters, blood plasma separators, and/or communication devices (e.g., wireless devices) to permit the transfer of information within the monitoring device 102 or between the monitoring device 102 and a network.

In some embodiments, the apparatus 100 is not connected to a patient and may receive fluid samples from a container such as a decanter, flask, beaker, tube, cartridge, test strip, etc., or any other extracorporeal fluid source. The container may include a biological fluid sample such as, e.g., a body fluid sample. For example, FIG. 3A schematically illustrates an embodiment of the monitoring device 102 that is configured to receive a fluid sample from one or more test tubes 350. This embodiment of the monitoring device 102 is configured to perform in vitro analysis of a fluid (or a fluid component) in the test tube 350. The test tube 350 may comprise a tube, vial, bottle, or other suitable container or vessel. The test tube 350 may include an opening disposed at one end of the tube through which the fluid sample may be added prior to delivery of the test tube to the monitoring device 102. In some embodiments, the test tubes 350 may also include a cover adapted to seal the opening of the tube. The cover may include an aperture configured to permit a tube, nozzle, needle, pipette, or syringe to dispense the fluid sample into the test tube 350. The test tubes 350 may comprise a material such as, for example, glass, polyethylene, or polymeric compounds. In various embodiments, the test tubes 350 may be re-usable units or may be disposable, single-use units. In certain embodiments, the test tubes 350 may comprise commercially available low pressure/vacuum sample bottles, test bottles, or test tubes.

In the embodiment shown in FIG. 3A, the monitoring device 102 comprises a fluid delivery system 360 configured to receive a container (e.g., the test tube 350) containing a fluid sample and deliver the fluid sample to a fluid handling system (such as, e.g., fluid handling system 404 described below). In some embodiments, the fluid handling system delivers a portion of the fluid sample to an analyte detection system for in vitro measurement of one or more physiological parameters (e.g., an analyte concentration). Prior to measurement, the fluid handling system may, in some embodiments, separate the fluid sample into components, and a measurement may be performed on one or more of the components. For example, the fluid sample in the test tube 350 may comprise whole blood, and the fluid handling system may separate blood plasma from the sample (e.g., by filtering and/or centrifuging).

In the embodiment illustrated in FIG. 3A, the fluid delivery system 360 comprises a carousel 362 having one or more openings 364 adapted to receive the test tube 350. The carousel 362 may comprise one, two, four, six, twelve, or more openings 364. In the illustrated embodiment, the carousel 362 is configured to rotate around a central axis or spindle 366 so that a test tube 350 inserted into one of the openings 364 is delivered to the monitoring device 102. In certain embodiments, the fluid handling system of the monitoring device 102 comprises a sampling probe that is configured to collect a portion of the fluid sample from the test tube 350 (e.g., by suction or aspiration). The collected portion may then be transported in the device 102 as further described below (see, e.g., FIGS. 4-7). For example, in one embodiment suitable for use with whole blood, the collected portion of the whole blood sample is transported to a centrifuge for separation into blood plasma, a portion of the blood plasma is transported to an infrared spectroscope for measurement of one or more analytes (e.g., glucose), and the measured blood plasma is then transported to a waste container for disposal.

In other embodiments of the apparatus 100 shown in FIG. 3A, the fluid delivery system 360 may comprise a turntable, rack, or caddy adapted to receive the test tube 350. In yet other embodiments, the monitoring device 102 may comprise an inlet port adapted to receive the test tube 350. Additionally, in other embodiments, the fluid sample may be delivered to the apparatus 100 using a test cartridge, a test strip, or other suitable container. Many variations are possible.

In some embodiments, one or more components of the apparatus 100 can be located at another facility, room, or other suitable remote location. One or more components of the monitoring device 102 can communicate with one or more other components of the monitoring device 102 (or with other devices) by communication interface(s) such as, but not limited to, optical interfaces, electrical interfaces, and/or wireless interfaces. These interfaces can be part of a local network, internet, wireless network, or other suitable networks.

System Overview

Figure 4:
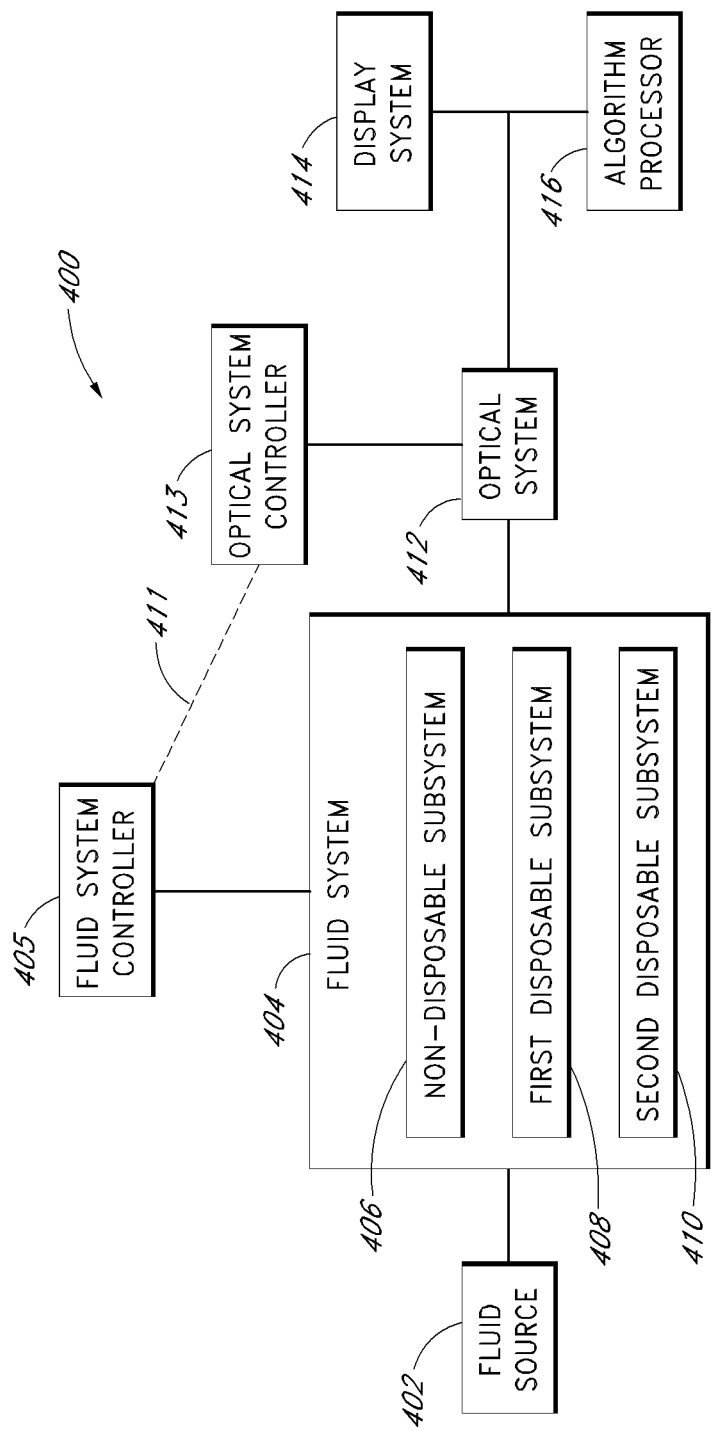
FIG. 4 is a block diagram of an embodiment of a system for withdrawing and analyzing fluid samples.

FIG. 4 is a block diagram of a system 400 for sampling and analyzing fluid samples. The monitoring device 102 can comprise such a system. The system 400 can include a fluid source 402 connected to a fluid-handling system 404. The fluid-handling system 404 includes fluid passageways and other components that direct fluid samples. Samples can be withdrawn from the fluid source 402 and analyzed by an optical system 412. The fluid-handling system 404 can be controlled by a fluid system controller 405, and the optical system 412 can be controlled by an optical system controller 413. The sampling and analysis system 400 can also include a display system 414 and an algorithm processor 416 that assist in fluid sample analysis and presentation of data.

In some embodiments, the sampling and analysis system 400 is a mobile point-of-care apparatus that monitors physiological parameters such as, for example, blood glucose concentration. Components within the system 400 that may contact fluid and/or a patient, such as tubes and connectors, can be coated with an antibacterial coating to reduce the risk of infection. Connectors between at least some components of the system 400 can include a self-sealing valve, such as a spring valve, in order to reduce the risk of contact between port openings and fluids, and to guard against fluid escaping from the system. Other components can also be included in a system for sampling and analyzing fluid in accordance with the described embodiments.

The sampling and analysis system 400 can include a fluid source 402 (or more than one fluid source) that contain(s) fluid to be sampled. The fluid-handling system 404 of the sampling and analysis system 400 is connected to, and can draw fluid from, the fluid source 402. The fluid source 402 can be, for example, a blood vessel such as a vein or an artery, a container such as a decanter, flask, beaker, tube, cartridge, test strip, etc., or any other corporeal or extracorporeal fluid source. For example, in some embodiments, the fluid source 402 may be a vein or artery in the patient 302 (see, e.g., FIG. 3). In other embodiments, the fluid source 402 may comprise an extracorporeal container 350 of fluid delivered to the system 400 for analysis (see, e.g., FIG. 3B). The fluid to be sampled can be, for example, blood, plasma, interstitial fluid, lymphatic fluid, or another fluid. In some embodiments, more than one fluid source can be present, and more than one fluid and/or type of fluid can be provided.

In some embodiments, the fluid-handling system 404 withdraws a sample of fluid from the fluid source 402 for analysis, centrifuges at least a portion of the sample, and prepares at least a portion of the sample for analysis by an optical sensor such as a spectrophotometer (which can be part of an optical system 412, for example). These functions can be controlled by a fluid system controller 405, which can also be integrated into the fluid-handling system 404. The fluid system controller 405 can also control the additional functions described below.

In some embodiments, at least a portion of the sample is returned to the fluid source 402. At least some of the sample, such as portions of the sample that are mixed with other materials or portions that are otherwise altered during the sampling and analysis process, or portions that, for any reason, are not to be returned to the fluid source 402, can also be placed in a waste bladder (not shown in FIG. 4). The waste bladder can be integrated into the fluid-handling system 404 or supplied by a user of the system 400. The fluid-handling system 404 can also be connected to a saline source, a detergent source, and/or an anticoagulant source, each of which can be supplied by a user, attached to the fluid-handling system 404 as additional fluid sources, and/or integrated into the fluid-handling system 404.

Components of the fluid-handling system 404 can be modularized into one or more non-disposable, disposable, and/or replaceable subsystems. In the embodiment shown in FIG. 4, components of the fluid-handling system 404 are separated into a non-disposable subsystem 406, a first disposable subsystem 408, and a second disposable subsystem 410.

The non-disposable subsystem 406 can include components that, while they may be replaceable or adjustable, do not generally require regular replacement during the useful lifetime of the system 400. In some embodiments, the non-disposable subsystem 406 of the fluid-handling system 404 includes one or more reusable valves and sensors. For example, the non-disposable subsystem 406 can include one or more pinch valves (or non-disposable portions thereof), ultrasonic bubble sensors, non-contact pressure sensors, and optical blood dilution sensors. The non-disposable subsystem 406 can also include one or more pumps (or non-disposable portions thereof). In some embodiments, the components of the non-disposable subsystem 406 are not directly exposed to fluids and/or are not readily susceptible to contamination.

The first and second disposable subsystems 408, 410 can include components that are regularly replaced under certain circumstances in order to facilitate the operation of the system 400. For example, the first disposable subsystem 408 can be replaced after a certain period of use, such as a few days, has elapsed. Replacement may be necessary, for example, when a bladder within the first disposable subsystem 408 is filled to capacity. Such replacement may mitigate fluid system performance degradation associated with and/or contamination wear on system components.

In some embodiments, the first disposable subsystem 408 includes components that may contact fluids such as patient blood, saline, flushing solutions, anticoagulants, and/or detergent solutions. For example, the first disposable subsystem 408 can include one or more tubes, fittings, cleaner pouches and/or waste bladders. The components of the first disposable subsystem 408 can be sterilized in order to decrease the risk of infection and can be configured to be easily replaceable.

In some embodiments, the second disposable subsystem 410 can be designed to be replaced under certain circumstances. For example, the second disposable subsystem 410 can be replaced when the patient being monitored by the system 400 is changed. The components of the second disposable subsystem 410 may not need replacement at the same intervals as the components of the first disposable subsystem 408. For example, the second disposable subsystem 410 can include a sample holder and/or at least some components of a centrifuge, components that may not become filled or quickly worn during operation of the system 400. Replacement of the second disposable subsystem 410 can decrease or eliminate the risk of transferring fluids from one patient to another during operation of the system 400, enhance the measurement performance of system 400, and/or reduce the risk of contamination or infection.

In some embodiments, the sample holder of the second disposable subsystem 410 receives the sample obtained from the fluid source 402 via fluid passageways of the first disposable subsystem 408. The sample holder is a container that can hold fluid for the centrifuge and can include a window to the sample for analysis by a spectrometer. In some embodiments, the sample holder includes windows that are made of a material that is substantially transparent to electromagnetic radiation in the mid-infrared range of the spectrum. For example, the sample holder windows can be made of calcium fluoride.

An injector can provide a fluid connection between the first disposable subsystem 408 and the sample holder of the second disposable subsystem 410. In some embodiments, the injector can be removed from the sample holder to allow for free spinning of the sample holder during centrifugation.

In some embodiments, the components of the sample are separated by centrifuging at a high speed for a period of time before measurements are performed by the optical system 412. For example, a blood sample can be centrifuged at 7200 RPM for 2 minutes in order to separate plasma from other blood components for analysis. In some embodiments, a blood sample can be centrifuged at 4500 RPM for two minutes, or for some other length of time. Separation of a sample into the components can permit measurement of solute (e.g., glucose) concentration in plasma, for example, without interference from other blood components. This kind of post-separation measurement, (sometimes referred to as a "direct measurement") has advantages over a solute measurement taken from whole blood because the proportions of plasma to other components need not be known or estimated in order to infer plasma glucose concentration. In some embodiments, the separated plasma can be analyzed electrically using one or more electrodes instead of, or in addition to, being analyzed optically. This analysis may occur within the same device, or within a different device. For example, in certain embodiments, an optical analysis device can separate blood into components, analyze the components, and then allow the components to be transported to another analysis device that can further analyze the components (e.g., using electrical and/or electrochemical measurements).

An anticoagulant, such as, for example, heparin can be added to the sample before centrifugation to prevent clotting. The fluid-handling system 404 can be used with a variety of anticoagulants, including anticoagulants supplied by a hospital or other user of the monitoring system 400. A detergent solution formed by mixing detergent powder from a pouch connected to the fluid-handling system 404 with saline can be used to periodically clean residual protein and other sample remnants from one or more components of the fluid-handling system 404, such as the sample holder. Sample fluid to which anticoagulant has been added and used detergent solution can be transferred into the waste bladder.

The system 400 shown in FIG. 4 includes an optical system 412 that can measure optical properties (e.g., transmission) of a fluid sample (or a portion thereof). In some embodiments, the optical system 412 measures transmission in the mid-infrared range of the spectrum. In some embodiments, the optical system 412 includes a spectrometer that measures the transmission of broadband infrared light through a portion of a sample holder filled with fluid. The spectrometer need not come into direct contact with the sample. As used herein, the term "sample holder" is a broad term that carries its ordinary meaning as an object that can provide a place for fluid. The fluid can enter the sample holder by flowing.

In some embodiments, the optical system 412 includes a filter wheel that contains one or more filters. In some embodiments, twenty-five filters are mounted on the filter wheel. The optical system 412 includes a light source that passes light through a filter and the sample holder to a detector. In some embodiments, a stepper motor moves the filter wheel in order to position a selected filter in the path of the light. An optical encoder can also be used to finely position one or more filters. In some embodiments, one or more tunable filters may be used to filter light into multiple wavelengths. The one or more tunable filters may provide the multiple wavelengths of light at the same time or at different times (e.g., sequentially). The light source included in the optical system 412 may emit radiation in the ultraviolet, visible, near-infrared, mid-infrared, and/or far-infrared regions of the electromagnetic spectrum. In some embodiments, the light source can be a broadband source that emits radiation in a broad spectral region (e.g., from about 1500 nm to about 6000 nm). In other embodiments, the light source may emit radiation at certain specific wavelengths. The light source may comprise one or more light emitting diodes (LEDs) emitting radiation at one or more wavelengths in the radiation regions described herein. In other embodiments, the light source may comprise one or more laser modules emitting radiation at one or more wavelengths. The laser modules may comprise a solid state laser (e.g., a Nd:YAG laser), a semiconductor based laser (e.g., a GaAs and/or InGaAsP laser), and/or a gas laser (e.g., an Ar-ion laser). In some embodiments, the laser modules may comprise a fiber laser. The laser modules may emit radiation at certain fixed wavelengths. In some embodiments, the emission wavelength of the laser module(s) may be tunable over a wide spectral range (e.g., about 30 nm to about 100 nm). In some embodiments, the light source included in the optical system 412 may be a thermal infrared emitter. The light source can comprise a resistive heating element, which, in some embodiments, may be integrated on a thin dielectric membrane on a micromachined silicon structure. In one embodiment the light source is generally similar to the electrical modulated thermal infrared radiation source, IRSource™, available from the Axetris Microsystems division of Leister Technologies, LLC (Itasca, Ill.).

The optical system 412 can be controlled by an optical system controller 413. The optical system controller can, in some embodiments, be integrated into the optical system 412. In some embodiments, the fluid system controller 405 and the optical system controller 413 can communicate with each other as indicated by the line 411. In some embodiments, the function of these two controllers can be integrated and a single controller can control both the fluid-handling system 404 and the optical system 412. Such an integrated control can be advantageous because the two systems are preferably integrated, and the optical system 412 is preferably configured to analyze the very same fluid handled by the fluid-handling system 404. Indeed, portions of the fluid-handling system 404 (e.g., the sample holder described above with respect to the second disposable subsystem 410 and/or at least some components of a centrifuge) can also be components of the optical system 412. Accordingly, the fluid-handling system 404 can be controlled to obtain a fluid sample for analysis by optical system 412, when the fluid sample arrives, the optical system 412 can be controlled to analyze the sample, and when the analysis is complete (or before), the fluid-handling system 404 can be controlled to return some of the sample to the fluid source 402 and/or discard some of the sample, as appropriate.

Figure 24:
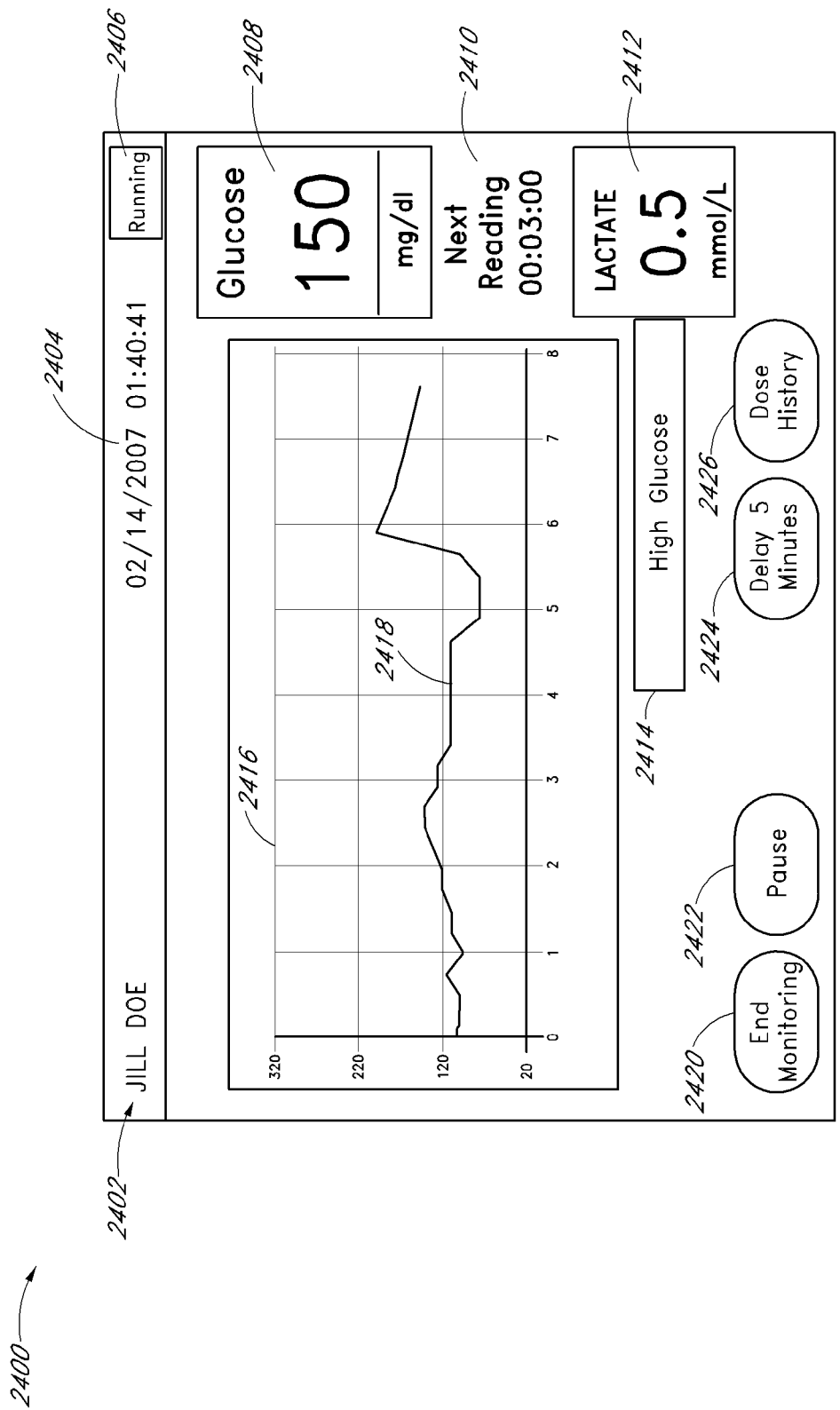
FIGS. 24 and 25 schematically illustrate the visual appearance of embodiments of a user interface for a system for withdrawing and analyzing fluid samples.
Figure 25:
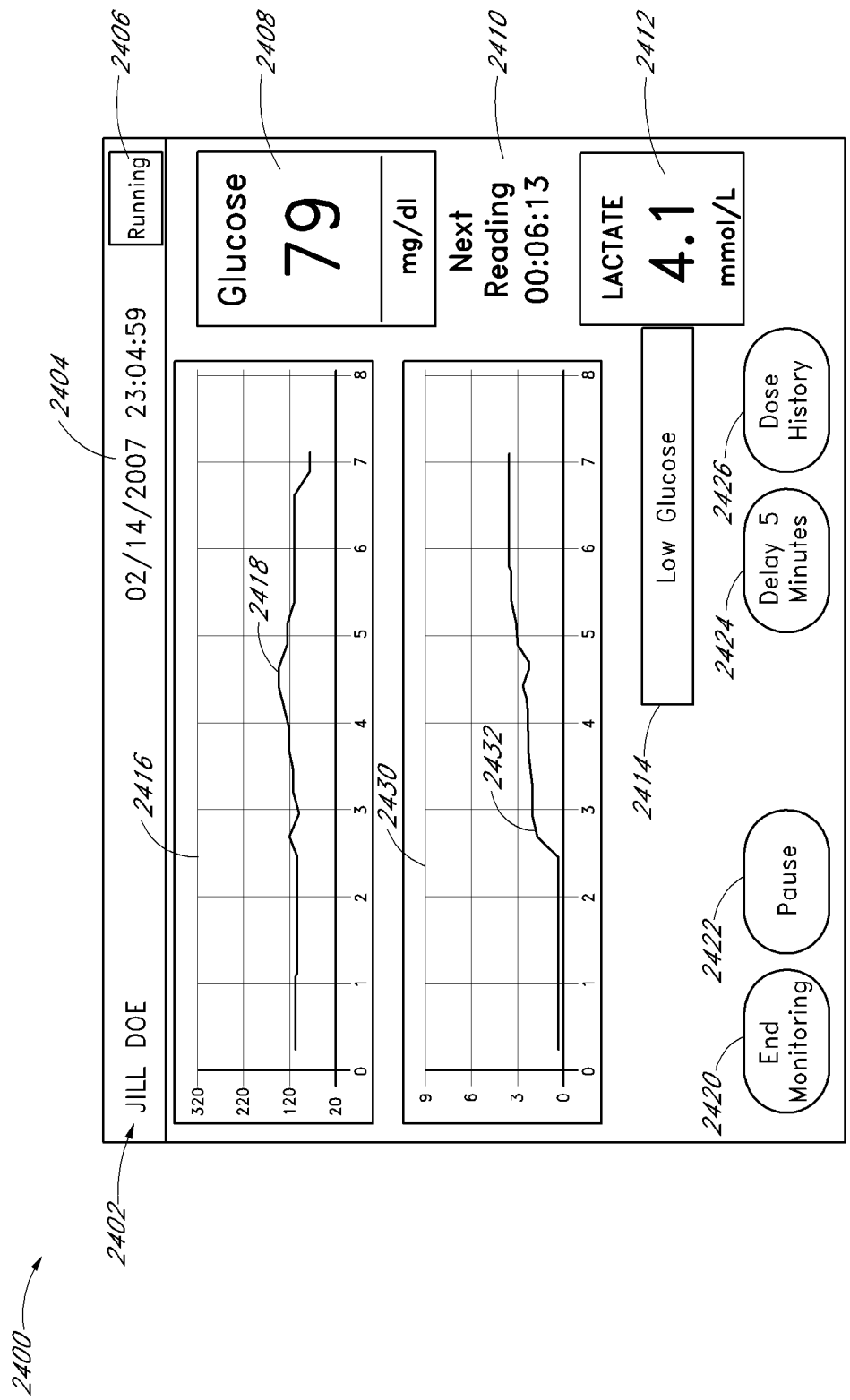

The system 400 shown in FIG. 4 includes a display system 414 that provides for communication of information to a user of the system 400. In some embodiments, the display 414 can be replaced by or supplemented with other communication devices that communicate in non-visual ways. The display system 414 can include a display processor that controls or produces an interface to communicate information to the user. The display system 414 can include a display screen. One or more parameters such as, for example, blood glucose concentration, system 400 operating parameters, and/or other operating parameters can be displayed on a monitor (not shown) associated with the system 400. An example of one way such information can be displayed is shown in FIGS. 24 and 25. In some embodiments, the display system 414 can communicate measured physiological parameters and/or operating parameters to a computer system over a communications connection.

The system 400 shown in FIG. 4 includes an algorithm processor 416 that can receive spectral information, such as optical density (OD) values (or other analog or digital optical data) from the optical system 412 and or the optical system controller 413. In some embodiments, the algorithm processor 416 calculates one or more physiological parameters and can analyze the spectral information. Thus, for example and without limitation, a model can be used that determines, based on the spectral information, physiological parameters of fluid from the fluid source 402. The algorithm processor 416, a controller that may be part of the display system 414, and any embedded controllers within the system 400 can be connected to one another with a communications bus.

Some embodiments of the systems described herein (e.g., the system 400), as well as some embodiments of each method described herein, can include a computer program accessible to and/or executable by a processing system, e.g., a one or more processors and memories that are part of an embedded system. Indeed, the controllers may comprise one or more computers and/or may use software. Thus, as will be appreciated by those skilled in the art, various embodiments may be embodied as a method, an apparatus such as a special purpose apparatus, an apparatus such as a data processing system, or a carrier medium, e.g., a computer program product. The carrier medium carries one or more computer readable code segments for controlling a processing system to implement a method. Accordingly, various embodiments may take the form of a method, an entirely hardware embodiment, an entirely software embodiment or an embodiment combining software and hardware aspects. Furthermore, any one or more of the disclosed methods (including but not limited to the disclosed methods of measurement analysis, interferent determination, and/or calibration constant generation) may be stored as one or more computer readable code segments or data compilations on a carrier medium. Any suitable computer readable carrier medium may be used including a magnetic storage device such as a diskette or a hard disk; a memory cartridge, module, card or chip (either alone or installed within a larger device); or an optical storage device such as a CD or DVD.

Fluid Handling System

Figure 5:
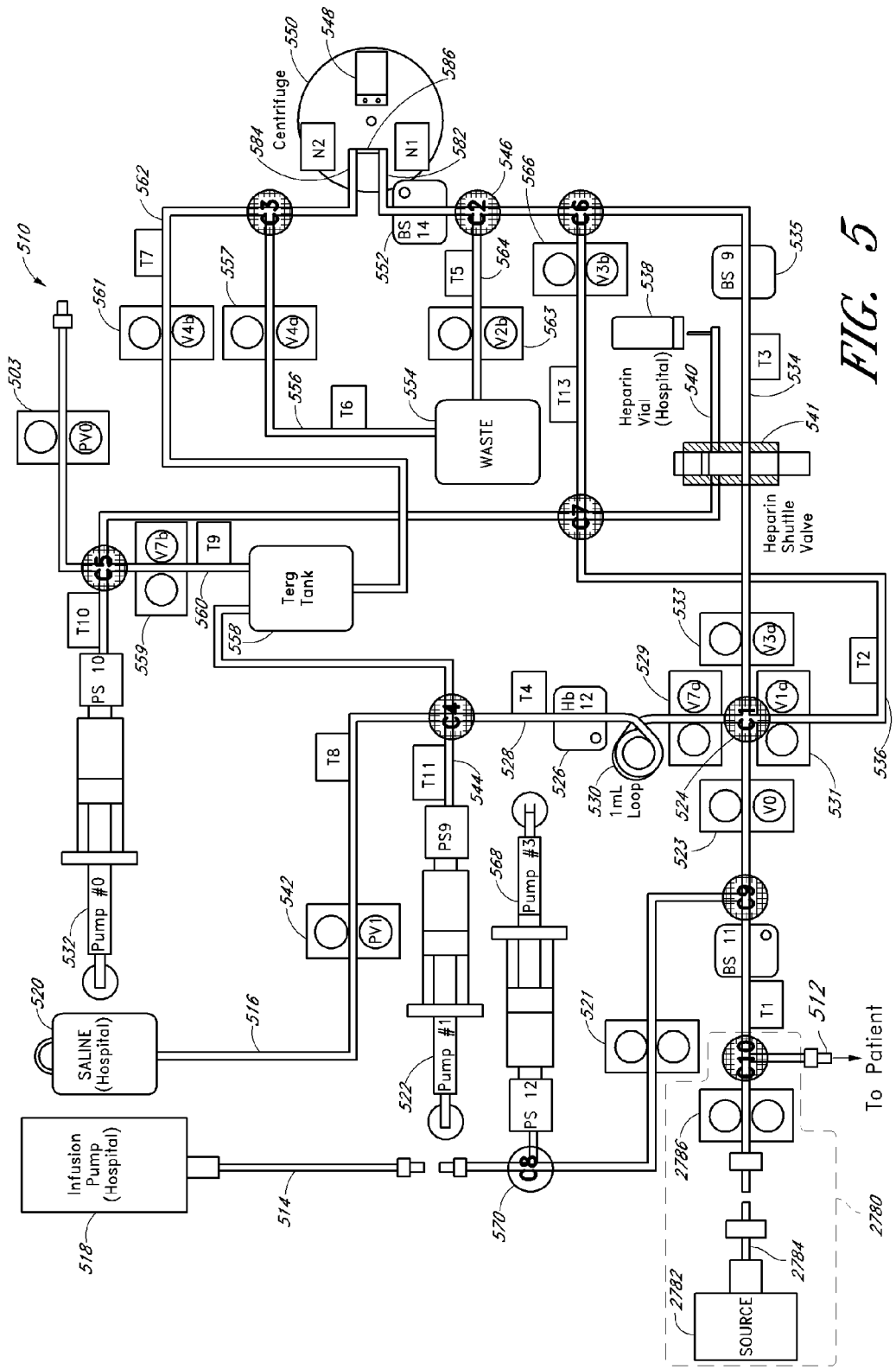
FIG. 5 schematically illustrates an embodiment of a fluid system that can be part of a system for withdrawing and analyzing fluid samples.

The generalized fluid-handling system 404 can have various configurations. In this context, FIG. 5 schematically illustrates the layout of an example embodiment of a fluid system 510. In this schematic representation, various components are depicted that may be part of a non-disposable subsystem 406, a first disposable subsystem 408, a second disposable subsystem 410, and/or an optical system 412. The fluid system 510 is described practically to show an example cycle as fluid is drawn and analyzed.

In addition to the reference numerals used below, the various portions of the illustrated fluid system 510 are labeled for convenience with letters to suggest their roles as follows: T# indicates a section of tubing. C# indicates a connector that joins multiple tubing sections. V# indicates a valve. BS# indicates a bubble sensor or ultrasonic air detector. N# indicates a needle (e.g., a needle that injects sample into a sample holder). PS# indicates a pressure sensor (e.g., a reusable pressure sensor). Pump# indicates a fluid pump (e.g., a syringe pump with a disposable body and reusable drive). "Hb 12" indicates a sensor for hemoglobin (e.g., a dilution sensor that can detect hemoglobin optically).

The function of the valves, pumps, actuators, drivers, motors (e.g., the centrifuge motor), etc. described below is controlled by one or more controllers (e.g., the fluid system controller 405, the optical system controller 413, etc.) The controllers can include software, computer memory, electrical and mechanical connections to the controlled components, etc.

At the start of a measurement cycle, most lines, including a patient tube 512 (T1), an Hb sensor tube 528 (T4), an anticoagulant valve tube 534 (T3), and a sample cell 548 can be filled with saline that can be introduced into the system through the infusion tube 514 and the saline tube 516, and which can come from an infusion pump 518 and/or a saline bag 520. The infusion pump 518 and the saline bag 520 can be provided separately from the system 510. For example, a hospital can use existing saline bags and infusion pumps to interface with the described system. The infusion valve 521 can be open to allow saline to flow into the tube 512 (T1).

Before drawing a sample, the saline in part of the system 510 can be replaced with air. Thus, for example, the following valves can be closed: air valve 503 (PV0), the terg tank valve 559 (V7b), 566 (V3b), 523 (V0), 529 (V7a), and 563 (V2b). At the same time, the following valves can be open: valves 531 (V1a), 533 (V3a) and 577 (V4a). Simultaneously, a second pump 532 (pump #0) pumps air through the system 510 (including tube 534 (T3), sample cell 548, and tube 556 (T6)), pushing saline through tube 534 (T3) and sample cell 548 into a waste bladder 554.

Next, a sample can be drawn. With the valves 542 (PV1), 559 (V7b), and 561 (V4b) closed, a first pump 522 (pump #1) is actuated to draw sample fluid to be analyzed (e.g. blood) from a fluid source (e.g., a laboratory sample container, a living patient, etc.) up into the patient tube 512 (T1), through the tube past the two flanking portions of the open pinch-valve 523 (V0), through the first connector 524 (C1), into the looped tube 530, past the hemoglobin sensor 526 (Hb12), and into the Hb sensor tube 528 (T4). During this process, the valve 529 (V7a) and 523 (V0) are open to fluid flow, and the valves 531 (V1a), 533 (V3a), 542 (PV1), 559 (V7b), and 561 (V4b) can be closed and therefore block (or substantially block) fluid flow by pinching the tube.

Before drawing the sample, the tubes 512 (T1) and 528 (T4) are filled with saline and the hemoglobin (Hb) level is zero. The tubes that are filled with saline are in fluid communication with the sample source (e.g., the fluid source 402). The sample source can be the vessels of a living human or a pool of liquid in a laboratory sample container, for example. When the saline is drawn toward the first pump 522, fluid to be analyzed is also drawn into the system because of the suction forces in the closed fluid system. Thus, the first pump 522 draws a relatively continuous column of fluid that first comprises generally nondiluted saline, then a mixture of saline and sample fluid (e.g., blood), and then eventually nondiluted sample fluid. In the example illustrated here, the sample fluid is blood.

The hemoglobin sensor 526 (Hb12) detects the level of Hemoglobin in the sample fluid. As blood starts to arrive at the hemoglobin sensor 526 (Hb12), the sensed hemoglobin level rises. A hemoglobin level can be selected, and the system can be pre-set to determine when that level is reached. A controller such as the fluid system controller 405 of FIG. 4 can be used to set and react to the pre-set value, for example. In some embodiments, when the sensed hemoglobin level reaches the pre-set value, substantially undiluted sample is present at the first connector 524 (C1). The preset value can depend, in part, on the length and diameter of any tubes and/or passages traversed by the sample. In some embodiments, the pre-set value can be reached after approximately 2 mL of fluid (e.g., blood) has been drawn from a fluid source. A nondiluted sample can be, for example, a blood sample that is not diluted with saline solution, but instead has the characteristics of the rest of the blood flowing through a patient's body. A loop of tubing 530 (e.g., a 1-mL loop) can be advantageously positioned as illustrated to help insure that undiluted fluid (e.g., undiluted blood) is present at the first connector 524 (C1) when the hemoglobin sensor 526 registers that the preset Hb threshold is crossed. The loop of tubing 530 provides additional length to the Hb sensor tube 528 (T4) to make it less likely that the portion of the fluid column in the tubing at the first connector 524 (C1) has advanced all the way past the mixture of saline and sample fluid, and the nondiluted blood portion of that fluid has reached the first connector 524 (C1).

In some embodiments, when nondiluted blood is present at the first connector 524 (C1), a sample is mixed with an anticoagulant and is directed toward the sample cell 548. An amount of anticoagulant (e.g., heparin) can be introduced into the tube 534 (T3), and then the undiluted blood is mixed with the anticoagulant. A heparin vial 538 (e.g., an insertable vial provided independently by the user of the system 510) can be connected to a tube 540. An anticoagulant valve 541 (which can be a shuttle valve, for example) can be configured to connect to both the tube 540 and the anticoagulant valve tube 534 (T3). The valve can open the tube 540 to a suction force (e.g., created by the pump 532), allowing heparin to be drawn from the vial 538 into the valve 541. Then, the anticoagulant valve 541 can slide the heparin over into fluid communication with the anticoagulant valve tube 534 (T3). The anticoagulant valve 541 can then return to its previous position. Thus, heparin can be shuttled from the tube 540 into the anticoagulant valve tube 534 (T3) to provide a controlled amount of heparin into the tube 534 (T3).

With the valves 542 (PV1), 559 (V7b), 561 (V4b), 523 (V0), 531 (V1a), 566 (V3b), and 563 (V2b) closed, and the valves 529 (V7a) and 553 (V3a) open, first pump 522 (pump #1) pushes the sample from tube 528 (T4) into tube 534 (T3), where the sample mixes with the heparin injected by the anticoagulant valve 541 as it flows through the system 510. As the sample proceeds through the tube 534 (T3), the air that was previously introduced into the tube 534 (T3) is displaced. The sample continues to flow until a bubble sensor 535 (BS9) indicates a change from air to a liquid, and thus the arrival of a sample at the bubble sensor. In some embodiments, the volume of tube 534 (T3) from connector 524 (C1) to bubble sensor 535 (BS9) is a known amount, and may be, for example, approximately 100 microliters.

When bubble sensor 535 (BS9) indicates the presence of a sample, the remainder of the sampled blood can be returned to its source (e.g., the patient veins or arteries). The first pump 522 (pump #1) pushes the blood out of the Hb sensor tube 528 (T4) and back to the patient by opening the valve 523 (V0), closing the valves 531 (V1a) and 533 (V3a), and keeping the valve 529 (V7a) open. The Hb sensor tube 528 (T4) is preferably flushed with approximately 2 mL of saline. This can be accomplished by closing the valve 529 (V7a), opening the valve 542 (PV1), drawing saline from the saline source 520 into the tube 544, closing the valve 542 (PV1), opening the valve 529 (V7a), and forcing the saline down the Hb sensor tube 528 (T4) with the pump 522. In some embodiments, less than two minutes elapse between the time that blood is drawn from the patient and the time that the blood is returned to the patient.

Following return of the unused patient blood sample, the sample is pushed up the anticoagulant valve tube 534 (T3), through the second connector 546 (C2), and into the sample cell 548, which can be located on the centrifuge rotor 550. This fluid movement is facilitated by the coordinated action (either pushing or drawing fluid) of the pump 522 (pump #1), the pump 532 (pump #0), and the various illustrated valves. In particular, valve 531 (V1a) can be opened, and valves 503 (PV0) and 559 (V7b) can be closed. Pump movement and valve position corresponding to each stage of fluid movement can be coordinated by one ore multiple controllers, such as the fluid system controller 405 of FIG. 4.

After the unused sample is returned to the patient, the sample can be divided into separate slugs before being delivered into the sample cell 548. Thus, for example, valve 553 (V3a) is opened, valves 566 (V3b), 523 (V0) and 529 (V7a) are closed, and the pump 532 (pump #0) uses air to push the sample toward sample cell 548. In some embodiments, the sample (for example 100 microliters) is divided into four "slugs" of sample, each separated by a small amount of air. As used herein, the term "slug" refers to a continuous column of fluid that can be relatively short. Slugs can be separated from one another by small amounts of air (or bubbles) that can be present at intervals in the tube. In some embodiments, the slugs are formed by injecting or drawing air into fluid in the first connector 546 (C2).

In some embodiments, when the leading edge of the sample reaches blood sensor 553 (BS14), a small amount of air (the first "bubble") is injected at a connector C6. This bubble helps define the first "slug" of liquid, which extends from the bubble sensor to the first bubble. In some embodiments, the valves 533 (V3a) and 556 (V3b) are alternately opened and closed to form a bubble at connector C6, and the sample is pushed toward the sample cell 548. Thus, for example, with pump 532 actuated, valve 566 V(3b) is briefly opened and valve 533 (V3a) is briefly closed to inject a first air bubble into the sample.

In some embodiments, the volume of the tube 534 (T3) from the connector 546 (C2) to the bubble sensor 552 (BS14) is less than the volume of tube 534 (T3) from the connector 524 (C1) to the bubble sensor 535 (BS9). Thus, for example and without limitation, the volume of the tube 534 (T3) from the connector 524 (C1) to the bubble sensor 535 (BS9) is approximately 100 μL, and the volume of the tube 534 (T3) from the connector 546 (C2) to the bubble sensor 552 (BS14) is approximately 15 μL. In some embodiments, four blood slugs are created. The first three blood slugs can have a volume of approximately 15 μL and the fourth can have a volume of approximately 35 μL.

A second slug can be prepared by opening the valve 553 (V3a), closing the valve 566 (V3b), with pump 532 (pump #0) operating to push the first slug through a first sample cell holder interface tube 582 (N1), through the sample cell 548, through a second sample cell holder interface tube 584 (N2), and toward the waste bladder 554. When the first bubble reaches the bubble sensor 552 (BS 14), the open/closed configurations of valves 553 (V3a) and 566 (V3b) are reversed, and a second bubble is injected into the sample, as before. A third slug can be prepared in the same manner as the second (pushing the second bubble to bubble sensor 552 (BS 14) and injecting a third bubble). After the injection of the third air bubble, the sample can be pushed through system 510 until the end of the sample is detected by bubble sensor 552 (BS 14). The system can be designed such that when the end of the sample reaches this point, the last portion of the sample (a fourth slug) is within the sample cell 548, and the pump 532 can stop forcing the fluid column through the anticoagulant valve tube 534 (T3) so that the fourth slug remains within the sample cell 548. Thus, the first three blood slugs can serve to flush any residual saline out the sample cell 548. The three leading slugs can be deposited in the waste bladder 554 by passing through the tube 556 (T6) and past the tube-flanking portions of the open pinch valve 557 (V4a).

In some embodiments, the fourth blood slug is centrifuged for two minutes at 7200 RPM or at 4500 RPM, to take two examples. Thus, for example, the sample cell holder interface tubes 582 (N1) and 584 (N2) disconnect the sample cell 548 from the tubes 534 (T3) and 562 (T7), permitting the centrifuge rotor 550 and the sample cell 548 to spin together. Spinning separates a sample (e.g., blood) into its components, isolates the plasma, and positions the plasma in the sample cell 548 for measurement. The centrifuge 550 can be stopped with the sample cell 548 in a beam of radiation (not shown) for analysis. The radiation, a detector, and logic can be used to analyze the a portion of the sample (e.g., the plasma) spectroscopically (e.g., for glucose, lactate, or other analyte concentration). In some embodiments, some or all of the separated components (e.g., the isolated plasma) may be transported to a different analysis chamber. For example, another analysis chamber can have one or more electrodes in electrical communication with the chamber's contents, and the separated components may be analyzed electrically. At any suitable point, one or more of the separated components can be transported to the waste bladder 554 when no longer needed. In some chemical analysis systems and apparatus, the separated components are analyzed electrically. Analysis devices may be connected serially, for example, so that the analyzed substance from an optical analysis system (e.g., an "OptiScanner®" fluid analyzer) can be transferred to an independent analysis device (e.g., a chemical analysis device) for subsequent analysis. In certain embodiments, the analysis devices are integrated into a single system. Many variations are possible.

In some embodiments, portions of the system 510 that contain blood after the sample cell 548 has been provided with a sample are cleaned to prevent blood from clotting. Accordingly, the centrifuge rotor 550 can include two passageways for fluid that may be connected to the sample cell holder interface tubes 582 (N1) and 584 (N2). One passageway is sample cell 548, and a second passageway is a shunt 586. An embodiment of the shunt 586 is illustrated in more detail in FIG. 16 (see reference numeral 1586).

The shunt 586 can allow cleaner (e.g., tergazyme A) to flow through and clean the sample cell holder interface tubes without flowing through the sample cell 548. After the sample cell 548 is provided with a sample, the interface tubes 582 (N1) and 584 (N2) are disconnected from the sample cell 548, the centrifuge rotor 550 is rotated to align the shunt 586 with the interface tubes 582 (N1) and 584 (N2), and the interface tubes are connected with the shunt. With the shunt in place, the terg tank 559 is pressurized by the second pump 532 (pump #0) with valves 561 (V4b) and 563 (V2b) open and valves 557 (V4a) and 533 (V3a) closed to flush the cleaning solution back through the interface tubes 582 (N1) and 584 (N2) and into the waste bladder 554. Subsequently, saline can be drawn from the saline bag 520 for a saline flush. This flush pushes saline through the Hb sensor tube 528 (T4), the anticoagulant valve tube 534 (T3), the sample cell 548, and the waste tube 556 (T6). Thus, in some embodiments, the following valves are open for this flush: 529 (V7a), 533 (V3a), 557 (V4a), and the following valves are closed: 542 (PV1), 523 (V0), 531 (V1a), 566 (V3b), 563 (V2b), and 561 (V4b).

Following analysis, the second pump 532 (pump #0) flushes the sample cell 548 and sends the flushed contents to the waste bladder 554. This flush can be done with a cleaning solution from the terg tank 558. In some embodiments, the terg tank valve 559 (V7b) is open, providing fluid communication between the second pump 532 and the terg tank 558. The second pump 532 forces cleaning solution from the terg tank 558 between the tube-flanking portions of the open pinch valve 561 and through the tube 562 (T7). The cleaning flush can pass through the sample cell 548, through the second connector 546, through the tube 564 (T5) and the open valve 563 (V2b), and into the waste bladder 554.

Subsequently, the first pump 522 (pump #1) can flush the cleaning solution out of the sample cell 548 using saline in drawn from the saline bag 520. This flush pushes saline through the Hb sensor tube 528 (T4), the anticoagulant valve tube 534 (T3), the sample cell 548, and the waste tube 556 (T6). Thus, in some embodiments, the following valves are open for this flush: 529 (V7a), 533 (V3a), 557 (V4a), and the following valves are closed: 542 (PV1), 523 (V0), 531 (V1a), 566 (V3b), 563 (V2b), and 561 (V4b).

When the fluid source is a living entity such as a patient, a low flow of saline (e.g., 1-5 mL/hr) is preferably moved through the patient tube 512 (T1) and into the patient to keep the patient's vessel open (e.g., to establish a keep vessel open, or "KVO" flow). This KVO flow can be temporarily interrupted when fluid is drawn into the fluid system 510. The source of this KVO flow can be the infusion pump 518, the third pump 568 (pump #3), or the first pump 522 (pump #1). In some embodiments, the infusion pump 518 can run continuously throughout the measurement cycle described above. This continuous flow can advantageously avoid any alarms that may be triggered if the infusion pump 518 senses that the flow has stopped or changed in some other way. In some embodiments, when the infusion valve 521 closes to allow pump 522 (pump #1) to withdraw fluid from a fluid source (e.g., a patient), the third pump 568 (pump #3) can withdraw fluid through the connector 570, thus allowing the infusion pump 518 to continue pumping normally as if the fluid path was not blocked by the infusion valve 521. If the measurement cycle is about two minutes long, this withdrawal by the third pump 568 can continue for approximately two minutes. Once the infusion valve 521 is open again, the third pump 568 (pump #3) can reverse and insert the saline back into the system at a low flow rate. Preferably, the time between measurement cycles is longer than the measurement cycle itself (e.g., longer than two minutes). Accordingly, the third pump 568 can insert fluid back into the system at a lower rate than it withdrew that fluid. This can help prevent an alarm by the infusion pump.

Figure 6:
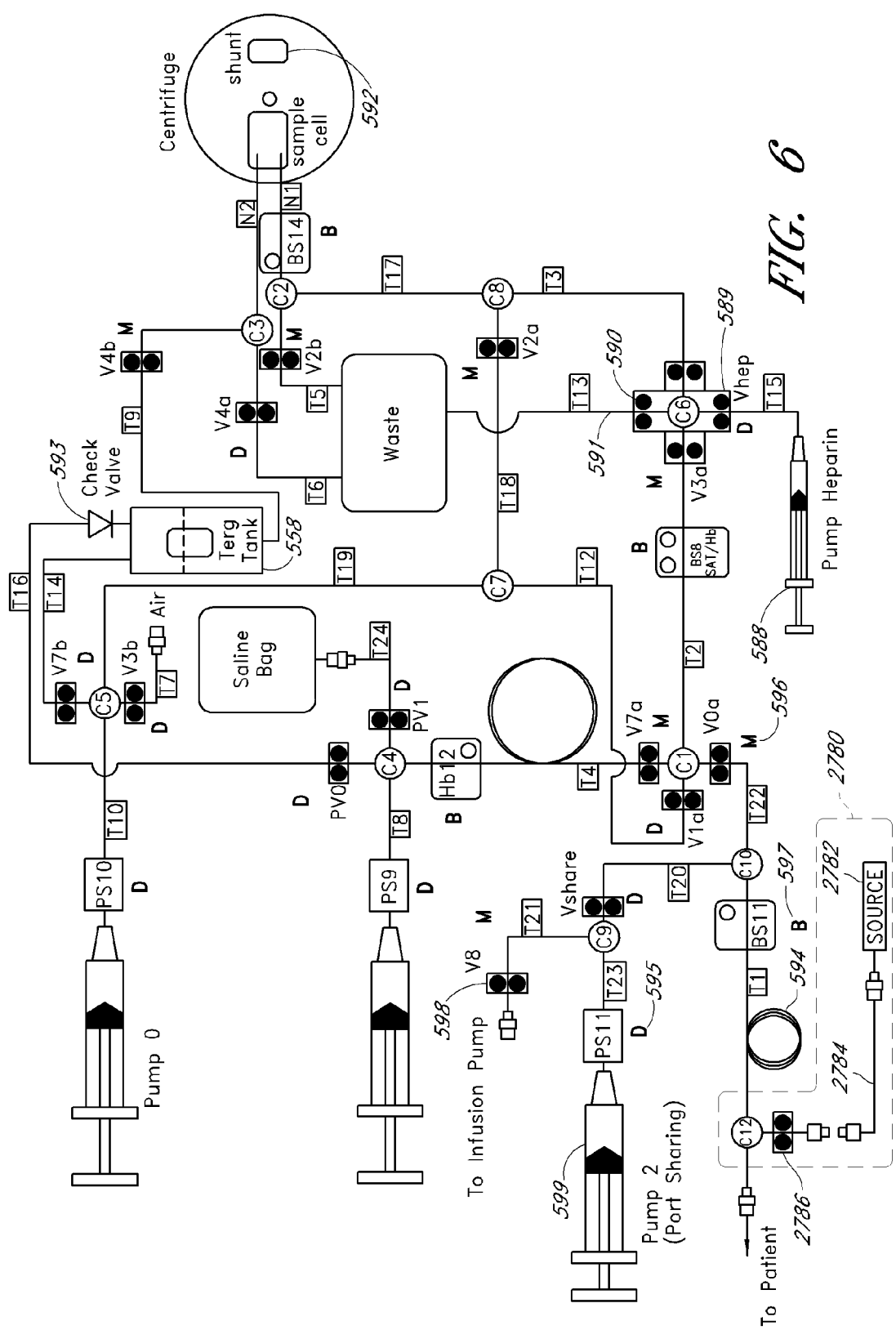
FIG. 6 schematically illustrates another embodiment of a fluid system that can be part of a system for withdrawing and analyzing fluid samples.

FIG. 6 schematically illustrates another embodiment of a fluid system that can be part of a system for withdrawing and analyzing fluid samples. In this embodiment, the anticoagulant valve 541 has been replaced with a syringe-style pump 588 (Pump Heparin) and a series of pinch valves around a junction between tubes. For example, a heparin pinch valve 589 (Vhep) can be closed to prevent flow from or to the pump 588, and a heparin waste pinch valve 590 can be closed to prevent flow from or to the waste container from this junction through the heparin waste tube 591. This embodiment also illustrates the shunt 592 schematically. Other differences from FIG. 5 include the check valve 593 located near the terg tank 558 and the patient loop 594. The reference letters D, for example, the one indicated at 595, refer to components that are advantageously located on the door. The reference letters M, for example, the one indicated at 596, refer to components that are advantageously located on the monitor. The reference letters B, for example, the one indicated at 597, refer to components that can be advantageously located on both the door and the monitor.

In some embodiments, the system 400 (see FIG. 4), the apparatus 100 (see FIG. 1), or even the monitoring device 102 (see FIG. 1) itself can also actively function not only to monitor analyte levels (e.g., glucose), but also to change and/or control analyte levels. Thus, the monitoring device 102 can be both a monitoring and an infusing device. In some embodiments, the fluid handling system 510 can include an optional analyte control subsystem 2780 that will be further described below (see discussion of analyte control).

In certain embodiments, analyte levels in a patient can be adjusted directly (e.g., by infusing or extracting glucose) or indirectly (e.g., by infusing or extracting insulin). FIG. 6 illustrates one way of providing this function. The infusion pinch valve 598 (V8) can allow the port sharing pump 599 (compare to the third pump 568 (pump #3) in FIG. 5) to serve two roles. In the first role, it can serve as a "port sharing" pump. The port sharing function is described with respect to the third pump 568 (pump #3) of FIG. 5, where the third pump 568 (pump #3) can withdraw fluid through the connector 570, thus allowing the infusion pump 518 to continue pumping normally as if the fluid path was not blocked by the infusion valve 521. In the second role, the port sharing pump 599 can serve as an infusion pump. The infusion pump role allows the port sharing pump 599 to draw a substance (e.g., glucose, saline, etc.) from another source when the infusion pinch valve 598 is open, and then to infuse that substance into the system or the patient when the infusion pinch valve 598 is closed. This can occur, for example, in order to change the level of a substance in a patient in response to a reading by the monitor that the substance is too low. In some embodiments, one or more of the pumps may comprise a reversible infusion pump configured to interrupt the flow of the infusion fluid and draw a sample of blood for analysis.

Mechanical/Fluid System Interface

Figure 7:
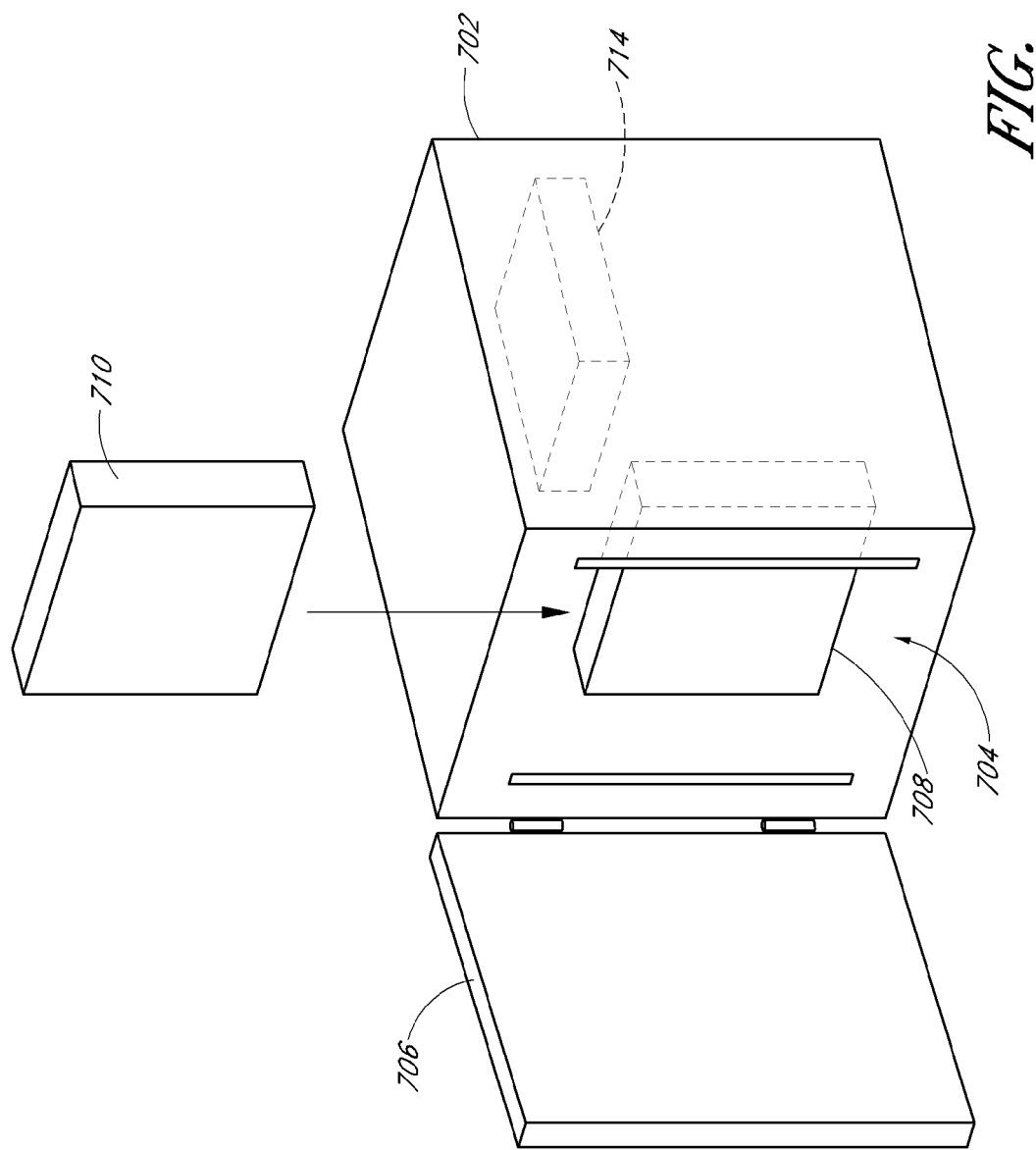
FIG. 7 is an oblique schematic depiction of an embodiment of a monitoring device.

FIG. 7 is an oblique schematic depiction of a modular monitoring device 700, which can correspond to the monitoring device 102. The modular monitoring device 700 includes a body portion 702 having a receptacle 704, which can be accessed by moving a movable portion 706. The receptacle 704 can include connectors (e.g., rails, slots, protrusions, resting surfaces, etc.) with which a removable portion 710 can interface. In some embodiments, portions of a fluidic system that directly contact fluid are incorporated into one or more removable portions (e.g., one or more disposable cassettes, sample holders, tubing cards, etc.). For example, a removable portion 710 can house at least a portion of the fluid system 510 described previously, including portions that contact sample fluids, saline, detergent solution, and/or anticoagulant.

In some embodiments, a non-disposable fluid-handling subsystem 708 is disposed within the body portion 702 of the monitoring device 700. The first removable portion 710 can include one or more openings that allow portions of the non-disposable fluid-handling subsystem 708 to interface with the removable portion 710. For example, the non-disposable fluid-handling subsystem 708 can include one or more pinch valves that are designed to extend through such openings to engage one or more sections of tubing. When the first removable portion 710 is present in a corresponding first receptacle 704, actuation of the pinch valves can selectively close sections of tubing within the removable portion. The non-disposable fluid-handling subsystem 708 can also include one or more sensors that interface with connectors, tubing sections, or pumps located within the first removable portion 710. The non-disposable fluid-handling subsystem 708 can also include one or more actuators (e.g., motors) that can actuate moveable portions (e.g., the plunger of a syringe) that may be located in the removable portion F10. A portion of the non-disposable fluid-handling subsystem 708 can be located on or in the moveable portion F06 (which can be a door having a slide or a hinge, a detachable face portion, etc.).

In the embodiment shown in FIG. 7, the monitoring device 700 includes an optical system 714 disposed within the body portion 702. The optical system 714 can include a light source and a detector that are adapted to perform measurements on fluids within a sample holder (not shown). The light source may comprise a fixed wavelength light source and/or a tunable light source. The light source may comprise one or more sources including, for example, broadband sources, LEDs, and lasers. In some embodiments, the sample holder comprises a removable portion, which can be associated with or disassociated from the removable portion F10. The sample holder can include an optical window through which the optical system 714 can emit radiation for measuring properties of a fluid in the sample holder. The optical system 714 can include other components such as, for example, a power supply, a centrifuge motor, a filter wheel, and/or a beam splitter.

In some embodiments, the removable portion 710 and the sample holder are adapted to be in fluid communication with each other. For example, the removable portion 710 can include a retractable injector that injects fluids into a sample holder. In some embodiments, the sample holder can comprise or be disposed in a second removable portion (not shown). In some embodiments, the injector can be retracted to allow the centrifuge to rotate the sample holder freely.

The body portion 702 of the monitoring device 700 can also include one or more connectors for an external battery (not shown). The external battery can serve as a backup emergency power source in the event that a primary emergency power source such as, for example, an internal battery (not shown) is exhausted.

FIG. 7 shows an embodiment of a system having subcomponents illustrated schematically. By way of a more detailed (but nevertheless non-limiting) example, FIG. 8 and FIG. 9 show more details of the shape and physical configuration of a sample embodiment.

Figure 8:
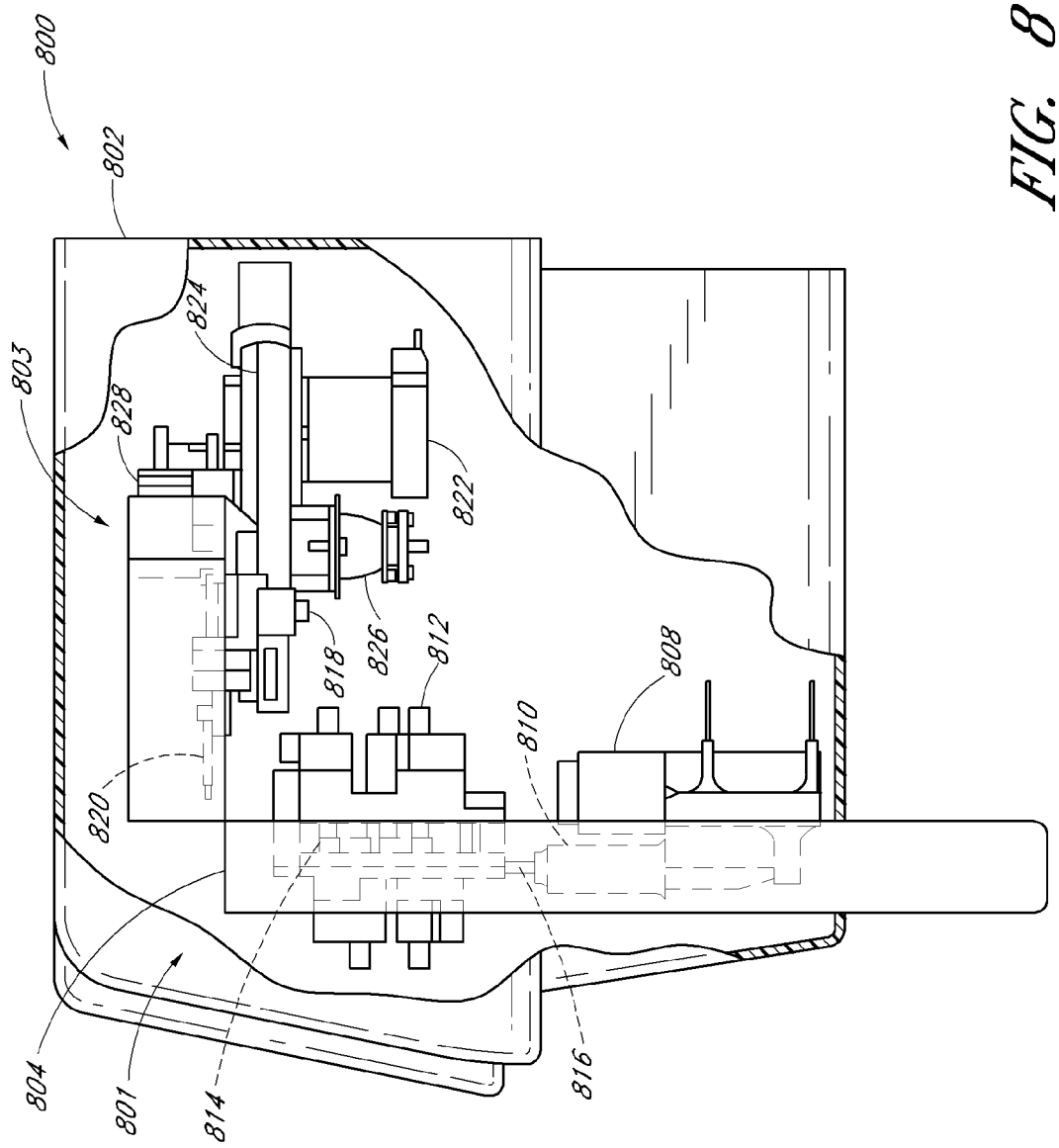
FIG. 8 shows a cut-away side view of an embodiment of a monitoring device.
Figure 9:
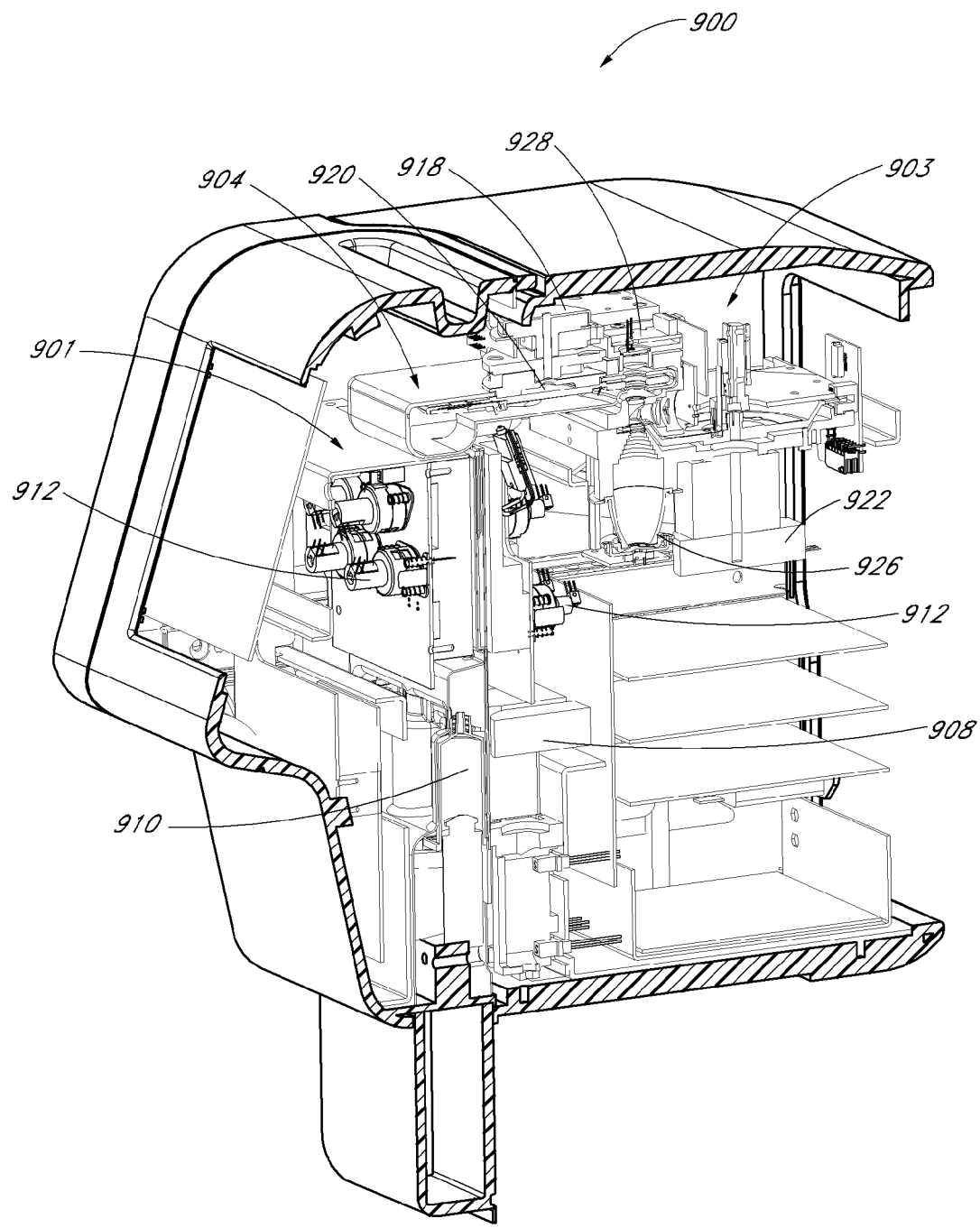
FIG. 9 shows a cut-away perspective view of an embodiment of a monitoring device.

FIG. 8 shows a cut-away side view of a monitoring device 800 (which can correspond, for example, to the device 102 shown in FIG. 1). The device 800 includes a casing 802. The monitoring device 800 can have a fluid system. For example, the fluid system can have subsystems, and a portion or portions thereof can be disposable, as schematically depicted in FIG. 4. As depicted in FIG. 8, the fluid system is generally located at the left-hand portion of the casing 802, as indicated by the reference 801. The monitoring device 800 can also have an optical system. In the illustrated embodiment, the optical system is generally located in the upper portion of the casing 802, as indicated by the reference 803. Advantageously, however, the fluid system 801 and the optical system 803 can both be integrated together such that fluid flows generally through a portion of the optical system 803, and such that radiation flows generally through a portion of the fluid system 801.

Depicted in FIG. 8 are examples of ways in which components of the device 800 mounted within the casing 802 can interface with components of the device 800 that comprise disposable portions. Not all components of the device 800 are shown in FIG. 8. A disposable portion 804 having a variety of components is shown in the casing 802. In some embodiments, one or more actuators 808 housed within the casing 802, operate syringe bodies 810 located within a disposable portion 804. The syringe bodies 810 are connected to sections of tubing 816 that move fluid among various components of the system. The movement of fluid is at least partially controlled by the action of one or more pinch valves 812 positioned within the casing 802. The pinch valves 812 have arms 814 that extend within the disposable portion 804. Movement of the arms 814 can constrict a section of tubing 816.

In some embodiments, a sample cell holder 820 can engage a centrifuge motor 818 mounted within the casing 802 of the device 800. A filter wheel motor 822 disposed within the housing 802 rotates a filter wheel 824, and in some embodiments, aligns one or more filters with an optical path. An optical path can originate at a source 826 within the housing 802 that can be configured to emit a beam of radiation (e.g., infrared radiation, visible radiation, ultraviolet radiation, etc.) through the filter and the sample cell holder 820 and to a detector 828. A detector 828 can measure the optical density of the light when it reaches the detector.

FIG. 9 shows a cut-away perspective view of an alternative embodiment of a monitoring device 900. Many features similar to those illustrated in FIG. 8 are depicted in this illustration of an alternative embodiment. A fluid system 901 can be partially seen. The disposable portion 904 is shown in an operative position within the device. One of the actuators 808 can be seen next to a syringe body 910 that is located within the disposable portion 904. Some pinch valves 912 are shown next to a fluid-handling portion of the disposable portion 904. In this figure, an optical system 903 can also be partially seen. The sample holder 920 is located underneath the centrifuge motor 918. The filter wheel motor 922 is positioned near the radiation source 926, and the detector 928 is also illustrated.

FIG. 10 illustrates two views of a disposable cartridge 1000 that can interface with a fluid system such as the fluid system 510 of FIG. 5. The disposable cartridge 1000 can be configured for insertion into a receptacle of the device 800 of FIG. 8 and/or the device 900 shown in FIG. 9. The disposable cartridge 1000 can fill the role of the removable portion 710 of FIG. 7, for example. In some embodiments, the disposable cartridge 1000 can be used for a system having only one disposable subsystem, making it a simple matter for a health care provider to replace and/or track usage time of the disposable portion. In some embodiments, the cartridge 1000 includes one or more features that facilitate insertion of the cartridge 1000 into a corresponding receptacle. For example, the cartridge 1000 can be shaped so as to promote insertion of the cartridge 1000 in the correct orientation. The cartridge 1000 can also include labeling or coloring affixed to or integrated with the cartridge's exterior casing that help a handler insert the cartridge 1000 into a receptacle properly.

The cartridge 1000 can include one or more ports for connecting to material sources or receptacles. Such ports can be provided to connect to, for example, a saline source, an infusion pump, a sample source, and/or a source of gas (e.g., air, nitrogen, etc.). The ports can be connected to sections of tubing within the cartridge 1000. In some embodiments, the sections of tubing are opaque or covered so that fluids within the tubing cannot be seen, and in some embodiments, sections of tubing are transparent to allow interior contents (e.g., fluid) to be seen from outside.

Figure 15:
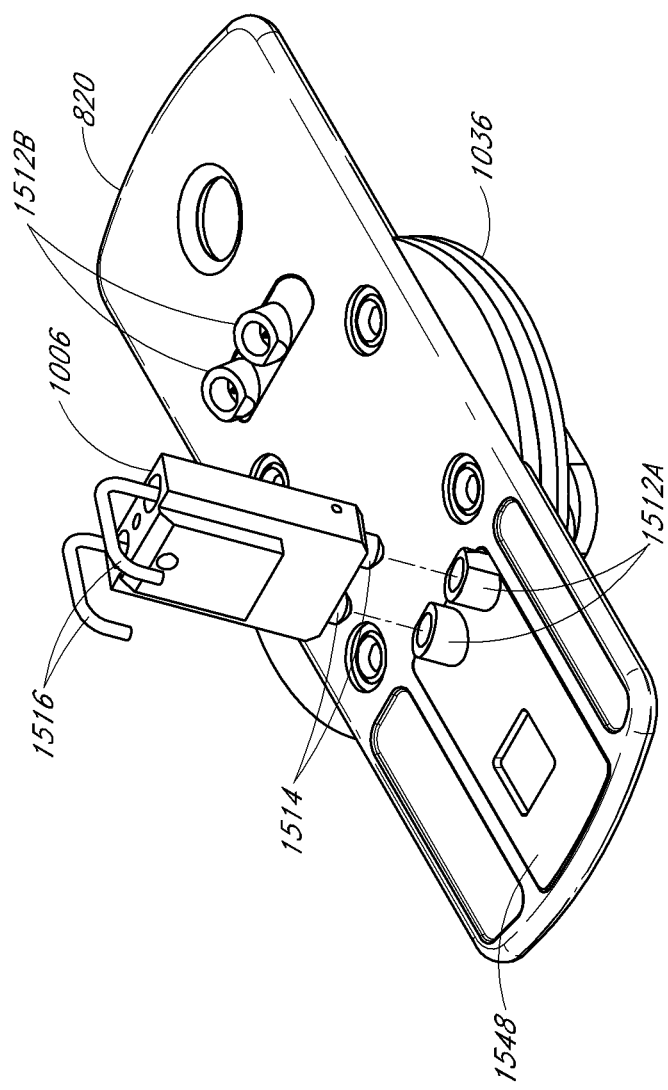
FIG. 15 shows an underneath perspective view of a sample cell holder attached to a centrifuge interface, with a view of an interface with a sample injector.

The cartridge 1000 shown in FIG. 10 can include a sample injector 1006. The sample injector 1006 can be configured to inject at least a portion of a sample into a sample holder (see, e.g., the sample cell 548), which can also be incorporated into the cartridge 1000. The sample injector 1006 can include, for example, the sample cell holder interface tubes 582 (N1) and 584 (N2) of FIG. 5, embodiments of which are also illustrated in FIG. 15.

The housing of the cartridge 1000 can include a tubing portion 1008 containing within it a card having one or more sections of tubing. In some embodiments, the body of the cartridge 1000 includes one or more apertures 1009 through which various components, such as, for example, pinch valves and sensors, can interface with the fluid-handling portion contained in the cartridge 1000. The sections of tubing found in the tubing portion 1008 can be aligned with the apertures 1009 in order to implement at least some of the functionality shown in the fluid system 510 of FIG. 5.

The cartridge 1000 can include a pouch space (not shown) that can comprise one or more components of the fluid system 510. For example, one or more pouches and/or bladders can be disposed in the pouch space (not shown). In some embodiments, a cleaner pouch and/or a waste bladder can be housed in a pouch space. The waste bladder can be placed under the cleaner pouch such that, as detergent is removed from the cleaner pouch, the waste bladder has more room to fill. The components placed in the pouch space (not shown) can also be placed side-by-side or in any other suitable configuration.

The cartridge 1000 can include one or more pumps 1016 that facilitate movement of fluid within the fluid system 510. Each of the pump housings 1016 can contain, for example, a syringe pump having a plunger. The plunger can be configured to interface with an actuator outside the cartridge 1000. For example, a portion of the pump that interfaces with an actuator can be exposed to the exterior of the cartridge 1000 housing by one or more apertures 1018 in the housing.

The cartridge 1000 can have an optical interface portion 1030 that is configured to interface with (or comprise a portion of) an optical system. In the illustrated embodiment, the optical interface portion 1030 can pivot around a pivot structure 1032. The optical interface portion 1030 can house a sample holder (not shown) in a chamber that can allow the sample holder to rotate. The sample holder can be held by a centrifuge interface 1036 that can be configured to engage a centrifuge motor (not shown). When the cartridge 1000 is being inserted into a system, the orientation of the optical interface portion 1030 can be different than when it is functioning within the system.

In some embodiments, the disposable cartridge 1000 is designed for single patient use. The cartridge 1000 may also be designed for replacement after a period of operation. For example, in some embodiments, if the cartridge 1000 is installed in a continuously operating monitoring device that performs four measurements per hour, the waste bladder may become filled or the detergent in the cleaner pouch depleted after about three days. The cartridge 1000 can be replaced before the detergent and waste bladder are exhausted.

The cartridge 1000 can be configured for easy replacement. For example, in some embodiments, the cartridge 1000 is designed to have an installation time of only several minutes. For example, the cartridge can be designed to be installed in less than about five minutes. During installation, various fluid lines contained in the cartridge 1000 can be primed by automatically filling the fluid lines with saline. The saline can be mixed with detergent powder from the cleaner pouch in order to create a cleaning solution.

The cartridge 1000 can also be designed to have a relatively brief shut down time. For example, the shut down process can be configured to take less than about five minutes. The shut down process can include flushing the patient line; sealing off the insulin pump connection, the saline source connection, and the sample source connection; and taking other steps to decrease the risk that fluids within the used cartridge 1000 will leak after disconnection from the monitoring device.

Some embodiments of the cartridge 1000 can comprise a flat package to facilitate packaging, shipping, sterilizing, etc. Advantageously, however, some embodiments can further comprise a hinge or other pivot structure. Thus, as illustrated, an optical interface portion 1030 can be pivoted around a pivot structure 1032 to generally align with the other portions of the cartridge 1000. The cartridge can be provided to a medical provider sealed in a removable wrapper, for example.

In some embodiments, the cartridge 1000 is designed to fit within standard waste containers found in a hospital, such as a standard biohazard container. For example, the cartridge 1000 can be less than one foot long, less than one foot wide, and less than two inches thick. In some embodiments, the cartridge 1000 is designed to withstand a substantial impact, such as that caused by hitting the ground after a four foot drop, without damage to the housing or internal components. In some embodiments, the cartridge 1000 is designed to withstand significant clamping force applied to its casing. For example, the cartridge 1000 can be built to withstand five pounds per square inch of force without damage. In some embodiments, the cartridge 1000 is non pyrogenic and/or latex free.

Figure 11:
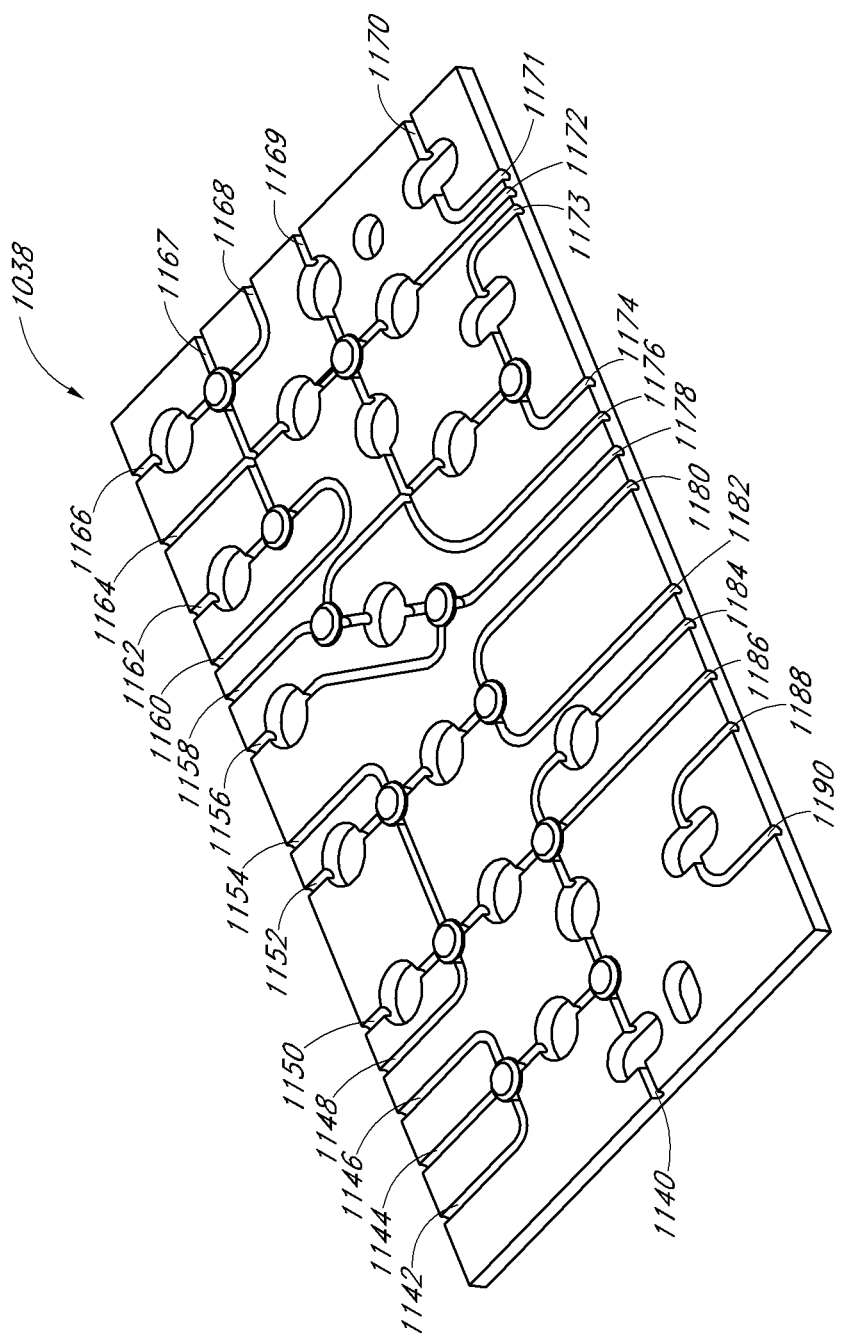
FIG. 11 illustrates an embodiment of a fluid routing card that can be part of the removable cartridge of FIG. 10.

FIG. 11 illustrates an embodiment of a fluid-routing card 1038 that can be part of the removable cartridge of FIG. 10. For example, the fluid-routing card 1038 can be located generally within the tubing portion 1008 of the cartridge 1000. The fluid-routing card 1038 can contain various passages and/or tubes through which fluid can flow as described with respect to FIG. 5 and/or FIG. 6, for example. Thus, the illustrated tube opening openings can be in fluid communication with the following fluidic components, for example:

| Tube Opening Reference Numeral | Can Be In Fluid Communication With |
| --- | --- |
| 1142 | third pump 568 (pump #3) |
| 1144 | infusion pump 518 |
| 1146 | presx |
| 1148 | air pump |
| 1150 | vent |
| 1152 | detergent (e.g., tergazyme) source or waste tube |
| 1154 | presx |
| 1156 | detergent (e.g., tergazyme) source or waste tube |
| 1158 | waste receptacle |
| 1160 | first pump 522 (pump #1) (e.g., a saline pump) |
| 1162 | saline source or waste tube |
| 1164 | anticoagulant (e.g., heparin) pump (see FIG. 6) and/or shuttle valve |
| 1166 | detergent (e.g., tergazyme) source or waste tube |
| 1167 | presx |
| 1168 | Hb sensor tube 528 (T4) |
| 1169 | tube 536 (T2) |
| 1170 | Hb sensor tube 528 (T4) |
| 1171 | Hb sensor tube 528 (T4) |
| 1172 | anticoagulant (e.g., heparin) pump |
| 1173 | T17 (see FIG. 6) |
| 1174 | Sample cell holder interface tube 582 (N1) |
| 1176 | anticoagulant valve tube 534 (T3) |
| 1178 | Sample cell holder interface tube 584 (N2) |
| 1180 | T17 (see FIG. 6) |
| 1182 | anticoagulant valve tube 534 (T3) |
| 1184 | Hb sensor tube 528 (T4) |
| 1186 | tube 536 (T2) |
| 1188 | anticoagulant valve tube 534 (T3) |
| 1190 | anticoagulant valve tube 534 (T3) |

The depicted fluid-routing card 1038 can have additional openings that allow operative portions of actuators and/or valves to protrude through the fluid-routing card 1038 and interface with the tubes.

Figure 12:
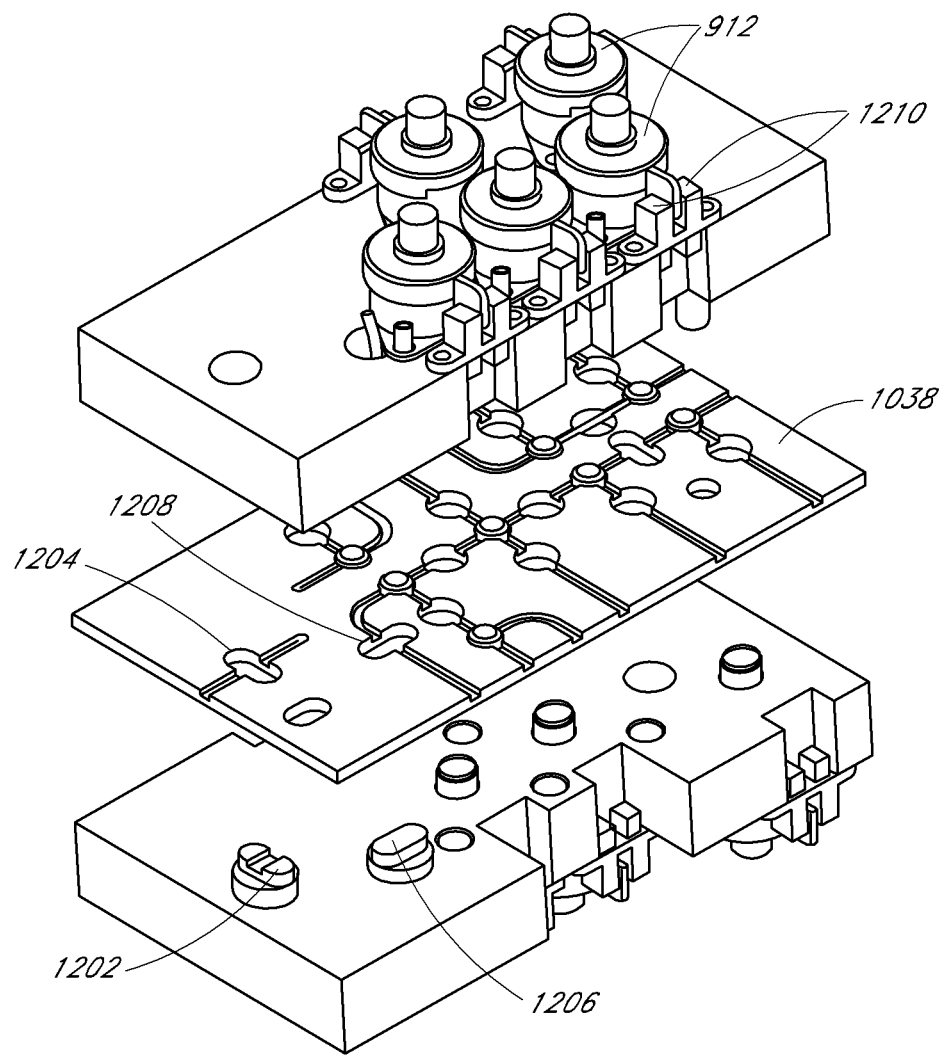
FIG. 12 illustrates how non-disposable actuators can interface with the fluid routing card of FIG. 11.

FIG. 12 illustrates how actuators, which can sandwich the fluid-routing card 1038 between them, can interface with the fluid-routing card 1038 of FIG. 11. Pinch valves 812 can have an actuator portion that protrudes away from the fluid-routing card 1038 containing a motor. Each motor can correspond to a pinch platen 1202, which can be inserted into a pinch platen receiving hole 1204. Similarly, sensors, such as a bubble sensor 1206 can be inserted into receiving holes (e.g., the bubble sensor receiving hole 1208). Movement of the pinch valves 812 can be detected by the position sensors 1210.

Figure 13:
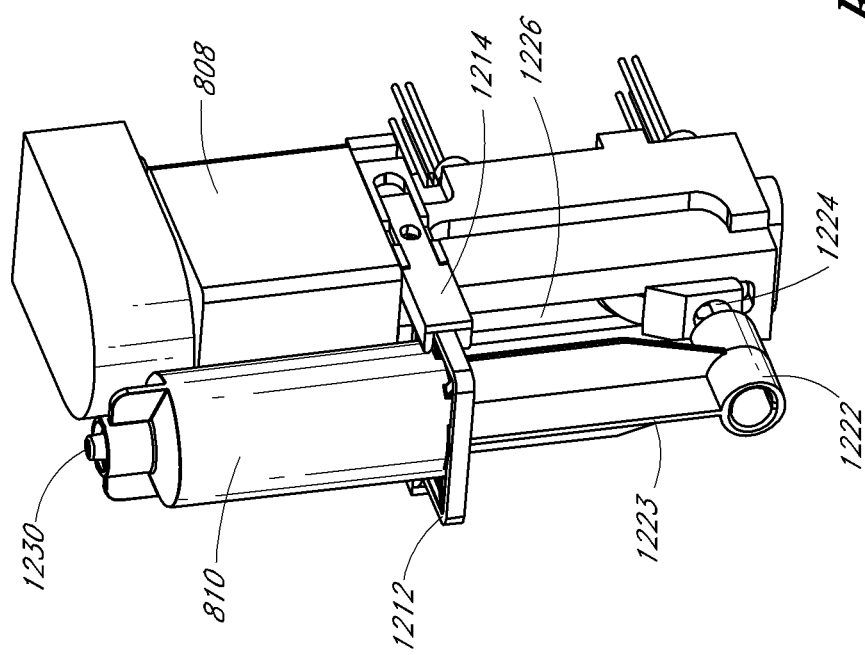
FIG. 13 illustrates a modular pump actuator connected to a syringe housing that can form a portion of a removable cartridge.

FIG. 13 illustrates an actuator 808 that is connected to a corresponding syringe body 810. The actuator 808 is an example of one of the actuators 808 that is illustrated in FIG. 8 and in FIG. 9, and the syringe body 810 is an example of one of the syringe bodies 810 that are visible in FIG. 8 and in FIG. 9. A ledge portion 1212 of the syringe body 810 can be engaged (e.g., slid into) a corresponding receiving portion 1214 in the actuator 808. In some embodiments, the receiving portion 1214 can slide outward to engage the stationary ledge portion 1212 after the disposable cartridge 804 is in place. Similarly, a receiving tube 1222 in the syringe plunger 1223 can be slide onto (or can receive) a protruding portion 1224 of the actuator 808. The protruding portion 1224 can slide along a track 1226 under the influence of a motor inside the actuator 808, thus actuating the syringe plunger 1223 and causing fluid to flow into or out of the syringe tip 1230.

Figure 14:
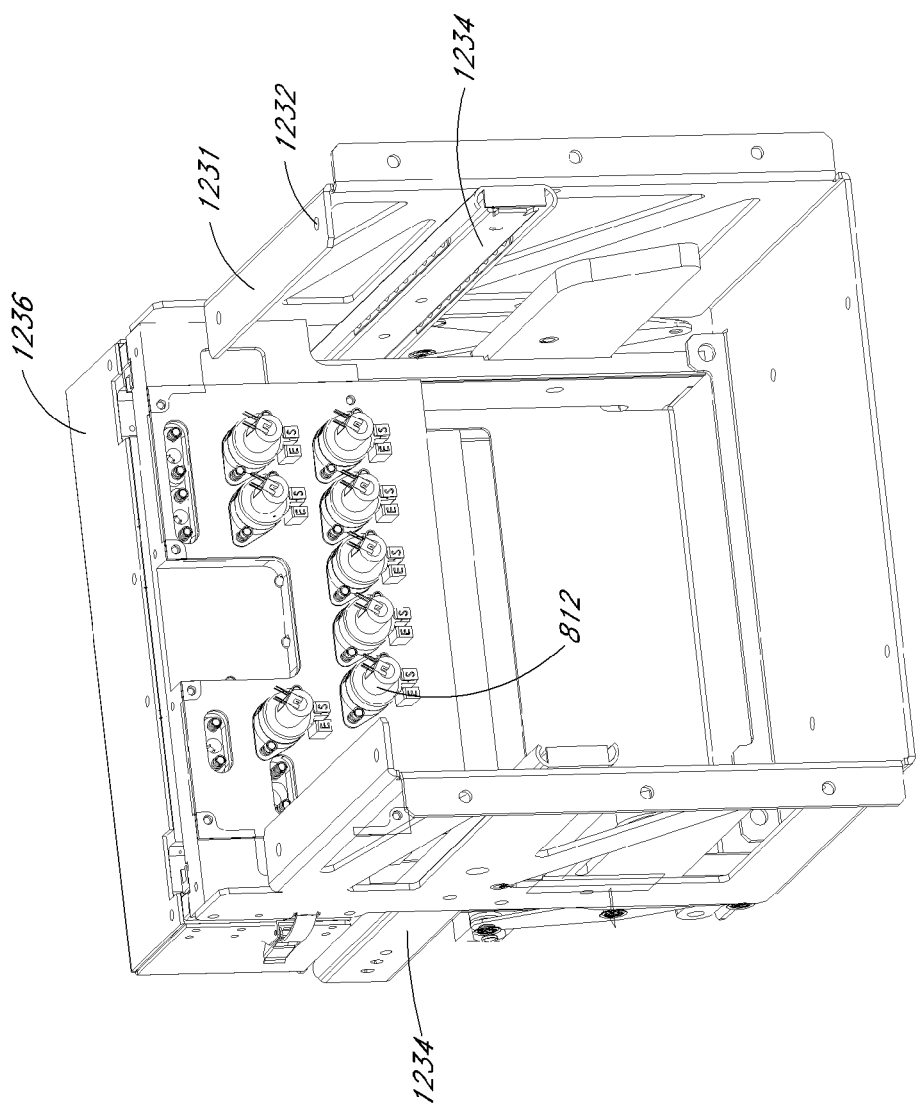
FIG. 14 shows a rear perspective view of internal scaffolding and some pinch valve pump bodies.

FIG. 14 shows a rear perspective view of internal scaffolding 1231 and the protruding bodies of some pinch valves 812. The internal scaffolding 1231 can be formed from metal and can provide structural rigidity and support for other components. The scaffolding 1231 can have holes 1232 into which screws can be screwed or other connectors can be inserted. In some embodiments, a pair of sliding rails 1234 can allow relative movement between portions of an analyzer. For example, a slidable portion 1236 (which can correspond to the movable portion 706, for example) can be temporarily slid away from the scaffolding 1231 of a main unit in order to allow an insertable portion (e.g., the cartridge 804) to be inserted.

FIG. 15 shows an underneath perspective view of the sample cell holder 820, which is attached to the centrifuge interface 1036. The sample cell holder 820 can have an opposite side (see FIG. 17) that allows it to slide into a receiving portion of the centrifuge interface 1036. The sample cell holder 820 can also have receiving nubs 1512A that provide a pathway into a sample cell 1548 held by the sample cell holder 820. Receiving nubs 1512B can provide access to a shunt 1586 (see FIG. 16) inside the sample cell holder 820. The receiving nubs 1512A and 1512B can receive and or dock with fluid nipples 1514. The fluid nipples 1514 can protrude at an angle from the sample injector 1006, which can in turn protrude from the cartridge 1000 (see FIG. 10). The tubes 1516 shown protruding from the other end of the sample injector 1006 can be in fluid communication with the sample cell holder interface tubes 582 (N1) and 584 (N2) (see FIG. 5 and FIG. 6), as well as 1074 and 1078 (see FIG. 11).

Figure 16:
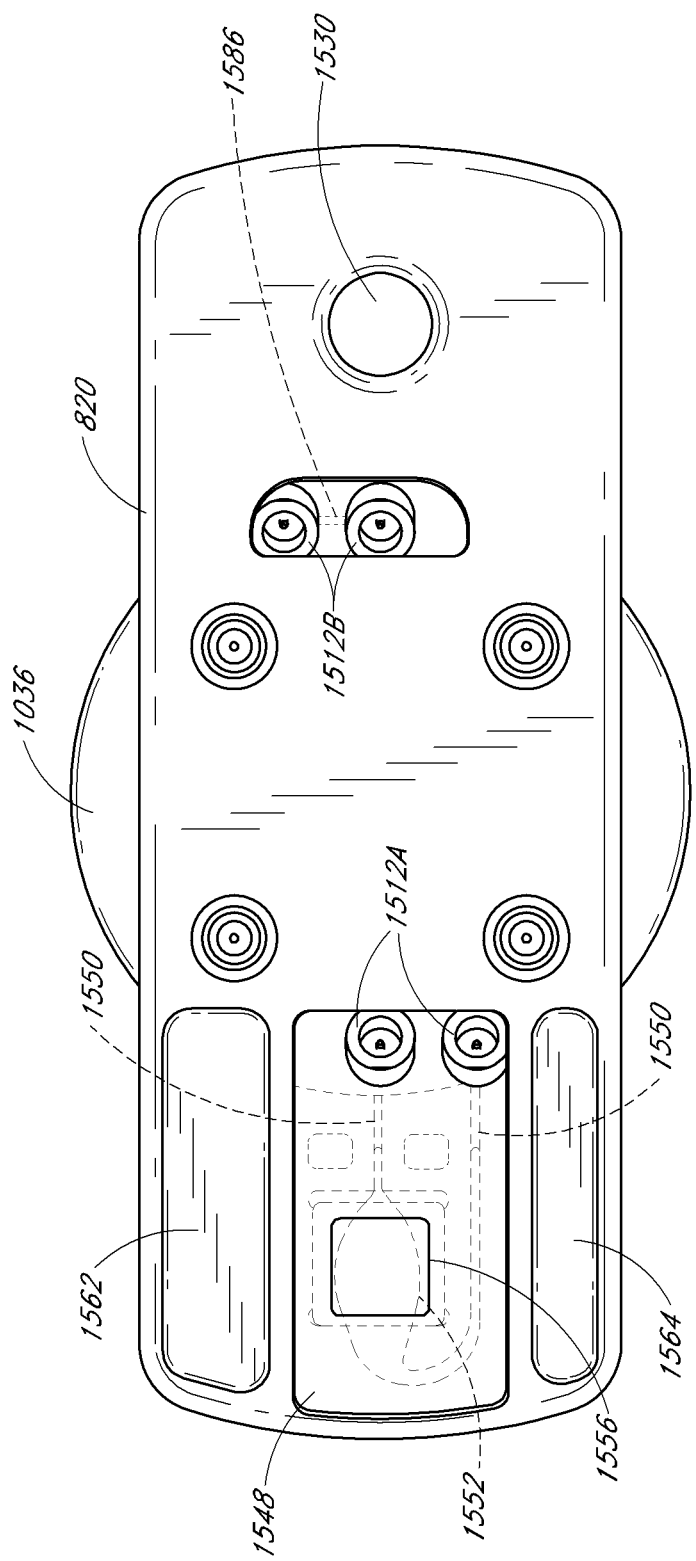
FIG. 16 shows a plan view of a sample cell holder with hidden and/or non-surface portions illustrated using dashed lines.

FIG. 16 shows a plan view of the sample cell holder 820 with hidden and/or non-surface portions illustrated using dashed lines. The receiving nubs 1512A communicate with passages 1550 inside the sample cell 1548 (which can correspond, for example to the sample cell 548 of FIG. 5). The passages widen out into a wider portion 1552 that corresponds to a window 1556. The window 1556 and the wider portion 1552 can be configured to house the sample when radiation is emitted along a pathlength that is generally non-parallel to the sample cell 1548. The window 1556 can allow calibration of the instrument with the sample cell 1548 in place, even before a sample has arrived in the wider portion 1552.

An opposite opening 1530 can provide an alternative optical pathway between a radiation source and a radiation detector (e.g., the radiation source 826 of FIG. 18) and may be used, for example, for obtaining a calibration measurement of the source and detector without an intervening window or sample. Thus, the opposite opening 1530 can be located generally at the same radial distance from the axis of rotation as the window 1556.

The receiving nubs 1512B communicate with a shunt passage 1586 inside the sample cell holder 820 (which can correspond, for example, to the shunt 586 of FIG. 5).

Other features of the sample cell holder 820 can provide balancing properties for even rotation of the sample cell holder 820. For example, the wide trough 1562 and the narrower trough 1564 can be sized or otherwise configured so that the weight and/or mass of the sample cell holder 820 is evenly distributed from left to right in the view of FIG. 16, and/or from top to bottom in this view of FIG. 16.

Figure 17:
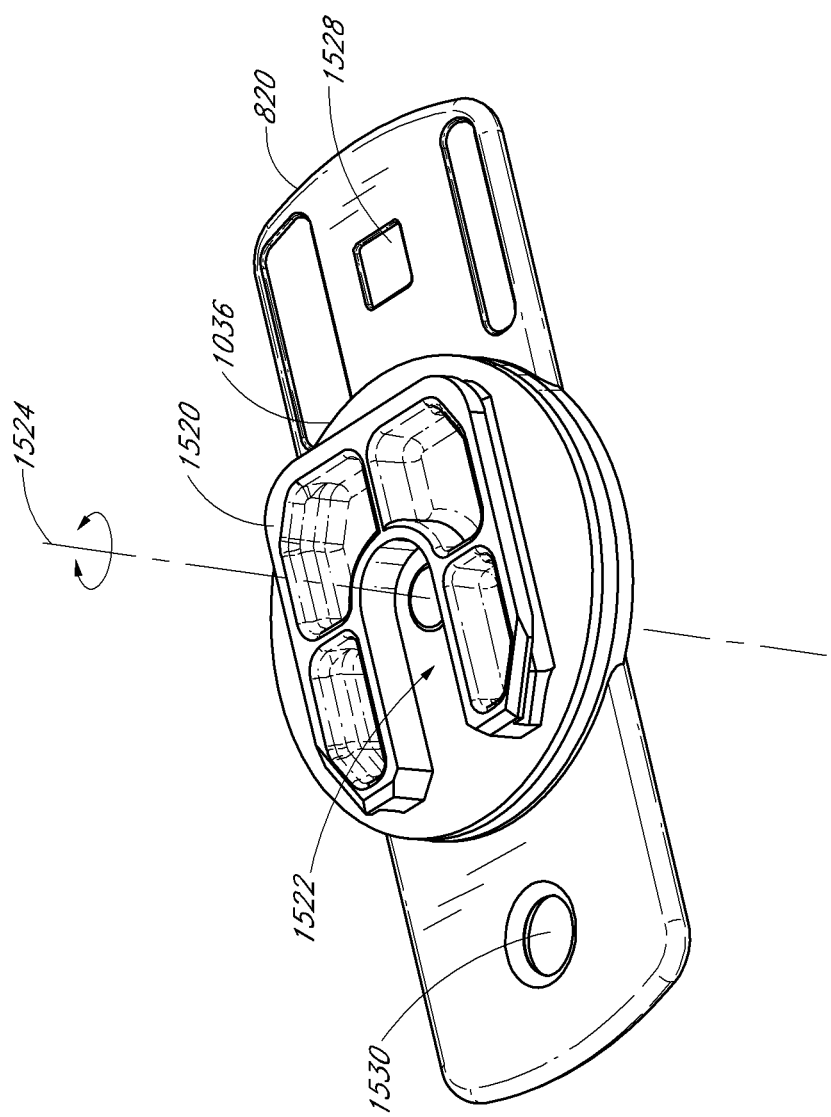
FIG. 17 shows a top perspective view of the centrifuge interface connected to the sample holder.

FIG. 17 shows a top perspective view of the centrifuge interface 1036 connected to the sample cell holder 820. The centrifuge interface 1036 can have a bulkhead 1520 with a rounded slot 1522 into which an actuating portion of a centrifuge can be slid from the side. The centrifuge interface 1036 can thus be spun about an axis 1524, along with the sample cell holder 820, causing fluid (e.g., whole blood) within the sample cell 1548 to separate into concentric strata, according to relative density of the fluid components (e.g., plasma, red blood cells, buffy coat, etc.), within the sample cell 1548. The sample cell holder 820 can be transparent, or it can at least have transparent portions (e.g., the window 1556 and/or the opposite opening 1530) through which radiation can pass, and which can be aligned with an optical pathway between a radiation source and a radiation detector (see, e.g., FIG. 20). In addition, a round portion 1530 through centrifuge rotor 1520 provides an optical pathway between the radiation source and radiation detector and may be used, for example, for obtaining a calibration measurement of the source and detector without an intervening window or sample.

Figure 18:
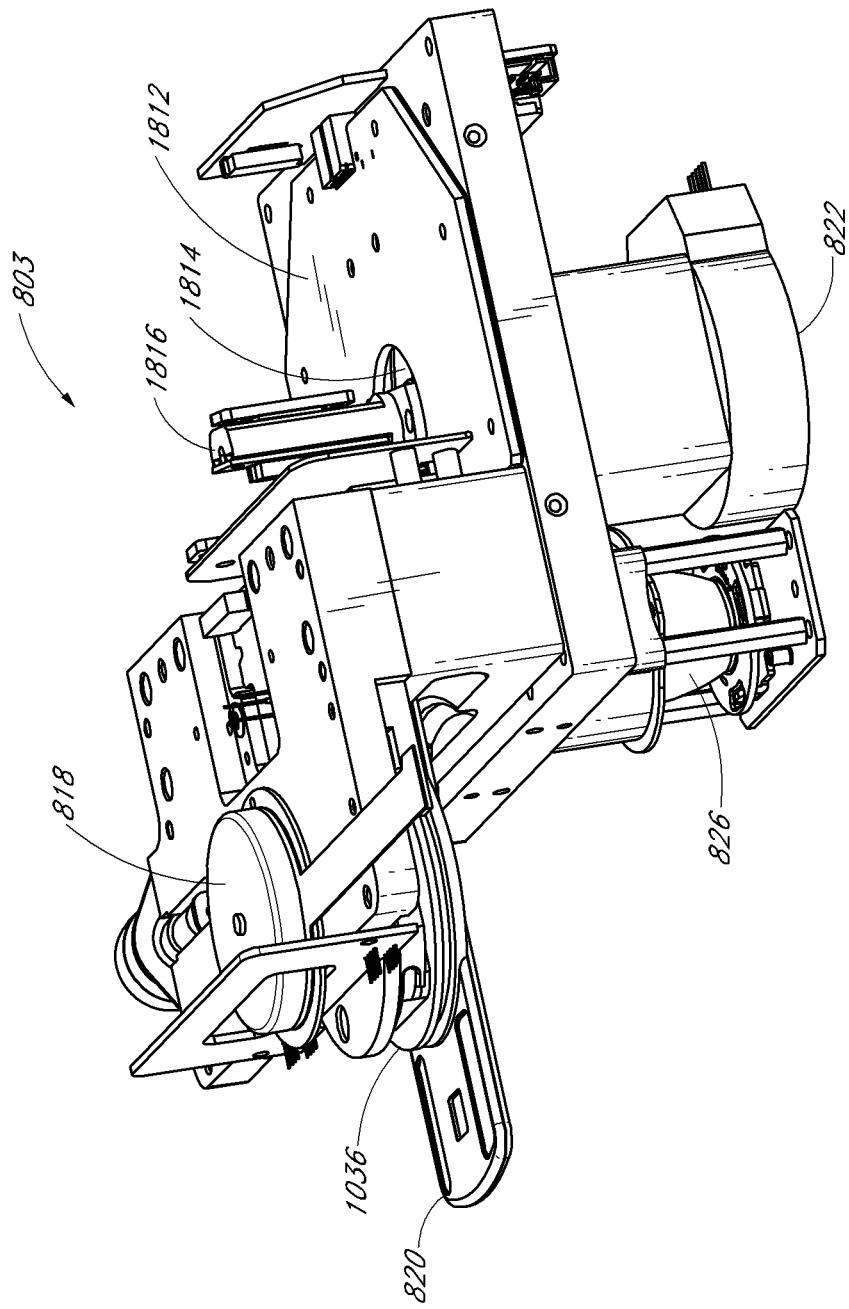
FIG. 18 shows a perspective view of an example optical system.

FIG. 18 shows a perspective view of an example optical system 803. Such a system can be integrated with other systems as shown in FIG. 9, for example. The optical system 803 can fill the role of the optical system 412, and it can be integrated with and/or adjacent to a fluid system (e.g., the fluid-handling system 404 or the fluid system 801). The sample cell holder 820 can be seen attached to the centrifuge interface 1036, which is in turn connected to, and rotatable by the centrifuge motor 818. A filter wheel housing 1812 is attached to the filter wheel motor 822 and encloses a filter wheel 1814. A protruding shaft assembly 1816 can be connected to the filter wheel 1814. The filter wheel 1814 can have multiple filters (see FIG. 19). The radiation source 826 is aligned to transmit radiation through a filter in the filter wheel 1814 and then through a portion of the sample cell holder 820. Transmitted and/or reflected and/or scattered radiation can then be detected by a radiation detector.

Figure 19:
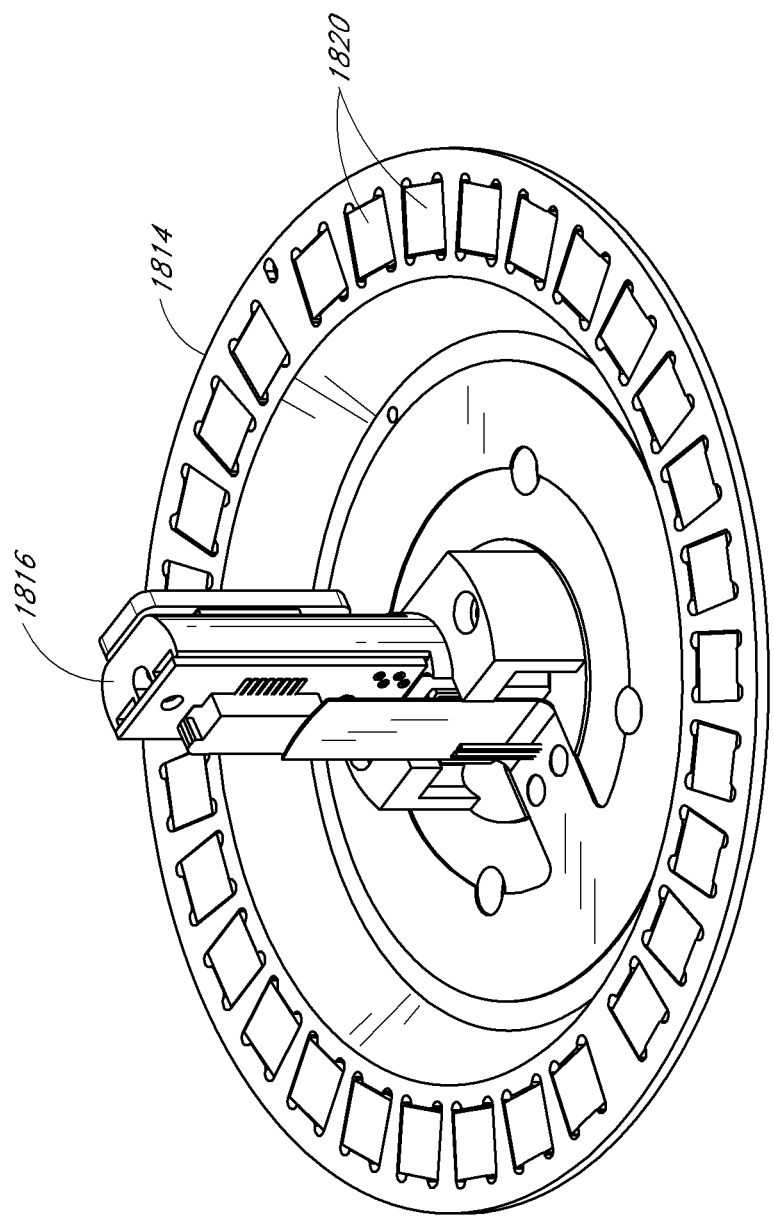
FIG. 19 shows a filter wheel that can be part of the optical system of FIG. 18.

FIG. 19 shows a view of the filter wheel 1814 when it is not located within the filter wheel housing 1812 of the optical system 803. Additional features of the protruding shaft assembly 1816 can be seen, along with multiple filters 1820. In some embodiments, the filters 1820 can be removably and/or replaceably inserted into the filter wheel 1814.

Spectroscopic System

As described above with reference to FIG. 4, the system 400 comprises the optical system 412 for analysis of a fluid sample. In various embodiments, the optical system 412 comprises one or more optical components including, for example, a spectrometer, a photometer, a reflectometer, or any other suitable device for measuring optical properties of the fluid sample. The optical system 412 may perform one or more optical measurements on the fluid sample including, for example, measurements of transmittance, absorbance, reflectance, scattering, and/or polarization. The optical measurements may be performed in one or more wavelength ranges including, for example, infrared (IR) and/or optical wavelengths. As described with reference to FIG. 4 (and further described below), the measurements from the optical system 412 are communicated to the algorithm processor 416 for analysis. For example, In some embodiments the algorithm processor 416 computes concentration of analyte(s) (and/or interferent(s)) of interest in the fluid sample. Analytes of interest include, e.g., glucose and lactate in whole blood or blood plasma.

Figure 20:
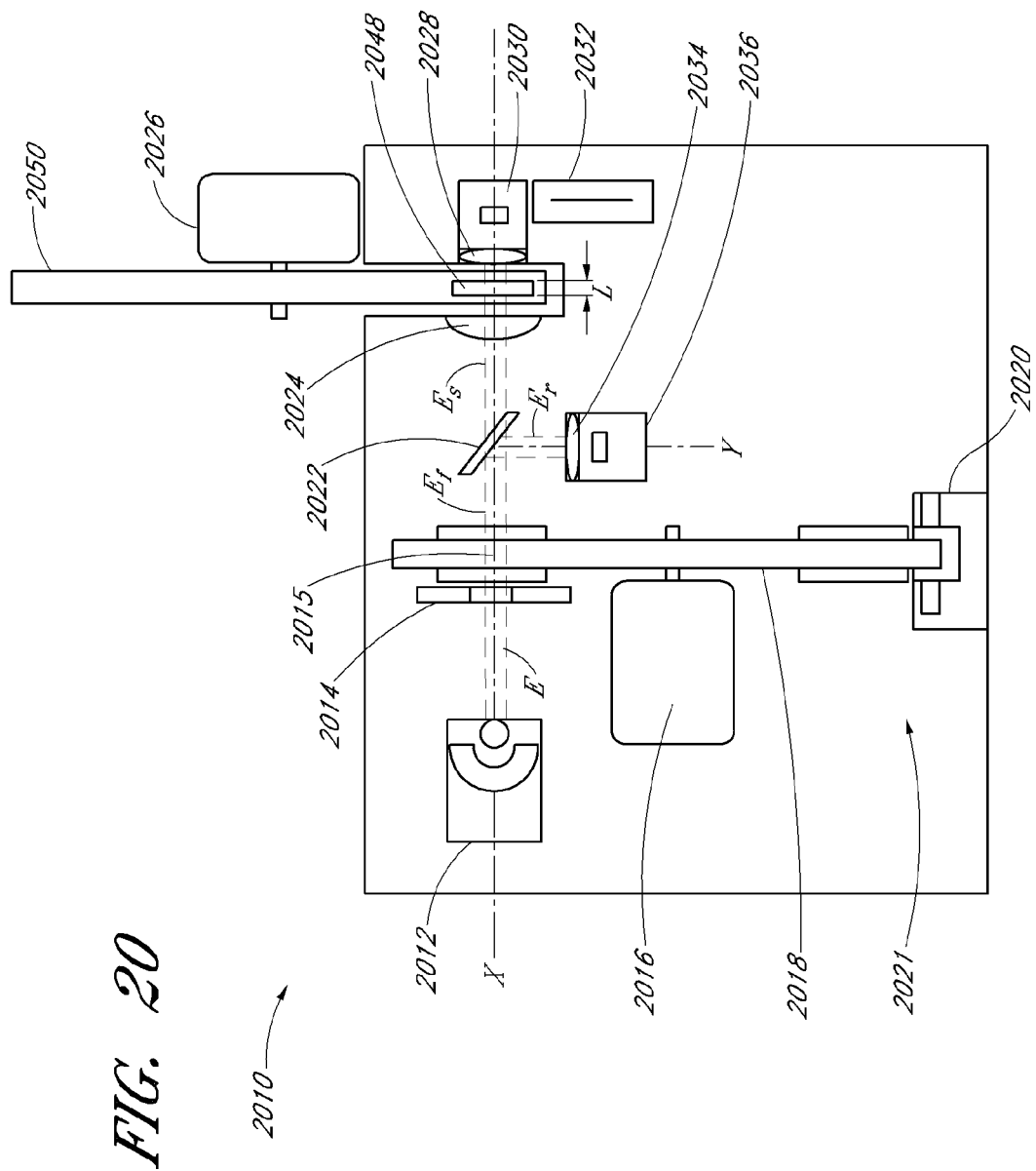
FIG. 20 schematically illustrates an embodiment of an optical system that comprises a spectroscopic analyzer adapted to measure spectra of a fluid sample.

FIG. 20 schematically illustrates an embodiment of the optical system 412 that comprises a spectroscopic analyzer 2010 adapted to measure spectra of a fluid sample such as, for example, blood or blood plasma. The analyzer 2010 comprises an energy source 2012 disposed along an optical axis X of the analyzer 2010. When activated, the energy source 2012 generates an electromagnetic energy beam E, which advances from the energy source 2012 along the optical axis X. In some embodiments, the energy source 2012 comprises an infrared energy source, and the energy beam E comprises an infrared beam. In some embodiments, the infrared energy beam E comprises a mid-infrared energy beam or a near-infrared energy beam. In some embodiments, the energy beam E can include optical and/or radio frequency wavelengths.

The energy source 2012 may comprise a broad-band and/or a narrow-band source of electromagnetic energy. In some embodiments, the energy source 2012 comprises optical elements such as, e.g., filters, collimators, lenses, mirrors, etc., that are adapted to produce a desired energy beam E. For example, in some embodiments, the energy beam E is an infrared beam in a wavelength range between about 2 µm and 20 µm. In some embodiments, the energy beam E comprises an infrared beam in a wavelength range between about 4 µm and 10 µm. In the infrared wavelength range, water generally is the main contributor to the total absorption together with features from absorption of other blood components, particularly in the 6 µm-10 µm range. The 4 µm to 10 µm wavelength band has been found to be advantageous for determining glucose concentration, because glucose has a strong absorption peak structure from about 8.5 µm to 10 µm, whereas most other blood components have a relatively low and flat absorption spectrum in the 8.5 µm to 10 µm range. Two exceptions are water and hemoglobin, which are interferents in this range.

The energy beam E may be temporally modulated to provide increased signal-to-noise ratio (S/N) of the measurements provided by the analyzer 2010 as further described below. For example, in some embodiments, the beam E is modulated at a frequency of about 10 Hz or in a range from about 1 Hz to about 30 Hz. A suitable energy source 2012 may be an electrically modulated thin-film thermoresistive element such as the HawkEye IR-50 available from Hawkeye Technologies of Milford, Conn.

As depicted in FIG. 20, the energy beam E propagates along the optical axis X and passes through an aperture 2014 and a filter 2015 thereby providing a filtered energy beam $E_f$. The aperture 2014 helps collimate the energy beam E and can include one or more filters adapted to reduce the filtering burden of the filter 2015. For example, the aperture 2014 may comprise a broadband filter that substantially attenuates beam energy outside a wavelength band between about 4 µm to about 10 µm. The filter 2015 may comprise a narrow-band filter that substantially attenuates beam energy having wavelengths outside of a filter passband (which may be tunable or user-selectable in some embodiments). The filter passband may be specified by a half-power bandwidth ("HPBW"). In some embodiments, the filter 2015 may have an HPBW in a range from about 0.01 µm to about 1 µm. In some embodiments, the bandwidths are in a range from about 0.1 µm to 0.35 µm. Other filter bandwidths may be used. The filter 2015 may comprise a varying-passband filter, an electronically tunable filter, a liquid crystal filter, an interference filter, and/or a gradient filter. In some embodiments, the filter 2015 comprises one or a combination of a grating, a prism, a monochrometer, a Fabry-Perot etalon, and/or a polarizer. Other optical elements as known in the art may be utilized as well.

In the embodiment shown in FIG. 20, the analyzer 2010 comprises a filter wheel assembly 2021 configured to dispose one or more filters 2015 along the optical axis X. The filter wheel assembly 2021 comprises a filter wheel 2018, a filter wheel motor 2016, and a position sensor 2020. The filter wheel 2018 may be substantially circular and have one or more filters 2015 or other optical elements (e.g., apertures, gratings, polarizers, mirrors, etc.) disposed around the circumference of the wheel 2018. In some embodiments, the number of filters 2015 in the filter wheel 2016 may be, for example, 1, 2, 5, 10, 15, 20, 25, or more. The motor 2016 is configured to rotate the filter wheel 2018 to dispose a desired filter 2015 (or other optical element) in the energy beam E so as to produce the filtered beam $E_f$. In some embodiments, the motor 2016 comprises a stepper motor. The position sensor 2020 determines the angular position of the filter wheel 2016, and communicates a corresponding filter wheel position signal to the algorithm processor 416, thereby indicating which filter 2015 is in position on the optical axis X. In various embodiments, the position sensor 2020 may be a mechanical, optical, and/or magnetic encoder. An alternative to the filter wheel 2018 is a linear filter translated by a motor. The linear filter can include an array of separate filters or a single filter with properties that change along a linear dimension.

The filter wheel motor 2016 rotates the filter wheel 2018 to position the filters 2015 in the energy beam E to sequentially vary the wavelengths or the wavelength bands used to analyze the fluid sample. In some embodiments, each individual filter 2015 is disposed in the energy beam E for a dwell time during which optical properties in the passband of the filter are measured for the sample. The filter wheel motor 2016 then rotates the filter wheel 2018 to position another filter 2015 in the beam E. In some embodiments, 25 narrow-band filters are used in the filter wheel 2018, and the dwell time is about 2 seconds for each filter 2015. A set of optical measurements for all the filters can be taken in about 2 minutes, including sampling time and filter wheel movement. In some embodiments, the dwell time may be different for different filters 2015, for example, to provide a substantially similar S/N ratio for each filter measurement. Accordingly, the filter wheel assembly 2021 functions as a varying-passband filter that allows optical properties of the sample to be analyzed at a number of wavelengths or wavelength bands in a sequential manner.

In some embodiments of the analyzer 2010, the filter wheel 2018 includes 25 finite-bandwidth infrared filters having a Gaussian transmission profile and full-width half-maximum (FWHM) bandwidth of 28 cm$^{-1}$ corresponding to a bandwidth that varies from 0.14 µm at 7.08 µm to 0.28 µm at 10 µm. The central wavelength of the filters are, in microns: 7.082, 7.158, 7.241, 7.331, 7.424, 7.513, 7.605, 7.704, 7.800, 7.905, 8.019, 8.150, 8.271, 8.598, 8.718, 8.834, 8.969, 9.099, 9.217, 9.346, 9.461, 9.579, 9.718, 9.862, and 9.990.

With further reference to FIG. 20, the filtered energy beam $E_f$ propagates to a beamsplitter 2022 disposed along the optical axis X. The beamsplitter 2022 separates the filtered energy beam $E_f$ into a sample beam $E_s$ and a reference beam $E_r$. The reference beam $E_r$ propagates along a minor optical axis Y, which in this embodiment is substantially orthogonal to the optical axis X. The energies in the sample beam $E_s$ and the reference beam $E_r$ may comprise any suitable fraction of the energy in the filtered beam $E_f$. For example, in some embodiments, the sample beam $E_s$ comprises about 80%, and the reference beam $E_r$ comprises about 20%, of the filtered beam energy $E_f$. A reference detector 2036 is positioned along the minor optical axis Y. An optical element 2034, such as a lens, may be used to focus or collimate the reference beam $E_r$ onto the reference detector 2036. The reference detector 2036 provides a reference signal, which can be used to monitor fluctuations in the intensity of the energy beam E emitted by the source 2012. Such fluctuations may be due to drift effects, aging, wear, or other imperfections in the source 2012. The algorithm processor 416 may utilize the reference signal to identify changes in properties of the sample beam $E_s$ that are attributable to changes in the emission from the source 2012 and not to the properties of the fluid sample. By so doing, the analyzer 2010 may advantageously reduce possible sources of error in the calculated properties of the fluid sample (e.g., concentration). In other embodiments of the analyzer 2010, the beamsplitter 2022 is not used, and substantially all of the filtered energy beam $E_f$ propagates to the fluid sample.

As illustrated in FIG. 20, the sample beam $E_s$ propagates along the optical axis X and a relay lens 2024 transmits the sample beam $E_s$ into a sample cell 2048 so that at least a fraction of the sample beam $E_s$ is transmitted through at least a portion of the fluid sample in the sample cell 2048. A sample detector 2030 is positioned along the optical axis X to measure the sample beam $E_s$ that has passed through the portion of the fluid sample. An optical element 2028, such as a lens, may be used to focus or collimate the sample beam $E_s$ onto the sample detector 2030. The sample detector 2030 provides a sample signal that can be used by the algorithm processor 416 as part of the sample analysis.

In the embodiment of the analyzer 2010 shown in FIG. 20, the sample cell 2048 is located toward the outer circumference of the centrifuge wheel 2050 (which can correspond, for example, to the sample cell holder 820 described herein). The sample cell 2048 preferably comprises windows that are substantially transmissive to energy in the sample beam $E_s$. For example, in implementations using mid-infrared energy, the windows may comprise calcium fluoride. As described herein with reference to FIG. 5, the sample cell 2048 is in fluid communication with an injector system that permits filling the sample cell 2048 with a fluid sample (e.g., whole blood) and flushing the sample cell 2048 (e.g., with saline or a detergent). The injector system may disconnect after filling the sample cell 2048 with the fluid sample to permit free spinning of the centrifuge wheel 2050.

The centrifuge wheel 2050 can be spun by a centrifuge motor 2026. In some embodiments of the analyzer 2010, the fluid sample (e.g., a whole blood sample) is spun at about 7200 RPM for about 2 minutes to separate blood plasma for spectral analysis. In some embodiments, the fluid sample is spun at about 4500 RPM. In some embodiments, an anti-clotting agent such as heparin may be added to the fluid sample before centrifuging to reduce clotting. With reference to FIG. 20, the centrifuge wheel 2050 is rotated to a position where the sample cell 2048 intercepts the sample beam $E_s$, allowing energy to pass through the sample cell 2048 to the sample detector 2030.

The embodiment of the analyzer 2010 illustrated in FIG. 20 advantageously permits direct measurement of the concentration of analytes in the plasma sample rather than by inference of the concentration from measurements of a whole blood sample. An additional advantage is that relatively small volumes of fluid may be spectroscopically analyzed. For example, in some embodiments the fluid sample volume is between about 1 μL and 80 μL and is about 25 μL in some embodiments. In some embodiments, the sample cell 2048 is disposable and is intended for use with a single patient or for a single measurement.

In some embodiments, the reference detector 2036 and the sample detector 2030 comprise broadband pyroelectric detectors. As known in the art, some pyroelectric detectors are sensitive to vibrations. Thus, for example, the output of a pyroelectric infrared detector is the sum of the exposure to infrared radiation and to vibrations of the detector. The sensitivity to vibrations, also known as "microphonics," can introduce a noise component to the measurement of the reference and sample energy beams $E_r$, $E_s$ using some pyroelectric infrared detectors. Because it may be desirable for the analyzer 2010 to provide high signal-to-noise ratio measurements, such as, e.g., S/N in excess of 100 dB, some embodiments of the analyzer 2010 utilize one or more vibrational noise reduction apparatus or methods. For example, the analyzer 2010 may be mechanically isolated so that high S/N spectroscopic measurements can be obtained for vibrations below an acceleration of about 1.5 G.

In some embodiments of the analyzer 2010, vibrational noise can be reduced by using a temporally modulated energy source 2012 combined with an output filter. In some embodiments, the energy source 2012 is modulated at a known source frequency, and measurements made by the detectors 2036 and 2030 are filtered using a narrowband filter centered at the source frequency. For example, in some embodiments, the energy output of the source 2012 is sinusoidally modulated at 10 Hz, and outputs of the detectors 2036 and 2030 are filtered using a narrow bandpass filter of less than about 1 Hz centered at 10 Hz. Accordingly, microphonic signals that are not at 10 Hz are significantly attenuated. In some embodiments, the modulation depth of the energy beam E may be greater than 50% such as, for example, 80%. The duty cycle of the beam may be between about 30% and 70%. The temporal modulation may be sinusoidal or any other waveform. In embodiments utilizing temporally modulated energy sources, detector output may be filtered using a synchronous demodulator and digital filter. The demodulator and filter are software components that may be digitally implemented in a processor such as the algorithm processor 416. Synchronous demodulators, coupled with low pass filters, are often referred to as "lock in amplifiers."

The analyzer 2010 may also include a vibration sensor 2032 (e.g., one or more accelerometers) disposed near one (or both) of the detectors 2036 and 2030. The output of the vibration sensor 2032 is monitored, and suitable actions are taken if the measured vibration exceeds a vibration threshold. For example, in some embodiments, if the vibration sensor 2032 detects above-threshold vibrations, the system discards any ongoing measurement and "holds off" on performing further measurements until the vibrations drop below the threshold. Discarded measurements may be repeated after the vibrations drop below the vibration threshold. In some embodiments, if the duration of the "hold off" is sufficiently long, the fluid in the sample cell 2030 is flushed, and a new fluid sample is delivered to the cell 2030 for measurement. The vibration threshold may be selected so that the error in analyte measurement is at an acceptable level for vibrations below the threshold. In some embodiments, the threshold corresponds to an error in glucose concentration of 5 mg/dL. The vibration threshold may be determined individually for each filter 2015.

Certain embodiments of the analyzer 2010 include a temperature system (not shown in FIG. 20) for monitoring and/or regulating the temperature of system components (such as the detectors 2036, 2030) and/or the fluid sample. Such a temperature system can include temperature sensors, thermoelectrical heat pumps (e.g., a Peltier device), and/or thermistors, as well as a control system for monitoring and/or regulating temperature. In some embodiments, the control system comprises a proportional-plus-integral-plus-derivative (PID) control. For example, in some embodiments, the temperature system is used to regulate the temperature of the detectors 2030, 2036 to a desired operating temperature, such as 35 degrees Celsius.

Optical Measurement

The analyzer 2010 illustrated in FIG. 20 can be used to determine optical properties of a substance in the sample cell 2048. The substance can include whole blood, plasma, saline, water, air or other substances. In some embodiments, the optical properties include measurements of an absorbance, transmittance, and/or optical density in the wavelength passbands of some or all of the filters 2015 disposed in the filter wheel 2018. As described above, a measurement cycle comprises disposing one or more filters 2015 in the energy beam E for a dwell time and measuring a reference signal with the reference detector 2036 and a sample signal with the sample detector 2030. The number of filters 2015 used in the measurement cycle will be denoted by N, and each filter 2015 passes energy in a passband around a center wavelength $\lambda_i$, where i is an index ranging over the number of filters (e.g., from 1 to N). The set of optical measurements from the sample detector 2036 in the passbands of the N filters 2015 provide a wavelength-dependent spectrum of the substance in the sample cell 2048. The spectrum will be denoted by $C_s(\lambda_i)$, where $C_s$ may be a transmittance, absorbance, optical density, or some other measure of an optical property of the substance. In some embodiments, the spectrum is normalized with respect to one or more of the reference signals measured by the reference detector 2030 and/or with respect to spectra of a reference substance (e.g., air or saline). The measured spectra are communicated to the algorithm processor 416 for calculation of the concentration of the analyte(s) of interest in the fluid sample.

In some embodiments, the analyzer 2010 performs spectroscopic measurements on the fluid sample (known as a "wet" reading) and on one or more reference samples. For example, an "air" reading occurs when the sample detector 2036 measures the sample signal without the sample cell 2048 in place along the optical axis X. (This can occur, for example, when the opposite opening 1530 is aligned with the optical axis X). A "water" or "saline" reading occurs when the sample cell 2048 is filled with water or saline, respectively. The algorithm processor 416 may be programmed to calculate analyte concentration using a combination of these spectral measurements.

In some embodiments, a pathlength corrected spectrum is calculated using wet, air, and reference readings. For example, the transmittance at wavelength denoted by $T_i$, may be calculated according to $T_i=(S_i(\text{wet})/R_i(\text{wet}))/(S_i(\text{air})/R_i(\text{air}))$, where $S_i$ denotes the sample signal from the sample detector 2036 and $R_i$ denotes the corresponding reference signal from the reference detector 2030. In some embodiments, the algorithm processor 416 calculates the optical density, $OD_i$, as a logarithm of the transmittance, e.g., according to $OD_i=-\text{Log}(T_i)$. In one implementation, the analyzer 2010 takes a set of wet readings in each of the N filter passbands and then takes a set of air readings in each of the N filter passbands. In other embodiments, the analyzer 2010 may take an air reading before (or after) the corresponding wet reading.

The optical density $OD_i$ is the product of the absorption coefficient at wavelength $\lambda_i$, $\alpha_i$, times the pathlength L over which the sample energy beam $E_s$ interacts with the substance in the sample cell 2048, e.g., $OD_i = \alpha_i L$. The absorption coefficient $\alpha_i$ of a substance may be written as the product of an absorptivity per mole times a molar concentration of the substance. FIG. 20 schematically illustrates the pathlength L of the sample cell 2048. The pathlength L may be determined from spectral measurements made when the sample cell 2048 is filled with a reference substance. For example, because the absorption coefficient for water (or saline) is known, one or more water (or saline) readings can be used to determine the pathlength L from measurements of the transmittance (or optical density) through the cell 2048. In some embodiments, several readings are taken in different wavelength passbands, and a curve-fitting procedure is used to estimate a best-fit pathlength L. The pathlength L may be estimated using other methods including, for example, measuring interference fringes of light passing through an empty sample cell 2048.

The pathlength L may be used to determine the absorption coefficients of the fluid sample at each wavelength. Molar concentration of an analyte of interest can be determined from the absorption coefficient and the known molar absorptivity of the analyte. In some embodiments, a sample measurement cycle comprises a saline reading (at one or more wavelengths), a set of N wet readings (taken, for example, through a sample cell 2048 containing saline solution), followed by a set of N air readings (taken, for example, through the opposite opening 1530). As discussed above, the sample measurement cycle can be performed in about 2 minutes when the filter dwell times are about 2 seconds. After the sample measurement cycle is completed, a detergent cleaner may be flushed through the sample cell 2048 to reduce buildup of organic matter (e.g., proteins) on the windows of the sample cell 2048. The detergent is then flushed to a waste bladder.

In some embodiments, the system stores information related to the spectral measurements so that the information is readily available for recall by a user. The stored information can include wavelength-dependent spectral measurements (including fluid sample, air, and/or saline readings), computed analyte values, system temperatures and electrical properties (e.g., voltages and currents), and any other data related to use of the system (e.g., system alerts, vibration readings, S/N ratios, etc.). The stored information may be retained in the system for a time period such as, for example, 30 days. After this time period, the stored information may be communicated to an archival data storage system and then deleted from the system. In some embodiments, the stored information is communicated to the archival data storage system via wired or wireless methods, e.g., over a hospital information system (HIS).

Analyte Analysis

The algorithm processor 416 (FIG. 4) (or any other suitable processor or processors) may be configured to receive from the analyzer 2010 the wavelength-dependent optical measurements $Cs(\lambda_i)$ of the fluid sample. In some embodiments, the optical measurements comprise spectra such as, for example, optical densities $OD_i$ measured in each of the N filter passbands centered around wavelengths $\lambda_i$. The optical measurements $Cs(\lambda_i)$ are communicated to the processor 416, which analyzes the optical measurements to detect and quantify one or more analytes in the presence of interferents. In some embodiments, one or more poor quality optical measurements $Cs(\lambda_i)$ are rejected (e.g., as having a S/N ratio that is too low), and the analysis performed on the remaining, sufficiently high-quality measurements. In another embodiment, additional optical measurements of the fluid sample are taken by the analyzer 2010 to replace one or more of the poor quality measurements.

Interferents can comprise components of a material sample being analyzed for an analyte, where the presence of the interferent affects the quantification of the analyte. Thus, for example, in the spectroscopic analysis of a sample to determine an analyte concentration, an interferent could be a compound having spectroscopic features that overlap with those of the analyte, in at least a portion of the wavelength range of the measurements. The presence of such an interferent can introduce errors in the quantification of the analyte. More specifically, the presence of one or more interferents can affect the sensitivity of a measurement technique to the concentration of analytes of interest in a material sample, especially when the system is calibrated in the absence of, or with an unknown amount of, the interferent.

Independently of or in combination with the attributes of interferents described above, interferents can be classified as being endogenous (i.e., originating within the body) or exogenous (i.e., introduced from or produced outside the body). As an example of these classes of interferents, consider the analysis of a blood sample (or a blood component sample or a blood plasma sample) for the analyte glucose. Endogenous interferents include those blood components having origins within the body that affect the quantification of glucose, and can include water, hemoglobin, blood cells, and any other component that naturally occurs in blood. Exogenous interferents include those blood components having origins outside of the body that affect the quantification of glucose, and can include items administered to a person, such as medicaments, drugs, foods or herbs, whether administered orally, intravenously, topically, etc.

Independently of or in combination with the attributes of interferents described above, interferents can comprise components which are possibly, but not necessarily, present in the sample type under analysis. In the example of analyzing samples of blood or blood plasma drawn from patients who are receiving medical treatment, a medicament such as acetaminophen is possibly, but not necessarily, present in this sample type. In contrast, water is necessarily present in such blood or plasma samples.

Certain disclosed analysis methods are particularly effective if each analyte and interferent has a characteristic signature in the measurement (e.g., a characteristic spectroscopic feature), and if the measurement is approximately affine (e.g., includes a linear term and an offset) with respect to the concentration of each analyte and interferent. In such methods, a calibration process is used to determine a set of one or more calibration coefficients and a set of one or more optional offset values that permit the quantitative estimation of an analyte. For example, the calibration coefficients and the offsets may be used to calculate an analyte concentration from spectroscopic measurements of a material sample (e.g., the concentration of glucose in blood plasma). In some of these methods, the concentration of the analyte is estimated by multiplying the calibration coefficient by a measurement value (e.g., an optical density) to estimate the concentration of the analyte. Both the calibration coefficient and measurement can comprise arrays of numbers. For example, in some embodiments, the measurement comprises spectra $C_s(\lambda_i)$ measured at the wavelengths $\lambda_i$, and the calibration coefficient and optional offset comprise an array of values corresponding to each wavelength $\lambda_i$. In some embodiments, as further described below, a hybrid linear analysis (HLA) technique is used to estimate analyte concentration in the presence of a set of interferents, while retaining a high degree of sensitivity to the desired analyte. The data used to accommodate the set of possible interferents can include (a) signatures of each of the members of the family of potential additional substances and (b) a typical quantitative level at which each additional substance, if present, is likely to appear. In some embodiments, the calibration coefficient (and optional offset) are adjusted to minimize or reduce the sensitivity of the calibration to the presence of interferents that are identified as possibly being present in the fluid sample.

In some embodiments, the analyte analysis method uses a set of training spectra each having known analyte concentration and produces a calibration that minimizes the variation in estimated analyte concentration with interferent concentration. The resulting calibration coefficient indicates sensitivity of the measurement to analyte concentration. The training spectra need not include a spectrum from the individual whose analyte concentration is to be determined. That is, the term "training" when used in reference to the disclosed methods does not require training using measurements from the individual whose analyte concentration will be estimated (e.g., by analyzing a bodily fluid sample drawn from the individual).

Several terms are used herein to describe the analyte analysis process. The term "Sample Population" is a broad term and includes, without limitation, a large number of samples having measurements that are used in the computation of calibration values (e.g., calibration coefficients and optional offsets). In some embodiments, the term Sample Population comprises measurements (such as, e.g., spectra) from individuals and may comprise one or more analyte measurements determined from those same individuals. Additional demographic information may be available for the individuals whose sample measurements are included in the Sample Population. For an embodiment involving the spectroscopic determination of glucose concentration, the Sample Population measurements may include a spectrum (measurement) and a glucose concentration (analyte measurement).

Various embodiments of Sample Populations may be used in various embodiments of the systems and methods described herein. Several examples of Sample Populations will now be described. These examples are intended to illustrate certain aspects of possible Sample Population embodiments but are not intended to limit the types of Sample Populations that may be generated. In certain embodiments, a Sample Population may include samples from one or more of the example Sample Populations described below.

In some embodiments of the systems and methods described herein, one or more Sample Populations are included in a "Population Database." The Population Database may be implemented and/or stored on a computer-readable medium. In certain embodiments, the systems and methods may access the Population Database using wired and/or wireless techniques. Certain embodiments may utilize several different Population Databases that are accessible locally and/or remotely. In some embodiments, the Population Database includes one or more of the example Sample Populations described below. In some embodiments, two or more databases can be combined into a single database, and in other embodiments, any one database can be divided into multiple databases.

An example Sample Population may comprise samples from individuals belonging to one or more demographic groups including, for example, ethnicity, nationality, gender, age, etc. Demographic groups may be established for any suitable set of one or more distinctive factors for the group including, for example, medical, cultural, behavioral, biological, geographical, religious, and genealogical traits. For example, in certain embodiments, a Sample Population includes samples from individuals from a specific ethnic group (e.g., Caucasians, Hispanics, Asians, African Americans, etc.). In another embodiment, a Sample Population includes samples from individuals of a specific gender. In some embodiments, a Sample Population includes samples from individuals belonging to more than one demographic group (e.g., samples from Caucasian women).

Another example Sample Population can comprise samples from individuals having one or more medical conditions. For example, a Sample Population may include samples from individuals who are healthy and unmedicated (sometimes referred to as a Normal Population). In some embodiments, the Sample Population includes samples from individuals having one or more health conditions (e.g., diabetes). In some embodiments, the Sample Population includes samples from individuals taking one or more medications. In certain embodiments, Sample Population includes samples from individuals diagnosed to have a certain medical condition or from individuals being treated for certain medical conditions or some combination thereof. The Sample Population may include samples from individuals such as, for example, ICU patients, maternity patients, and so forth.

An example Sample Population may comprise samples that have the same interferent or the same type of interferents. In some embodiments, a Sample Population can comprise multiple samples, all lacking an interferent or a type of interferent. For example, a Sample Population may comprise samples that have no exogenous interferents, that have one or more exogenous interferents of either known or unknown concentration, and so forth. The number of interferents in a sample depends on the measurement and analyte(s) of interest, and may number, in general, from zero to a very large number (e.g., greater than 300). All of the interferents typically are not expected to be present in a particular material sample, and in many cases, a smaller number of interferents (e.g., 0, 1, 2, 5, 10, 15, 20, or 25) may be used in an analysis. In certain embodiments, the number of interferents used in the analysis is less than or equal to the number of wavelength-dependent measurements N in the spectrum $Cs(\lambda_i)$.

Certain embodiments of the systems and methods described herein are capable of analyzing a material sample using one or more Sample Populations (e.g., accessed from the Population Database). Certain such embodiments may use information regarding some or all of the interferents which may or may not be present in the material sample. In some embodiments, a list of one or more possible interferents, referred to herein as forming a "Library of Interferents," can be compiled. Each interferent in the Library can be referred to as a "Library Interferent." The Library Interferents may include exogenous interferents and endogenous interferents that may be present in a material sample. For example, an interferent may be present due to a medical condition causing abnormally high concentrations of the exogenous and endogenous interferents. In some embodiments, the Library of Interferents may not include one or more interferents that are known to be present in all samples. Thus, for example, water, which is a glucose interferent for many spectroscopic measurements, may not be included in the Library of Interferents. In certain embodiments, the systems and methods use samples in the Sample Population to train calibration methods.

The material sample being measured, for example a fluid sample in the sample cell 2048, may also include one or more Library Interferents which may include, but is not limited to, an exogenous interferent or an endogenous interferent. Examples of exogenous interferent can include medications, and examples of endogenous interferents can include urea in persons suffering from renal failure. In addition to components naturally found in the blood, the ingestion or injection of some medicines or illicit drugs can result in very high and rapidly changing concentrations of exogenous interferents.

In some embodiments, measurements of a material sample (e.g., a bodily fluid sample), samples in a Sample Population, and the Library Interferents comprise spectra (e.g., infrared spectra). The spectra obtained from a sample and/or an interferent may be temperature dependent. In some embodiments, it may be beneficial to calibrate for temperatures of the individual samples in the Sample Population or the interferents in the Library of Interferents. In some embodiments, a temperature calibration procedure is used to generate a temperature calibration factor that substantially accounts for the sample temperature. For example, the sample temperature can be measured, and the temperature calibration factor can be applied to the Sample Population and/or the Library Interferent spectral data. In some embodiments, a water or saline spectrum is subtracted from the sample spectrum to account for temperature effects of water in the sample.

In other embodiments, temperature calibration may not be used. For example, if Library Interferent spectra, Sample Population spectra, and sample spectra are obtained at approximately the same temperature, an error in a predicted analyte concentration may be within an acceptable tolerance. If the temperature at which a material sample spectrum is measured is within, or near, a temperature range (e.g., several degrees Celsius) at which the plurality of Sample Population spectra are obtained, then some analysis methods may be relatively insensitive to temperature variations. Temperature calibration may optionally be used in such analysis methods.

Figure 21:
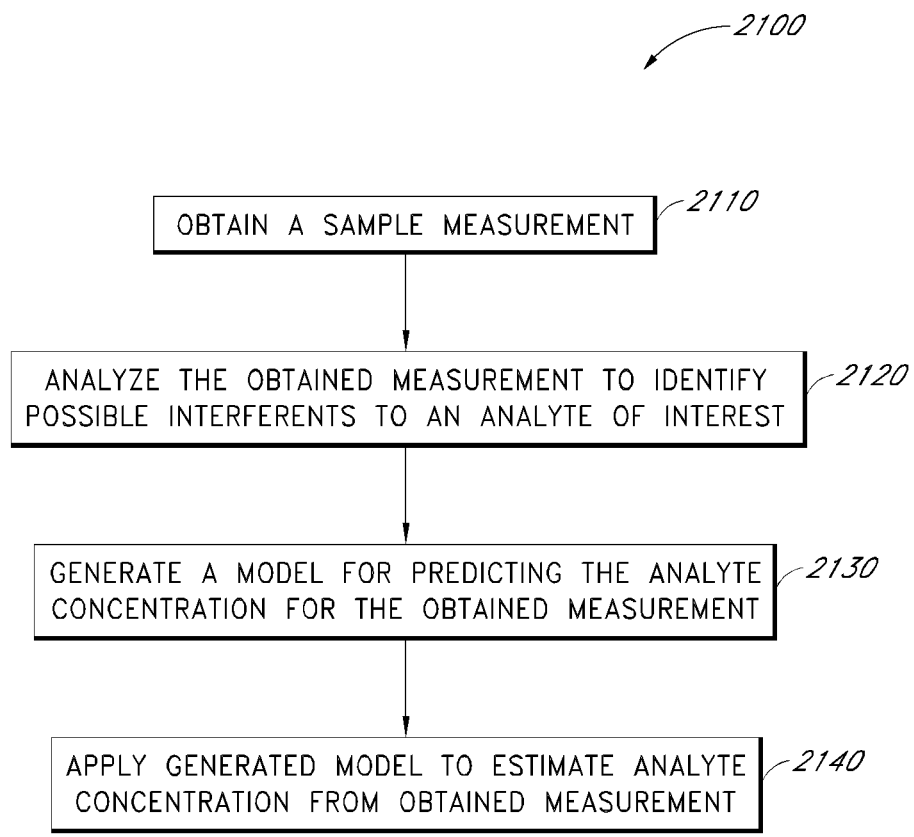
FIG. 21 is a flowchart that schematically illustrates an embodiment of a method for estimating the concentration of an analyte in the presence of interferents.

Systems and Methods for Estimating Analyte Concentration in the Presence of Interferents FIG. 21 is a flowchart that schematically illustrates an embodiment of a method 2100 for estimating the concentration of an analyte in the presence of interferents. In block 2110, a measurement of a sample is obtained, and in block 2120 data relating to the obtained measurement is analyzed to identify possible interferents to the analyte. In block 2130, a model is generated for predicting the analyte concentration in the presence of the identified possible interferents, and in block 2140 the model is used to estimate the analyte concentration in the sample from the measurement. In certain embodiments of the method 2100, the model generated in block 2130 is selected to reduce or minimize the effect of identified interferents that are not present in a general population of which the sample is a member.

An example embodiment of the method 2100 of FIG. 21 for the determination of an analyte (e.g., glucose) in a blood sample will now be described. This example embodiment is intended to illustrate various aspects of the method 2100 but is not intended as a limitation on the scope of the method 2100 or on the range of possible analytes. In this example, the sample measurement in block 2110 is an absorption spectrum, $Cs(\lambda_i)$, of a measurement sample S that has, in general, one analyte of interest, glucose, and one or more interferents.

In block 2120, a statistical comparison of the absorption spectrum of the sample S with a spectrum of the Sample Population and combinations of individual Library Interferent spectra is performed. The statistical comparison provides a list of Library Interferents that are possibly contained in sample S and can include either no Library Interferents or one or more Library Interferents. In this example, in block 2130, one or more sets of spectra are generated from spectra of the Sample Population and their respective known analyte concentrations and known spectra of the Library Interferents identified in block 2120. In block 2130, the generated spectra are used to calculate a model for predicting the analyte concentration from the obtained measurement. In some embodiments, the model comprises one or more calibration coefficients $\kappa(\lambda_i)$ that can be used with the sample measurements $Cs(\lambda_i)$ to provide an estimate of the analyte concentration, $g_{est}$. In block 2140, the estimated analyte concentration is determined form the model generated in block 2130. For example, in some embodiments of HLA, the estimated analyte concentration is calculated according to a linear formula: $g_{est} = \kappa(\lambda_i) \cdot C_s(\lambda_i)$. Because the absorption measurements and calibration coefficients may represent arrays of numbers, the multiplication operation indicated in the preceding formula may comprise a sum of the products of the measurements and coefficients (e.g., an inner product or a matrix product). In some embodiments, the calibration coefficient is determined so as to have reduced or minimal sensitivity to the presence of the identified Library Interferents.

Figure 22:
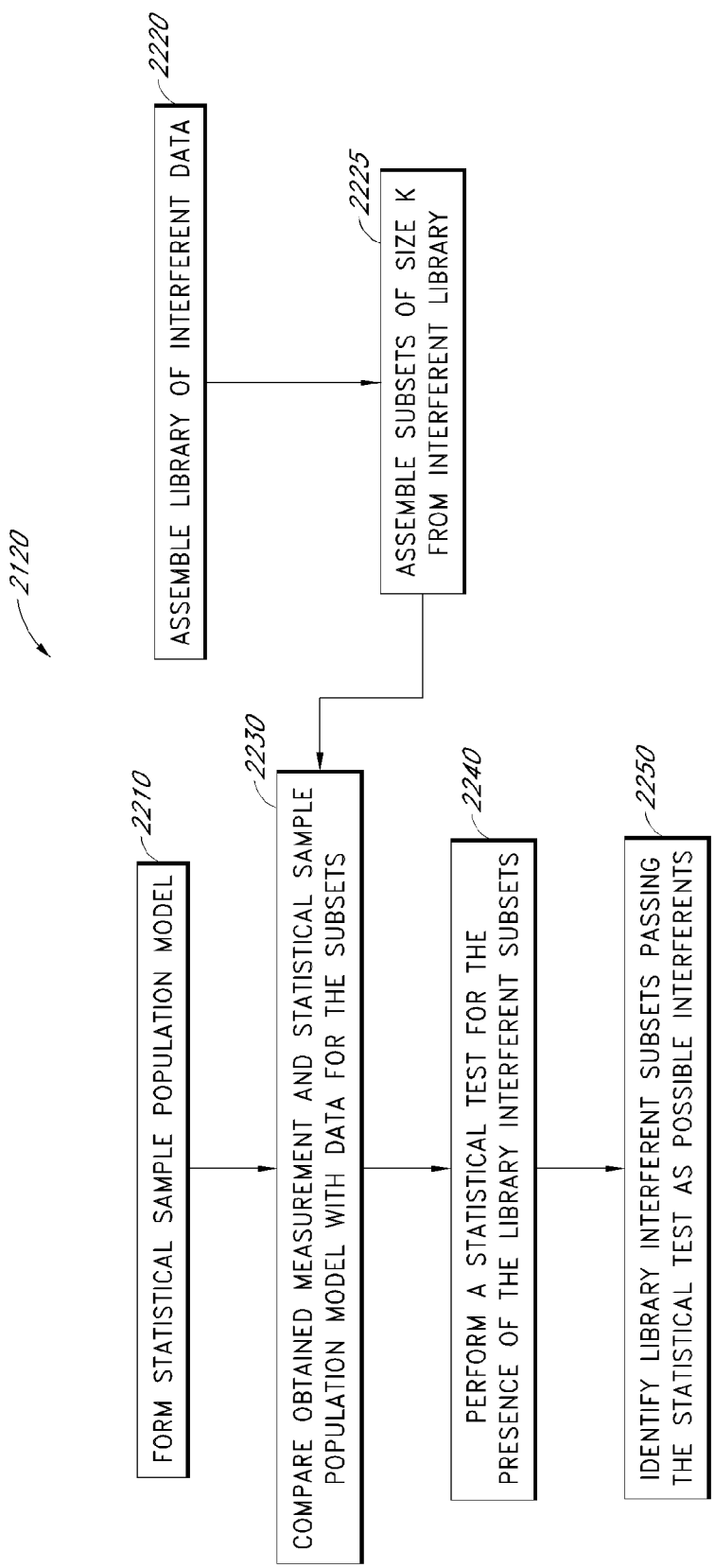
FIG. 22 is a flowchart that schematically illustrates an embodiment of a method for performing a statistical comparison of the absorption spectrum of a sample with the spectrum of a sample population and combinations of individual library interferent spectra.

An example embodiment of block 2120 of the method 2100 will now be described with reference to FIG. 22. In this example, block 2120 includes forming a statistical Sample Population model (block 2210), assembling a library of interferent data (block 2220), assembling all subsets of size K of the library interferents (block 2225), comparing the obtained measurement and statistical Sample Population model with data for each set of interferents from an interferent library (block 2230), performing a statistical test for the presence of each interferent from the interferent library (block 2240), and identifying possible interferents that pass the statistical test (block 2250). The size K of the subsets may be an integer such as, for example, 1, 2, 3, 4, 5, 6, 10, 16, or more. The acts of block 2220 can be performed once or can be updated as necessary. In certain embodiments, the acts of blocks 2230, 2240, and 2250 are performed sequentially for all subsets of Library Interferents that pass the statistical test (block 2240). In this example, in block 2210, a Sample Population Database is formed that includes a statistically large Sample Population of individual spectra taken over the same wavelength range as the sample spectrum, $C_s(\lambda_i)$. The Database also includes an analyte concentration corresponding to each spectrum. For example, if there are P Sample Population spectra, then the spectra in the Database can be represented as $C = \{C_1, C_2, \ldots, C_P\}$, and the analyte concentration corresponding to each spectrum can be represented as $g = \{g_1, g_2, \ldots, g_P\}$. In some embodiments, the Sample Population does not have any of the Library Interferents present, and the material sample has interferents contained in the Sample Population and one or more of the Library Interferents.

In some embodiments of block 2210, the statistical sample model comprises a mean spectrum and a covariance matrix calculated for the Sample Population. For example, if each spectrum measured at N wavelengths $\lambda_i$ is represented by an N×1 array, C, then the mean spectrum, $\mu$, is an N×1 array having values at each wavelength averaged over the range of spectra in the Sample Population. The covariance matrix, V, is calculated as the expected value of the deviation between C and $\mu$ and can be written as $V=E((C-\mu)(C-\mu)^T)$ where $E(\cdot)$ represents the expected value and the superscript T denotes transpose. In other embodiments, additional statistical parameters may be included in the statistical model of the Sample Population spectra.

Additionally, a Library of Interferents may be assembled in block 2220. A number of possible interferents can be identified, for example, as a list of possible medications or foods that might be ingested by the population of patients at issue. Spectra of these interferents can be obtained, and a range of expected interferent concentrations in the blood, or other expected sample material, can be estimated. In certain embodiments, the Library of Interferents includes, for each of "M" interferents, the absorption spectrum normalized to unit interferent concentration of each interferent, $IF=\{IF_1, IF_2, \ldots, IF_M\}$, and a range of concentrations for each interferent from $Tmax=\{Tmax_1, Tmax_2, \ldots, Tmax_M\}$ to $Tmin=\{Tmin_1, Tmin_2, \ldots, Tmin_M\}$. Information in the Library may be assembled once and accessed as needed. For example, the Library and the statistical model of the Sample Population may be stored in a storage device associated with the algorithm processor 416 (see, FIG. 4).

Continuing in block 2225, the algorithm processor 416 assembles one or more subsets comprising a number K of spectra taken from the Library of Interferents. The number K may be an integer such as, for example, 1, 2, 3, 4, 5, 6, 10, 16, or more. In some embodiments, the subsets comprise all combinations of the M Library spectra taken K at a time. In these embodiments, the number of subsets having K spectra is $M!/(K!(M-K)!)$, where ! represents the factorial function.

Continuing in block 2230, the obtained measurement data (e.g., the sample spectrum) and the statistical Sample Population model (e.g., the mean spectrum and the covariance matrix) are compared with data for each subset of interferents determined in block 2225 in order to determine the presence of possible interferents in the sample (block 2240). In some embodiments, the statistical test for the presence of an interferent subset in block 2240 comprises determining the concentrations of each subset of interferences that minimize a statistical measure of "distance" between a modified spectrum of the material sample and the statistical model of the Sample Population (e.g., the mean $\mu$ and the covariance V). The term "concentration" used in this context refers to a computed value, and, in some embodiments, that computed value may not correspond to an actual concentration. The concentrations may be calculated numerically. In some embodiments, the concentrations are calculated by algebraically solving a set of linear equations. The statistical measure of distance may comprise the well-known Mahalanobis distance (or square of the Mahalanobis distance) and/or some other suitable statistical distance metric (e.g., Hotelling's T-square statistic). In certain implementations, the modified spectrum is given by $C'_s(T)=C_s-IF\cdot T$ where $T=(T_1, T_2, \ldots T_K)^T$ is a K-dimensional column vector of interferent concentrations and $IF=\{IF_1, IF_2, \ldots IF_K\}$ represents the K interferent absorption spectra of the subset. In some embodiments, concentration of the $i^{th}$ interferent is assumed to be in a range from a minimum value, $Tmin_i$, to a maximum value, $Tmax_i$. The value of $Tmin_i$ may be zero, or may be a value between zero and $Tmax_i$, such as a fraction of $Tmax_i$, or may be a negative value. Negative values represent interferent concentrations that are smaller than baseline interferent values in the Sample Population.

In block 2250, a list of a number $N_S$ of possible interferent subsets $\xi$ may be identified as the particular subsets that pass one or more statistical tests (in block 2240) for being present in the material sample. One or more statistical tests may be used, alone or in combination, to identify the possible interferents. For example, if a statistical test indicates that an $i^{th}$ interferent is present in a concentration outside the range $Tmin_i$ to $Tmax_i$, then this result may be used to exclude the $i^{th}$ interferent from the list of possible interferents. In some embodiments, only the single most probable interferent subset is included on the list, for example, the subset having the smallest statistical distance (e.g., Mahalanobis distance). In an embodiment, the list includes the subsets $\xi$ having statistical distances smaller than a threshold value. In certain embodiments, the list includes a number $N_S$ of subsets having the smallest statistical distances, e.g., the list comprises the "best" candidate subsets. The number $N_S$ may be any suitable integer such as 10, 20, 50, 100, 200, or more. An advantage of selecting the "best" $N_S$ subsets is reduced computational burden on the algorithm processor 416. In some embodiments, the list includes all the Library Interferents. In certain such embodiments, the list is selected to comprise combinations of the $N_S$ subsets taken L at a time. For example, in some embodiments, pairs of subsets are taken (e.g., L=2). An advantage of selecting pairs of subsets is that pairing captures the most likely combinations of interferents and the "best" candidates are included multiple times in the list of possible interferents. In embodiments in which combinations of L subsets are selected, the number of combinations of subsets in the list of possible interferent subsets is $N_S!/(L!(N_S-L)!)$.

In other embodiments, the list of possible interferent subsets $\xi$ is determined using a combination of some or all of the above criteria. In another embodiment, the list of possible interferent subsets $\xi$ includes each of the subsets assembled in block 2225. Many selection criteria are possible for the list of possible interferent subsets $\xi$.

Figure 23:
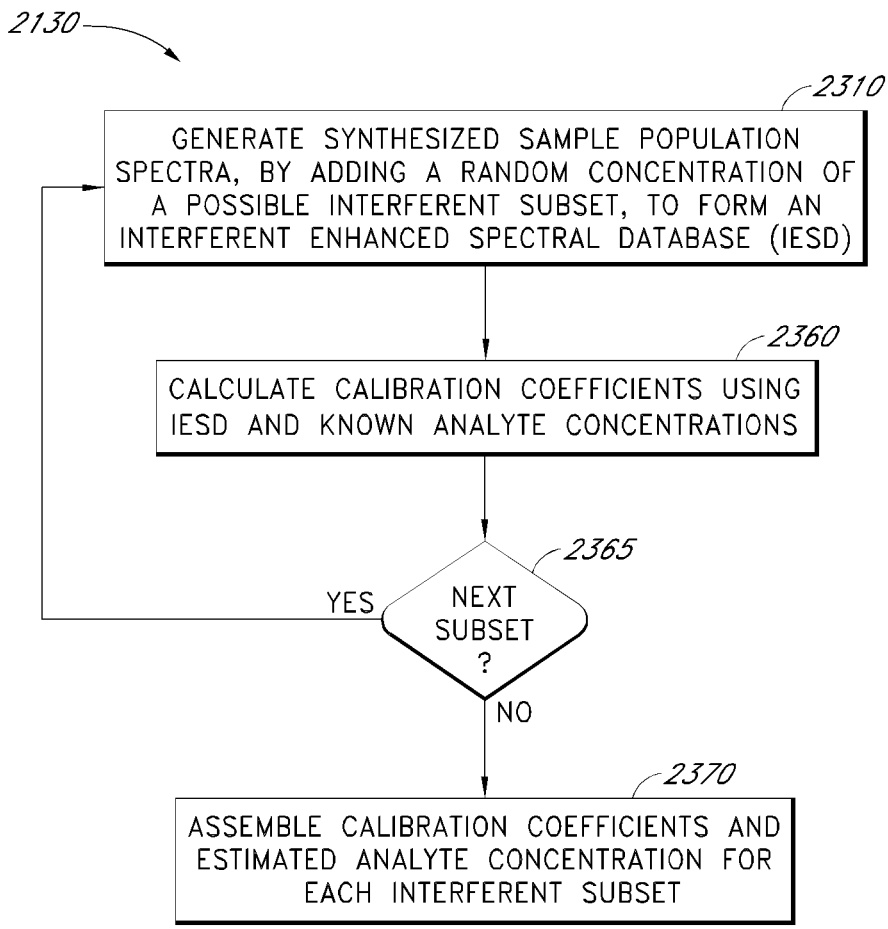
FIG. 23 is a flowchart that schematically illustrates an example embodiment of a method for estimating analyte concentration in the presence of the possible interferents.

Returning to FIG. 21, the method 2100 continues in block 2130 where analyte concentration is estimated in the presence of the possible interferent subsets $\xi$ determined in block 2250. FIG. 23 is a flowchart that schematically illustrates an example embodiment of the acts of block 2130. In block 2310, synthesized Sample Population measurements are generated to form an Interferent Enhanced Spectral Database (IESD). In block 2360, the IESD and known analyte concentrations are used to generate calibration coefficients for the selected interferent subset. As indicated in block 2365, blocks 2310 and 2360 may be repeated for each interferent subset $\xi$ identified in the list of possible interferent subsets (e.g., in block 2250 of FIG. 22). In this example embodiment, when all the interferent subsets $\xi$ have been processed, the method continues in block 2370, wherein an average calibration coefficient is applied to the measured spectra to determine a set of analyte concentrations.

In one example embodiment for block 2310, synthesized Sample Population spectra are generated by adding random concentrations of each interferent in one of the possible interferent subsets $\xi$. These spectra are referred to herein as an Interferent-Enhanced Spectral Database or IESD. In one example method, the IESD is formed as follows. A plurality of Randomly-Scaled Single Interferent Spectra (RSIS) are formed for each interferent in the interferent subset $\xi$. Each RSIS is formed by combinations of the interferent having spectrum IF multiplied by the maximum concentration Tmax, which is scaled by a random factor between zero and one. In certain embodiments, the scaling places the maximum concentration at the $95^{th}$ percentile of a log-normal distribution in order to generate a wide range of concentrations. In some embodiments, the log-normal distribution has a standard deviation equal to half of its mean value.

In this example method, individual RSIS are then combined independently and in random combinations to form a large family of Combination Interferent Spectra (CIS), with each spectrum in the CIS comprising a random combination of RSIS, selected from the full set of identified Library Interferents. An advantage of this method of selecting the CIS is that it produces adequate variability with respect to each interferent, independently across separate interferents.

The CIS and replicates of the Sample Population spectra are combined to form the IESD. Since the interferent spectra and the Sample Population spectra may have been obtained from measurements having different optical pathlengths, the CIS may be scaled to the same pathlength as the Sample Population spectra. The Sample Population Database is then replicated R times, where R depends on factors including the size of the Database and the number of interferents. The IESD includes R copies of each of the Sample Population spectra, where one copy is the original Sample Population Data, and the remaining R−1 copies each have one randomly chosen CIS spectra added. Accordingly, each of the IESD spectra has an associated analyte concentration from the Sample Population spectra used to form the particular IESD spectrum. In some embodiments, a 10-fold replication of the Sample Population Database is used for 130 Sample Population spectra obtained from 58 different individuals and 18 Library Interferents. A smaller replication factor may be used if there is greater spectral variety among the Library Interferent spectra, and a larger replication factor may be used if there is a greater number of Library Interferents.

After the IESD is generated in block 2310, in block 2360, the IESD spectra and the known, random concentrations of the subset interferents are used to generate a calibration coefficient for estimating the analyte concentration from a sample measurement. The calibration coefficient is calculated in some embodiments using a hybrid linear analysis (HLA) technique. In certain embodiments, the HLA technique uses a reference analyte spectrum to construct a set of spectra that are free of the desired analyte, projecting the analyte's spectrum orthogonally away from the space spanned by the analyte-free calibration spectra, and normalizing the result to produce a unit response. Further description of embodiments of HLA techniques may be found in, for example, "Measurement of Analytes in Human Serum and Whole Blood Samples by Near-Infrared Raman Spectroscopy," Chapter 4, Andrew J. Berger, Ph. D. thesis, Massachusetts Institute of Technology, 1998, and "An Enhanced Algorithm for Linear Multivariate Calibration," by Andrew J. Berger, et al., Analytical Chemistry, Vol. 70, No. 3, Feb. 1, 1998, pp. 623-627, the entirety of each of which is hereby incorporated by reference herein. In other embodiments, the calibration coefficients may be calculated using other techniques including, for example, regression techniques such as, for example, ordinary least squares (OLS), partial least squares (PLS), and/or principal component analysis.

In block 2365, the processor 416 determines whether additional interferent subsets $\xi$ remain in the list of possible interferent subsets. If another subset is present in the list, the acts in blocks 2310-2360 are repeated for the next subset of interferents using different random concentrations. In some embodiments, blocks 2310-2360 are performed for only the most probable subset on the list.

The calibration coefficient determined in block 2360 corresponds to a single interferent subset $\xi$ from the list of possible interferent subsets and is denoted herein as a single-interferent-subset calibration coefficient $\kappa_{avg}(\xi)$. In this example method, after all subsets $\xi$ have been processed, the method continues in block 2370, in which the single-interferent-subset calibration coefficient is applied to the measured spectra $C_s$ to determine an estimated, single-interferent-subset analyte concentration, $g(\xi)=\kappa_{avg}(\xi)\cdot C_s$, for the interferent subset $\xi$. The set of the estimated, single-interferent-subset analyte concentrations $g(\xi)$ for all subsets in the list may be assembled into an array of single-interferent-subset concentrations. As noted above, in some embodiments the blocks 2310-2370 are performed once for the most probable single-interferent-subset on the list (e.g., the array of single-interferent analyte concentrations has a single member).

Returning to block 2140 of FIG. 21, the array of single-interferent-subset concentrations, $g(\xi)$, is combined to determine an estimated analyte concentration, $g_{est}$, for the material sample. In certain embodiments, a weighting function $p(\xi)$ is determined for each of the interferent subsets $\xi$ on the list of possible interferent subsets. The weighting functions may be normalized such that $\Sigma p(\xi)=1$, where the sum is over all subsets $\xi$ that have been processed from the list of possible interferent subsets. In some embodiments, the weighting functions can be related to the minimum Mahalanobis distance or an optimal concentration. In certain embodiments, the weighting function $p(\xi)$, for each subset $\xi$, is selected to be a constant, e.g., $1/N_S$ where $N_S$ is the number of subsets processed from the list of possible interferent subsets. In other embodiments, other weighting functions $p(\xi)$ can be selected.

In certain embodiments, the estimated analyte concentration, $g_{est}$, is determined (in block 2140) by combining the single-interferent-subset estimates, $g(\xi)$, and the weighting functions, $p(\xi)$, to generate an average analyte concentration. The average concentration may be computed according to $g_{est}=\Sigma g(\xi)\, p(\xi)$, where the sum is over the interferent subsets processed from the list of possible interferent subsets. In some embodiments, the weighting function $p(\xi)$ is a constant value for each subset (e.g., a standard arithmetic average is used for determining average analyte concentration). By testing the above described example method on simulated data, it has been found that the average analyte concentration advantageously has errors that may be reduced in comparison to other methods (e.g., methods using only a single most probable interferent).

Although the flowchart in FIG. 21 schematically illustrates an embodiment of the method 2100 performed with reference to the blocks 2110-2140 described herein, in other embodiments, the method 2100 can be performed differently. For example, some or all of the blocks 2110-2140 can be combined, performed in a different order than shown, and/or the functions of particular blocks may be reallocated to other blocks and/or to different blocks. Embodiments of the method 2100 may utilize different blocks than are shown in FIG. 21.

For example, in some embodiments of the method 2100, the calibration coefficient is computed without synthesizing spectra and/or partitioning the data into calibration sets and test sets. Such embodiments are referred to herein as "Parameter-Free Interferent Rejection" (PFIR) methods. In one example embodiment using PFIR, for each of the possible interferent subsets $\xi$, the following calculations may be performed to compute an estimate of a calibration coefficient for each subset $\xi$. An average concentration may be estimated according to $g_{est}=\Sigma g(\xi) p(\xi)$, where the sum is over the interferent subsets processed from the list of possible interferent subsets.

An example of an alternative embodiment of block 2130 includes the following steps and calculations.

Step 1: For a subset's $N_{IF}$ interferents, form a scaled interferent spectra matrix. In certain embodiments, the scaled interferent spectra matrix is the product of an interferent spectral matrix, IF, multiplied by an interferent concentration matrix, $T_{max}$, and can be written as: IF $T_{max}$. In certain such embodiments, the interferent concentration matrix $T_{max}$ is a diagonal matrix having entries given by the maximum plasma concentrations for the various interferents.

Step 2: Calculate a covariance for the interferent component. If X denotes the IESD, the covariance of X, cov(X), is defined as the expectation $E((X-\text{mean}(X))(X-\text{mean}(X))^T)$ and is $$\text{cov}(X) \approx XX^T/(N-1)-\text{mean}(X)\text{mean}(X)^T.$$

As described above, the IESD (e.g., X) is obtained as a combination of Sample Population Spectra, C, with Combination Interferent Spectra (CIS): $X_j=C_j+IF_j\xi_j$, therefore the covariance is:

$$\text{cov}(X) \approx CC^T/(N-1)+IF\Xi\Xi^T IF^T/(N-1)-\text{mean}(X)\text{mean}(X)^T,$$

which can be written as, $$\text{cov}(X) \approx \text{cov}(C)+IF\,\text{cov}(\Xi)IF^T.$$

If the weights in the weighting matrix $\Xi$ are independent and identically distributed, the covariance of $\Xi$, cov($\Xi$), is a diagonal matrix having along the diagonal the variance, v, of the samples in $\Xi$. The last equation may be written as $$\text{cov}(X) \approx V_0+v\Phi,$$

where $V_0$ is the covariance of the original sample population and $\Phi$ is the covariance of the IF spectral set.

Step 3: The group's covariance may be at least partially corrected for the presence of a single replicate of the Sample Population spectra with the IESD as formed from $N_{IF}$ replicates of the Sample Population Spectra with Combined Interferent Spectra. This partial correction may be achieved by multiplying the second term in the covariance formula given above by a correction factor $\rho$:

$$V=V_0+\rho v\Phi,$$

where $\rho$ is a scalar weighting function that depends on the number of interferents in the group. In some embodiments, the scalar weighting function is $\rho=N_{IF}/(N_{IF}+1)$. In certain embodiments, the variance v of the weights is assumed to be the variance of a log-normal random variable having a 95th percentile at a value of 1.0, and a standard deviation equal to half of the mean value.

Step 4: The eigenvectors and the corresponding eigenvalues of the covariance matrix V are determined using any suitable linear algebraic methods. The number of eigenvectors (and eigenvalues) is equal to the number of wavelengths L in the spectral measurements. The eigenvectors may be sorted based on decreasing order of their corresponding eigenvalues.

Step 5: The matrix of eigenvectors is decomposed so as to provide an orthogonal matrix Q. For example, in some embodiments, a QR-decomposition is performed, thereby yielding the matrix Q having orthonormal columns and rows.

Step 6: The following matrix operations are performed on the orthogonal matrix Q. For n=2 to L−1, the product $P^{\parallel}_n=Q(:,1:n)\,Q(:,1:n)^T$ is calculated, where Q(:,1:n) denotes the submatrix comprising the first n columns of the full matrix Q. The orthogonal projection, $P^{\perp}_n$, away from the space spanned by Q(:,1:n) is determined by subtracting $P^{\parallel}_n$ from the L×L identity matrix I. The $n^{th}$ calibration vector is then determined from $\kappa_n=P^{\perp}_n\alpha_X\alpha_X^T P^{\perp}_n\alpha_X$, and the $n^{th}$ error variance $E_n$ is determined as the projection of the full covariance V onto the subspace spanned by $\kappa_n$ as follows: $E_n=\kappa_n^T V\kappa_n$.

The steps 4-6 of this example are an embodiment of the HLA technique.

In some embodiments, the calibration coefficient $\kappa$ is selected as the calibration vector corresponding to the minimum error variance $E_n$. Thus, for example, the average group calibration coefficient $\kappa$ may be found by searching among all the error variances for the error variance $E_n$ that has the minimum value. The calibration coefficient is then selected as the $n^{th}$ calibration vector $\kappa_n$ corresponding to the minimum error variance $E_n$. In other embodiments, the calibration coefficient is determined by averaging some or all of the calibration vectors $\kappa_n$.

Examples of Algorithm Results and Effects of Sample Population

Embodiments of the above-described methods have been used to estimate blood plasma glucose concentrations in humans. Four example experiments will now be described. The population of individuals from whom samples were obtained for analysis (estimation of glucose concentration) will be referred to as the "target population." Infrared spectra obtained from the target population will be referred to as the "target spectra." In the four example experiments, the target population included 41 intensive care unit (ICU) patients. Fifty-five samples were obtained from the target population.

Example Experiment 1

In this example experiment, a partial least squares (PLS) regression method was applied to the infrared target spectra of the target patients' blood plasma to obtain the glucose estimates. In example experiment 1, estimated glucose concentration was not corrected for effects of interferents. The Sample Population used for the analysis included infrared spectra and independently measured glucose concentrations for 92 individuals selected from the general population. This Sample Population will be referred to as a "Normal Population."

Example Experiment 2

In example experiment 2, an embodiment of the Parameter-Free Interferent Rejection (PFIR) method was used to estimate glucose concentration for the same target population of patients in example experiment 1. The Sample Population was the Normal Population. In this example, calibration for Library Interferents was applied to the measured target spectra. The Library of Interferents included spectra of the 59 substances listed below:

Acetylsalicylic Acid
Ampicillin Sulbactam
Azithromycin
Aztreonam
Bacitracin

-continued

Benzyl Alcohol
Calcium Chloride
Calcium Gluconate
Cefazolin
Cefoparazone
Cefotaxime Sodium
Ceftazidime
Ceftriaxone
D_Sorbitol
Dextran
Ertapenem
Ethanol
Ethosuximide
Glycerol
Heparin
Hetastarch
Human Albumin
Hydroxy Butyric Acid
Imipenem Cilastatin
Iohexol
L_Arginine
Lactate Sodium
Magnesium Sulfate
Maltose
Mannitol
Meropenem
Oxylate Potassium
Phenytoin
Phosphates Potassium
Piperacillin
Piperacillin Tazobactam
PlasmaLyteA
Procaine HCl
Propylene Glycol
Pyrazinamide
Pyruvate Sodium
Pyruvic Acid
Salicylate Sodium
Sodium Acetate
Sodium Bicarbonate
Sodium Chloride
Sodium Citrate
Sodium Thiosulfate
Sulfadiazine
Urea
Uric Acid
Voriconazole
Xylitol
Xylose
PC 1 of Saline covariance
PC 2 of Saline covariance
PC 3 of Saline covariance
PC 4 of Saline covariance
ICU/Normal difference spectrum In some embodiments, the calibration data set is determined according to two criteria: the calibration method itself (e.g., HLA, PLS, OLS, PFIR) and the intended application of the method. The calibration data set may comprise spectra and corresponding analyte levels derived from a set of plasma samples from the Sample Population. In some embodiments, e.g., those where an HLA calibration method is used, the calibration data set may also include spectra of the analyte of interest.

In the example experiments 1 and 2, the Sample Population was the Normal Population. Thus, samples were drawn from a population of normal individuals who did not have identifiable medical conditions that might affect the spectra of their plasma samples. For example, the sample plasma spectra typically did not show effects of high levels of medications or other substances (e.g., ethanol), or effects of chemicals that are indicative of kidney or liver malfunction.

In some embodiments, an analysis method may calibrate for deviations from the distribution defined by the calibration plasma spectra by identifying a "base" set of interferent spectra likely to be responsible for the deviation. The analysis method may then recalibrate with respect to an enhanced spectral data set. In some embodiments, the enhancement can be achieved by including the identified interferent spectra into the calibration plasma spectra. When it is anticipated that the target population may have been administered significant amounts of substances not present in the samples of the calibration set, or when the target population have many distinct interferents, estimation of the interferents present in the target spectrum may be subject to a large degree of uncertainty. In some cases, this may cause analyte estimation to be subject to errors.

Accordingly, in certain embodiments, the calibration data set may be enhanced beyond the base of "normal" samples to include a population of samples intended to be more representative of the target population. The enhancement of the calibration set may be generated, in some embodiments, by including samples from a sufficiently diverse range of individuals in order to represent the range of likely interferents (both in type and in concentration) and/or the normal variability in underlying plasma characteristics. The enhancement may, additionally or alternatively, be generated by synthesizing interferent spectra having a range of concentrations as described above (see, e.g., discussion of block 2310 in FIG. 23). Using the enhanced calibration set may reduce the error in estimating the analyte concentration in the target spectra.

Example Experiments 3 and 4

Example experiments 3 and 4 use the analysis methods of example experiments 1 and 2, respectively (PLS without interferent correction and PFIR with interferent correction). However, example experiments 3 and 4 use a Sample Population having blood plasma spectral characteristics different from the Normal Population used in example experiments 1 and 2. In example experiments 3 and 4, the Sample Population was modified to include spectra of both the Normal Population and spectra of an additional population of 55 ICU patients. These spectra will be referred to as the "Normal+Target Spectra." In experiments 3 and 4, the ICU was a major trauma center, and the ICU patients were victims of severe trauma, including a large proportion of patients who had suffered major blood loss. Major blood loss may necessitate replacement of the patient's total blood volume multiple times during a single day and subsequent treatment of the patient via electrolyte and/or fluid replacement therapies. Major blood loss may also require administration of plasma-expanding medications. Major blood loss may lead to significant deviations from the blood plasma spectra representative of a Normal Population. The population of 55 ICU patients (who provided the Target Spectra) has some similarities to the individuals for whom the analyses in experiments 1-4 were performed (e.g., all were ICU patients), but in these experiments, target spectra from individuals in the target population were not included in the Target Spectra.

Results of example experiments 1-4 are shown in the following table. The glucose concentrations estimated from the analysis method were compared to independently determined glucose measurements to provide an average prediction error and a standard deviation of the average prediction error. The table demonstrates that independent of the Sample Population used (e.g., either the Normal Population or the Normal+Target Population), calibrating for interferents reduces both the average prediction error and the standard deviation (e.g., compare the results for experiment 2 to the results for experiment 1 and compare the results for experiment 4 to the results for experiment 3). The table further demonstrates that independent of the analysis method used (e.g., either PLS or PFIR), using a Sample Population with more similarity to the target population (e.g., the Normal+ Target Population) reduces both the average prediction error and the standard deviation (e.g., compare the results for experiment 3 to the results for experiment 1 and compare the results for experiment 4 to the results for experiment 2).

| Example Experiment No. | Interferent Calibration | Sample Population | Average Prediction Error (mg/dL) | Standard Deviation (mg/dL) |
|---|---|---|---|---|
| 1 | NO | Normal | 126 | 164 |
| 2 | YES | Normal | −6.8 | 23.2 |
| 3 | NO | Normal + Target | 8.2 | 16.9 |
| 4 | YES | Normal + Target | 1.32 | 12.6 |

Accordingly, embodiments of analysis methods that use a Sample Population that includes both normal spectra and spectra from individuals similar to those of the target population and that calibrate for possible interferents provide a good match between the estimated glucose concentration and the measured glucose concentration.

User Interface

The system 400 can include a display system 414, for example, as depicted in FIG. 4. The display system 414 may comprise an input device including, for example, a keypad or a keyboard, a mouse, a touchscreen display, and/or any other suitable device for inputting commands and/or information. The display system 414 may also include an output device including, for example, an LCD monitor, a CRT monitor, a touchscreen display, a printer, and/or any other suitable device for outputting text, graphics, images, videos, etc. In some embodiments, a touchscreen display is advantageously used for both input and output.

The display system 414 can include a user interface 2400 by which users can conveniently and efficiently interact with the system 400. The user interface 2400 may be displayed on the output device of the system 400 (e.g., the touchscreen display). In some embodiments, the user interface 2400 is implemented and/or stored as one or more code modules, which may be embodied in hardware, firmware, and/or software.

FIGS. 24 and 25 schematically illustrate the visual appearance of embodiments of the user interface 2400. The user interface 2400 may show patient identification information 2402, which can include patient name and/or a patient ID number. The user interface 2400 also can include the current date and time 2404. An operating graphic 2406 shows the operating status of the system 400. For example, as shown in FIGS. 24 and 25, the operating status is "Running," which indicates that the system 400 is fluidly connected to the patient ("Jill Doe") and performing normal system functions such as infusing fluid and/or drawing blood. The user interface 2400 can include one or more analyte concentration graphics 2408, 2412, which may show the name of the analyte and its last measured concentration. For example, the graphic 2408 in FIG. 24 shows "Glucose" concentration of 150 mg/dL, while the graphic 2412 shows "Lactate" concentration of 0.5 mmol/L. The particular analytes displayed and their measurement units (e.g., mg/dL, mmol/L, or other suitable unit) may be selected by the user. The size of the graphics 2408, 2412 may be selected to be easily readable out to a distance such as, e.g., 30 feet. The user interface 2400 may also include a next-reading graphic 2410 that indicates the time until the next analyte measurement is to be taken. In FIG. 24, the time until next reading is 3 minutes, whereas in FIG. 25, the time is 6 minutes, 13 seconds.

The user interface 2400 can include an analyte concentration status graphic 2414 that indicates status of the patient's current analyte concentration compared with a reference standard. For example, the analyte may be glucose, and the reference standard may be a hospital ICU's tight glycemic control (TGC). In FIG. 24, the status graphic 2414 displays "High Glucose," because the glucose concentration (150 mg/dL) exceeds the maximum value of the reference standard. In FIG. 25, the status graphic 2414 displays "Low Glucose," because the current glucose concentration (79 mg/dL) is below the minimum reference standard. If the analyte concentration is within bounds of the reference standard, the status graphic 2414 may indicate normal (e.g., "Normal Glucose"), or it may not be displayed at all. The status graphic 2414 may have a background color (e.g., red) when the analyte concentration exceeds the acceptable bounds of the reference standard.

The user interface 2400 can include one or more trend indicators 2416 that provide a graphic indicating the time history of the concentration of an analyte of interest. In FIGS. 24 and 25, the trend indicator 2416 comprises a graph of the glucose concentration (in mg/dL) versus elapsed time (in hours) since the measurements started. The graph includes a trend line 2418 indicating the time-dependent glucose concentration. In other embodiments, the trend line 2418 can include measurement error bars and may be displayed as a series of individual data points. In FIG. 25, the glucose trend indicator 2416 is shown as well as a trend indicator 2430 and trend line 2432 for the lactate concentration. In some embodiments, a user may select whether none, one, or both trend indicators 2416, 2418 are displayed. In some embodiments, one or both of the trend indicators 2416, 2418 may appear only when the corresponding analyte is in a range of interest such as, for example, above or below the bounds of a reference standard.

The user interface 2400 can include one or more buttons 2420-2426 that can be actuated by a user to provide additional functionality or to bring up suitable context-sensitive menus and/or screens. For example, in the embodiments shown in FIG. 24 and FIG. 25, four buttons 2420-2426 are shown, although fewer or more buttons are used in other embodiments. The button 2420 ("End Monitoring") may be pressed when one or more removable portions (see, e.g., 710 of FIG. 7) are to be removed. In many embodiments, because the removable portions 710, 712 are not reusable, a confirmation window appears when the button 2420 is pressed. If the user is certain that monitoring should stop, the user can confirm this by actuating an affirmative button in the confirmation window. If the button 2420 were pushed by mistake, the user can select a negative button in the confirmation window. If "End Monitoring" is confirmed, the system 400 performs appropriate actions to cease fluid infusion and blood draw and to permit ejection of a removable portion (e.g., the removable portion 710).

The button 2422 ("Pause") may be actuated by the user if patient monitoring is to be interrupted but is not intended to end. For example, the "Pause" button 2422 may be actuated if the patient is to be temporarily disconnected from the system 400 (e.g., by disconnecting the tubes 306). After the patient is reconnected, the button 2422 may be pressed again to resume monitoring. In some embodiments, after the "Pause" button 2422 has been pressed, the button 2422 displays "Resume."

The button 2424 ("Delay 5 Minutes") causes the system 400 to delay the next measurement by a delay time period (e.g., 5 minutes in the depicted embodiments). Actuating the delay button 2424 may be advantageous if taking a reading would be temporarily inconvenient, for example, because a health care professional is attending to other needs of the patient. The delay button 2424 may be pressed repeatedly to provide longer delays. In some embodiments, pressing the delay button 2424 is ineffective if the accumulated delay exceeds a maximum threshold. The next-reading graphic 2410 automatically increases the displayed time until the next reading for every actuation of the delay button 2424 (up to the maximum delay).

The button 2426 ("Dose History") may be actuated to bring up a dosing history window that displays patient dosing history for an analyte or medicament of interest. For example, in some embodiments, the dosing history window displays insulin dosing history of the patient and/or appropriate hospital dosing protocols. A nurse attending the patient can actuate the dosing history button 2426 to determine the time when the patient last received an insulin dose, the last dosage amount, and/or the time and amount of the next dosage. The system 400 may receive the patient dosing history via wired or wireless communications from a hospital information system.

In other embodiments, the user interface 2400 can include additional and/or different buttons, menus, screens, graphics, etc. that are used to implement additional and/or different functionalities.

Related Components

Figure 26:
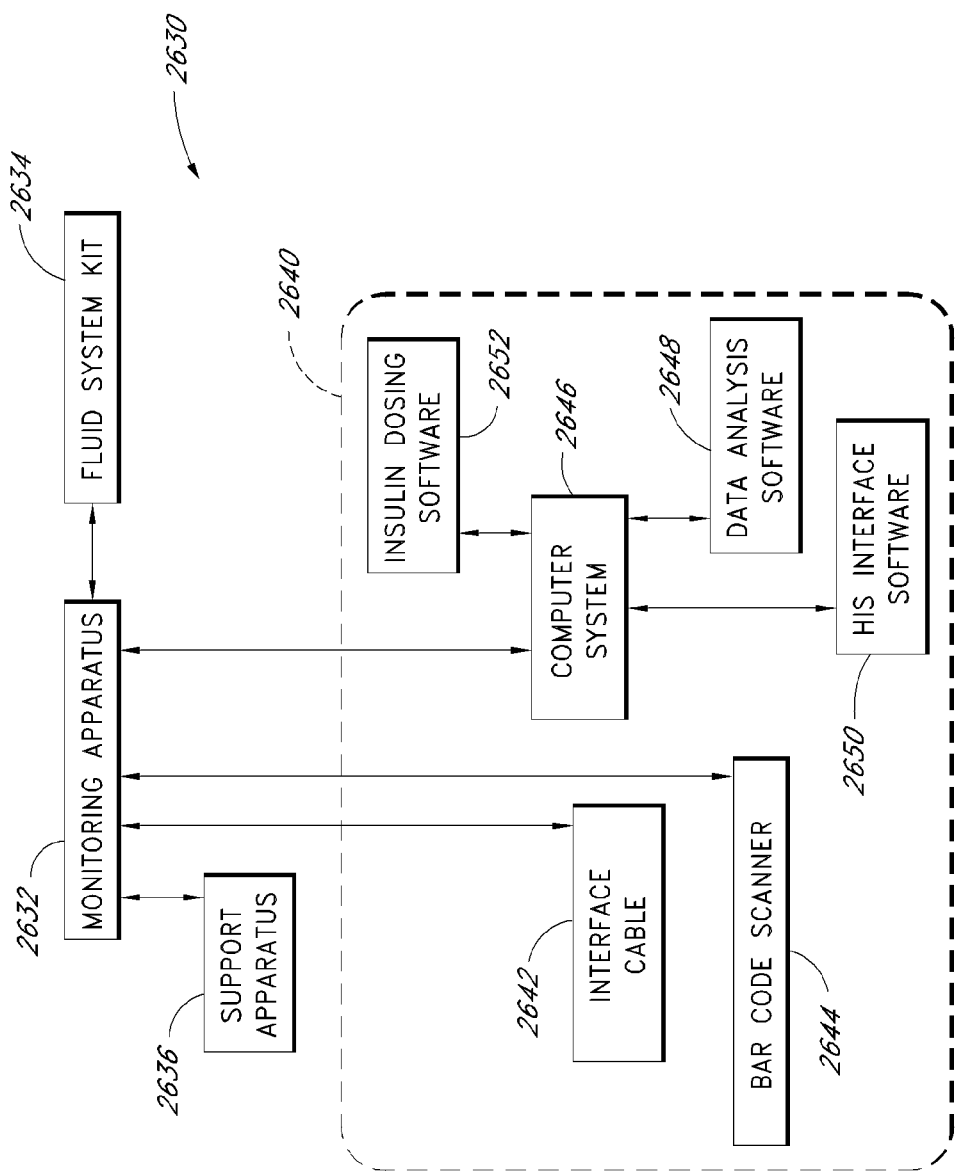
FIG. 26 schematically depicts various components and/or aspects of a patient monitoring system and the relationships among the components and/or aspects.

FIG. 26 schematically depicts various components and/or aspects of a patient monitoring system 2630 and how those components and/or aspects relate to each other. In some embodiments, the monitoring system 2630 can be the apparatus 100 for withdrawing and analyzing fluid samples. Some of the depicted components can be included in a kit containing a plurality of components. Some of the depicted components, including, for example, the components represented within the dashed rounded rectangle 2640 of FIG. 26, are optional and/or can be sold separately from other components.

The patient monitoring system 2630 shown in FIG. 26 includes a monitoring apparatus 2632. The monitoring apparatus 2632 can be the monitoring device 102, shown in FIG. 1 and/or the system 400 of FIG. 4. The monitoring apparatus 2632 can provide monitoring of physiological parameters of a patient. In some embodiments, the monitoring apparatus 2632 measures glucose and/or lactate concentrations in the patient's blood. In some embodiments, the measurement of such physiological parameters is substantially continuous. The monitoring apparatus 2632 may also measure other physiological parameters of the patient. In some embodiments, the monitoring apparatus 2632 is used in an intensive care unit (ICU) environment. In some embodiments, one monitoring apparatus 2632 is allocated to each patient room in an ICU.

The patient monitoring system 2630 can include an optional interface cable 2642. In some embodiments, the interface cable 2642 connects the monitoring apparatus 2632 to a patient monitor (not shown). The interface cable 2642 can be used to transfer data from the monitoring apparatus 2632 to the patient monitor for display. In some embodiments, the patient monitor is a bedside cardiac monitor having a display that is located in the patient room (see, e.g., the user interface 2400 shown in FIG. 24 and FIG. 25.) In some embodiments, the interface cable 2642 transfers data from the monitoring apparatus 2632 to a central station monitor and/or to a hospital information system (HIS). The ability to transfer data to a central station monitor and/or to a HIS may depend on the capabilities of the patient monitor system.

In the embodiment shown in FIG. 26, an optional bar code scanner 2644 is connected to the monitoring apparatus 2632. In some embodiments, the bar code scanner 2644 is used to enter patient identification codes, nurse identification codes, and/or other identifiers into the monitoring apparatus 2632. In some embodiments, the bar code scanner 2644 contains no moving parts. The bar code scanner 2644 can be operated by manually sweeping the scanner 2644 across a printed bar code or by any other suitable means. In some embodiments, the bar code scanner 2644 includes an elongated housing in the shape of a wand.

The patient monitoring system 2630 includes a fluid system kit 2634 connected to the monitoring apparatus 2632. In some embodiments, the fluid system kit 2634 includes fluidic tubes that connect a fluid source to an analytic subsystem. For example, the fluidic tubes can facilitate fluid communication between a blood source or a saline source and an assembly including a sample holder and/or a centrifuge. In some embodiments, the fluid system kit 2634 includes many of the components that enable operation of the monitoring apparatus 2632. In some embodiments, the fluid system kit 2634 can be used with anti-clotting agents (such as heparin), saline, a saline infusion set, a patient catheter, a port sharing IV infusion pump, and/or an infusion set for an IV infusion pump, any or all of which may be made by a variety of manufacturers. In some embodiments, the fluid system kit 2634 includes a monolithic housing that is sterile and disposable. In some embodiments, at least a portion of the fluid system kit 2634 is designed for single patient use. For example, the fluid system kit 2634 can be constructed such that it can be economically discarded and replaced with a new fluid system kit 2634 for every new patient to which the patient monitoring system 2630 is connected. In addition, at least a portion of the fluid system kit 2634 can be designed to be discarded after a certain period of use, such as a day, several days, several hours, three days, a combination of hours and days such as, for example, three days and two hours, or some other period of time. Limiting the period of use of the fluid system kit 2634 may decrease the risk of malfunction, infection, or other conditions that can result from use of a medical apparatus for an extended period of time.

In some embodiments, the fluid system kit 2634 includes a connector with a luer fitting for connection to a saline source. The connector may be, for example, a three-inch pigtail connector. In some embodiments, the fluid system kit 2634 can be used with a variety of spikes and/or IV sets used to connect to a saline bag. In some embodiments, the fluid system kit 2634 also includes a three-inch pigtail connector with a luer fitting for connection to one or more IV pumps. In some embodiments, the fluid system kit 2634 can be used with one or more IV sets made by a variety of manufacturers, including IV sets obtained by a user of the fluid system kit 2634 for use with an infusion pump. In some embodiments, the fluid system kit 2634 includes a tube with a low dead volume luer connector for attachment to a patient vascular access point. For example, the tube can be approximately seven feet in length and can be configured to connect to a proximal port of a cardiovascular catheter. In some embodiments, the fluid system kit 2634 can be used with a variety of cardiovascular catheters, which can be supplied, for example, by a user of the fluid system kit 2634.

As shown in FIG. 26, the monitoring apparatus 2632 is connected to a support apparatus 2636, such as an IV pole. The support apparatus 2636 can be customized for use with the monitoring apparatus 2632. A vendor of the monitoring apparatus 2632 may choose to bundle the monitoring apparatus 2632 with a custom support apparatus 2636. In some embodiments, the support apparatus 2636 includes a mounting platform for the monitoring apparatus 2632. The mounting platform can include mounts that are adapted to engage threaded inserts in the monitoring apparatus 2632. The support apparatus 2636 can also include one or more cylindrical sections having a diameter of a standard IV pole, for example, so that other medical devices, such as IV pumps, can be mounted to the support apparatus. The support apparatus 2636 can also include a clamp adapted to secure the apparatus to a hospital bed, an ICU bed, or another variety of patient conveyance device.

In the embodiment shown in FIG. 26, the monitoring apparatus 2632 is electrically connected to an optional computer system 2646. The computer system 2646 can comprise one or multiple computers, and it can be used to communicate with one or more monitoring devices. In an ICU environment, the computer system 2646 can be connected to at least some of the monitoring devices in the ICU. The computer system 2646 can be used to control configurations and settings for multiple monitoring devices (for example, the system can be used to keep configurations and settings of a group of monitoring devices common). The computer system 2646 can also run optional software, such as data analysis software 2648, HIS interface software 2650, and insulin dosing software 2652.

In some embodiments, the computer system 2646 runs optional data analysis software 2648 that organizes and presents information obtained from one or more monitoring devices. In some embodiments, the data analysis software 2648 collects and analyzes data from the monitoring devices in an ICU. The data analysis software 2648 can also present charts, graphs, and statistics to a user of the computer system 2646.

In some embodiments, the computer system 2646 runs optional hospital information system (HIS) interface software 2650 that provides an interface point between one or more monitoring devices and an HIS. The HIS interface software 2650 may also be capable of communicating data between one or more monitoring devices and a laboratory information system (LIS).

In some embodiments, the computer system 2646 runs optional insulin dosing software 2652 that provides a platform for implementation of an insulin dosing regimen. In some embodiments, the hospital tight glycemic control protocol is included in the software. The protocol allows computation of proper insulin doses for a patient connected to a monitoring device 2646. The insulin dosing software 2652 can communicate with the monitoring device 2646 to ensure that proper insulin doses are calculated.

Analyte Control and Monitoring

In some embodiments, it may be advantageous to control a level of an analyte (e.g., glucose) in a patient using an embodiment of an analyte detection system described herein. Although certain examples of glucose control are described below, embodiments of the systems and methods disclosed herein may be used to monitor and/or control other analytes (e.g., lactate).

For example, diabetic individuals control their glucose levels by administration of insulin. If a diabetic patient is admitted to a hospital or ICU, the patient may be in a condition in which he or she cannot self-administer insulin. Advantageously, embodiments of the analyte detection systems disclosed herein may be used to control the level of glucose in the patient. Additionally, it has been found that a majority of patients admitted to the ICU exhibit hyperglycemia without having diabetes. In such patients it may be beneficial to monitor and control their blood glucose level to be within a particular range of values. Further, it has been shown that tightly controlling blood glucose levels to be within a stringent range may be beneficial to patients undergoing surgical procedures.

A patient admitted to the ICU or undergoing surgery may be administered a variety of drugs and fluids such as Hetastarch, intravenous antibiotics, intravenous glucose, intravenous insulin, intravenous fluids such as saline, etc., which may act as interferents and make it difficult to determine the blood glucose level. Moreover, the presence of additional drugs and fluids in the blood stream may require different methods for measuring and controlling blood glucose level. Also, the patient may exhibit significant changes in hematocrit levels due to blood loss or internal hemorrhage, and there can be unexpected changes in the blood gas level or a rise in the level of bilirubin and ammonia levels in the event of an organ failure. Embodiments of the systems and methods disclosed herein advantageously may be used to monitor and control blood glucose (and/or other analytes) in the presence of possible interferents to estimation of glucose and for patients experiencing health problems.

In some environments, Tight Glycemic Control (TGC) can be achieved by controlling glucose within a relatively narrow range (for example between 70 mg/dL to 110 mg/dL). As will be further described, in some embodiments, TGC may be achieved by using an analyte monitoring system to make continuous and/or periodic but frequent measurements of glucose levels.

In some embodiments, the analyte detection system schematically illustrated in FIGS. 4, 5, and 6 may be used to regulate the concentration of one or more analytes in the sample in addition to determining and monitoring the concentration of the one or more analytes. In some implementations, the concentration of the analytes is regulated to be within a certain range. The range may be predetermined (e.g., according to a hospital protocol or a physician's recommendation), or the range may be adjusted as conditions change.

In an example of glycemic control, a system can be used to determine and monitor the concentration of glucose in the sample. If the concentration of glucose falls below a lower threshold, glucose from an external source can be supplied. If the concentration of glucose increases above an upper threshold, insulin from an external source can be supplied. In some embodiments, glucose or insulin may be infused in a patient continuously over a certain time interval or may be injected in a large quantity at once (referred to as "bolus injection").

In some embodiments, a glycemic control system may be capable of delivering glucose, dextrose, glycogen, and/or glucagon from an external source relatively quickly in the event of hypoglycemia. As discussed, embodiments of the glycemic control system may be capable of delivering insulin from an external source relatively quickly in the event of hyperglycemia.

Returning to FIGS. 5 and 6, these figures schematically illustrate embodiments of a fluid handling system that comprise optional analyte control subsystems 2780. The analyte control subsystem 2780 may be used for providing control of an analyte such as, e.g., glucose, and may provide delivery of the analyte and/or related substances (e.g., dextrose solution and/or insulin in the case of glucose). The analyte control subsystem 2780 comprises a source 2782 such as, for example, the analyte (or a suitable compound related to the analyte) dissolved in water or saline. For example, if the analyte is glucose, the source 2782 may comprise a bag of dextrose solution (e.g., Dextrose or Dextrose 50%). The source 2782 can be coupled to an infusion pump (not shown). The source 2782 and the infusion pump can be provided separately from the analyte control subsystem 2780. For example, a hospital advantageously can use existing dextrose bags and infusion pumps with the subsystem 2780.

As schematically illustrated in FIGS. 5 and 6, the source 2782 is in fluid communication with the patient tube 512 via a tube 2784 and suitable connectors. A pinch valve 2786 may be disposed adjacent the tube 2784 to regulate the flow of fluid from the source 2782. A patient injection port can be located at a short distance from the proximal port of the central venous catheter or some other catheter connected to the patient.

In an example implementation for glycemic control, if the analyte detection system determines that the level of glucose has fallen below a lower threshold value (e.g., the patient is hypoglycemic), a control system (e.g., the fluid system controller 405 in some embodiments) controlling an infusion delivery system may close the pinch valves 521 and/or 542 to prevent infusion of insulin and/or saline into the patient. The control system may open the pinch valve 2786 and dextrose solution from the source 2782 can be infused (or alternatively injected as a bolus) into the patient. After a suitable amount of dextrose solution has been infused to the patient, the pinch valve 2786 can be closed, and the pinch valves 521 and/or 542 can be opened to allow flow of insulin and/or saline. In some systems, the amount of dextrose solution for infusion (or bolus injection) may be calculated based on one or more detected concentration levels of glucose. The source 2782 advantageously may be located at a short enough fluidic distance from the patient such that dextrose can be delivered to the patient within a time period of about one to about ten minutes. In other embodiments, the source 2782 can be located at the site where the patient tube 512 interfaces with the patient so that dextrose can be delivered within about one minute.

If the analyte detection system determines that the level of glucose has increased above an upper threshold value (e.g., the patient is hyperglycemic), the control system may close the pinch valves 542 and/or 2786 to prevent infusion of saline and/or dextrose into the patient. The control system may open the pinch valve 521, and insulin can be infused (or alternatively injected as a bolus) into the patient. After a suitable amount of insulin has been infused (or bolus injected) to the patient, the control system can close the pinch valve 521 and open the pinch valves 542 and/or 2786 to allow flow of saline and/or glucose. The suitable amount of insulin may be calculated based on one or more detected concentration levels of glucose in the patient. The insulin source 518 advantageously may be located at a short enough fluidic distance from the patient such that insulin can be delivered to the patient within about one to about ten minutes. In other embodiments, the insulin source 518 may be located at the site where the patient tube 512 interfaces with the patient so that insulin can be delivered to the patient within about one minute.

In some embodiments, sampling bodily fluid from a patient and providing medication to the patient may be achieved through the same lines of the fluid handling system. For example, in some embodiments, a port to a patient can be shared by alternately drawing samples and medicating through the same line. In some embodiments, a bolus can be provided to the patient at regular intervals (in the same or different lines). For example, a bolus of insulin can be provided to a patient after meals. In another embodiment comprising a shared line, a bolus of medication can be delivered when returning part of a body fluid sample back to the patient. In some implementations, the bolus of medication is delivered midway between samples (e.g., every 7.5 minutes if samples are drawn every 15 minutes). In other embodiment, a dual lumen tube can be used, wherein one lumen is used for the sample and the other lumen to medicate. In yet another embodiment, an analyte detection system (e.g., an "OptiScanner®" monitor) may provide suitable commands to a separate insulin pump (on a shared port or different line).

Example Method for Glycemic Control

Figure 27:
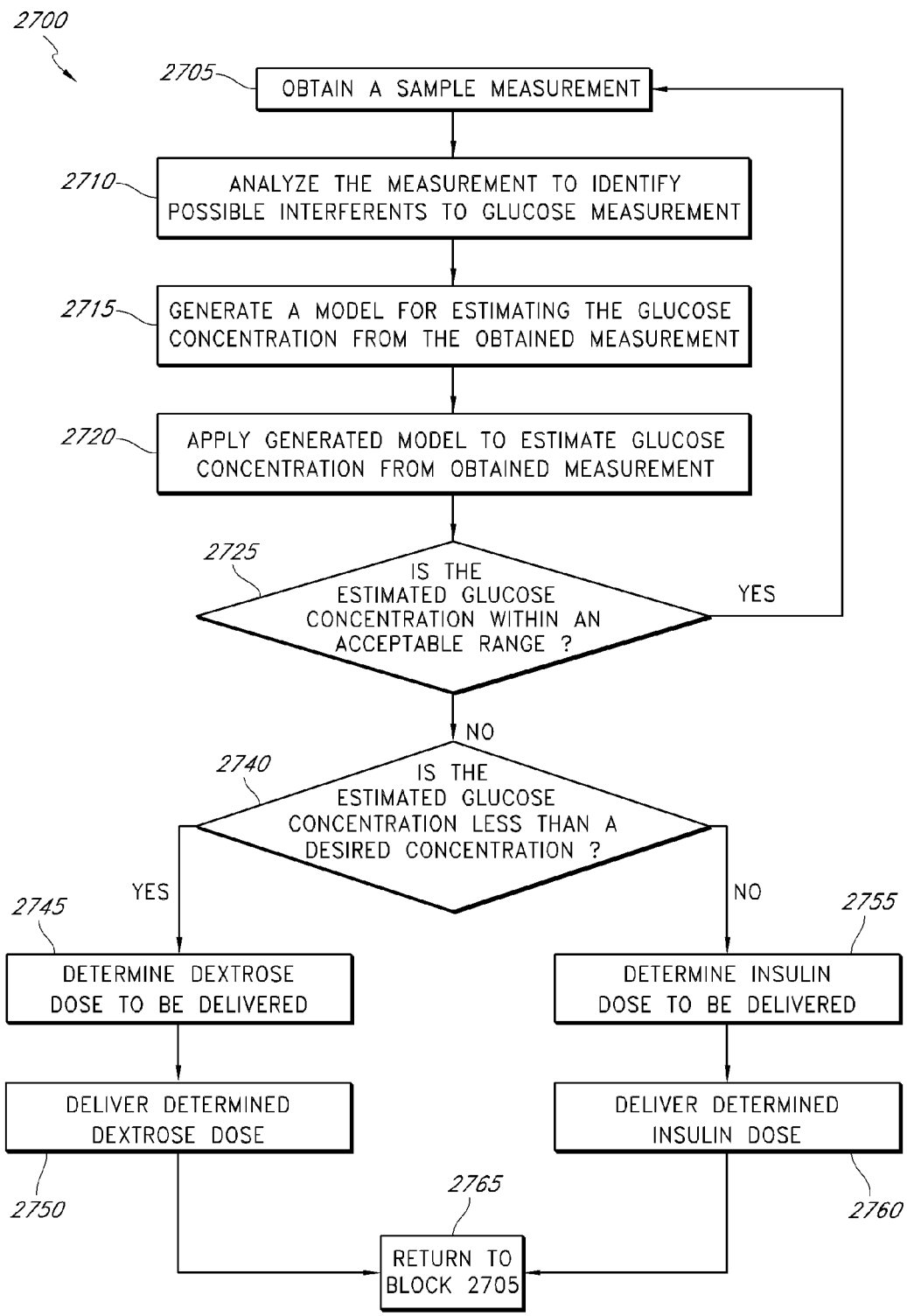
FIG. 27 is a flowchart that schematically illustrates an embodiment of a method of providing glycemic control.

FIG. 27 is a flowchart that schematically illustrates an example embodiment of a method 2700 of providing analyte control. The example embodiment is directed toward one possible implementation for glycemic control and is intended to illustrate certain aspects of the method 2700 and is not intended to limit the scope of possible analyte control methods. In block 2705, a glucose monitoring apparatus (e.g., the monitoring apparatus 2632 of FIG. 26) draws a sample (e.g., a blood or blood plasma sample) from a sample source (e.g., a patient) and obtains a measurement from the sample (e.g., a portion of the drawn sample). The measurement may comprise an optical measurement such as, for example, an infrared spectrum of the sample. In block 2710, the measurement sample is analyzed to identify possible interferents to an estimation of the glucose concentration in the measurement sample. In block 2715, a model is generated for estimating the glucose concentration from the obtained measurement. In some embodiments, models developed from the algorithms describe above with reference to FIGS. 21-23 are used. The generated model may reduce or minimize effects of the identified interferents on the estimated glucose concentration, in certain embodiments. In block 2720, an estimated glucose concentration is determined from the model and the obtained measurement. In block 2725, the estimated glucose concentration in the sample is compared to an acceptable range of concentrations. The acceptable range may be determined according to a suitable glycemic control protocol such as, for example, a TGC protocol. For example, in certain TGC protocols the acceptable range may be a glucose concentration in a range from about 70 mg/dL to about 110 mg/dL. If the estimated glucose concentration lies within the acceptable range, the method 2700 returns to block 2705 to obtain the next sample measurement, which may be made within about one to about thirty minutes (e.g., every fifteen minutes).

In block 2725, if the estimated glucose concentration is outside the acceptable range of concentrations, then the method 2700 proceeds to block 2740 in which the estimated glucose concentration is compared with a desired glucose concentration. The desired glucose concentration may be based on, for example, the acceptable range of glucose concentrations, the parameters of the particular glycemic protocol, the patient's estimated glucose concentration, and so forth. If the estimated glucose concentration is below the desired concentration (e.g., the patient is hypoglycemic), a dose of dextrose to be delivered to the patient is calculated in block 2745. This calculation may take into account various factors including, for example, one or more estimated glucose concentrations, presence of additional drugs in the patient's system, time taken for dextrose to be assimilated by the patient, and the delivery method (e.g., continuous infusion or bolus injection). In block 2750, a fluid delivery system (e.g., a system such as the optional subsystem 2780 shown in FIGS. 5 and 6) delivers the calculated dose of dextrose to the patient.

In block 2740, if the estimated glucose concentration is greater than the desired concentration (e.g., the patient is hyperglycemic), a dose of insulin to be delivered is calculated in block 2755. The dose of insulin may depend on various factors including, for example, one or more estimated glucose concentrations in the patient, presence of other drugs, type of insulin used, time taken for insulin to be assimilated by the patient, method of delivery (e.g., continuous infusion or bolus injection), etc. In block 2750, a fluid delivery system (e.g., the optional subsystem 2780 shown in FIGS. 5 and 6) delivers the calculated dose of insulin to the patient.

In block 2765, the method 2700 returns to block 2705 to await the start of the next measurement cycle, which may be within about one to about thirty minutes (e.g., every fifteen minutes). In some embodiments, the next measurement cycle begins at a different time than normally scheduled in cases in which the estimated glucose concentration lies outside the acceptable range of concentrations under the glycemic protocol. Such embodiments advantageously allow the system to monitor response of the patient to the delivered dose of dextrose (or insulin). In some such embodiments, the time between measurement cycles is reduced so the system can more accurately monitor analyte levels in the patient.

Anticoagulant Injection and Risk Mitigation

It can be useful to use anticoagulants to help prevent deposits from building up in fluid systems, especially those that contain bodily fluids such as blood. For example, heparin can be injected into a fluid system for blood as a means of preventing blood coagulation over time. The apparatus, systems, and methods described above (e.g., the monitoring device 102 of FIG. 1 and/or the system 400 for sampling and analyzing fluid samples of FIG. 4) can include passages having fluid flow (e.g., blood flow). In some embodiments, as noted above, a medical device having fluid flowing through it can comprise the "OptiScanner," available from OptiScan Biomedical Corporation of Hayward, Calif. In some embodiments, the device is a vascular connected continuous blood analyzer that measures analytes in the blood, such as glucose. Such devices, and other medical devices, can use anticoagulants (e.g., heparin) to prevent internal blood clotting.

In some embodiments, heparin can be provided by the hospital and can be packaged for normal patient use in vials fitted with a septum intended to be pierced by a syringe needle. Heparin can be drawn from normal hospital stock and loaded into a medical device when the device is being set up. The heparin vial 538 in FIG. 5 is an example of an anticoagulant source. Anticoagulant can be inserted into a removable portion such as the disposable portion 804 or 904 depicted in FIGS. 8 and 9, respectively.

In some embodiments, systems and apparatus can have a design that helps prevent accidental injection of an anticoagulant into a patient. This can help avoid consequences such as excessive bleeding from loss of clotting capability and Heparin Induced Thrombocytopenia (HIT) in certain heparin sensitive patients. Such a risk-mitigating design can be especially advantageous for institutions such as hospitals that are searching for a reduction of "medication errors." In some institutions, reported incidences of "medication errors" are as high at 30%, which demonstrates a need for the system described herein.

In some embodiments, the described system can help to prevent and/or mitigate the following: 1) accidental anticoagulant injection into the patient from a vial intended for use in a medical device (e.g., the monitoring device 102 of FIG. 1); and 2) accidental re-use of a used anticoagulant vial that was fully or partially depleted. In some embodiments, the described system can facilitate easy transfer of anticoagulant from a container (e.g., a vial) to a medical device, and it can do it with a very low dead volume, which can help prevent anticoagulant waste. In some embodiments, the described system can also provide for a highly accurate anticoagulant delivery system (e.g., in the form of a syringe pump) for use inside a medical device (e.g., the monitoring device 102 of FIG. 1). Moreover, in some embodiments, the described system can provide for all system components to be configured for single-patient use, reducing and/or eliminating cross infection risks.

As illustrated in FIG. 6, some embodiments can deliver anticoagulant to a fluidics system in a different way than that illustrated in FIG. 5, which depicts a shuttle valve 541. FIG. 6 shows how, in some embodiments, anticoagulant can be delivered by an anticoagulant pump 588, which can insert anticoagulant into a passageway (T15). The passageway (T15) can be opened or shut by the anticoagulant pinch valve 589 (Vhep). This pinch valve 589 (Vhep) can be the first in a series of valves that, under the control of a control system (e.g., the fluid system controller 405 of FIG. 4), can help prevent unwanted movement of the anticoagulant. For example, in some embodiments, these valves can prevent heparin from being returned to a patient, but instead allow the heparin to flow through the passages of a monitoring device.

In FIG. 6, the reference letters "B", "M", and "D" indicate that in some embodiments, the components can be in, on, or associated with a door (D), a meter (M), or both (B). A "door" can refer to a movable portion 706, for example (see FIG. 7). A "meter" can refer to the monitoring device 102 of FIG. 1, for example. In some embodiments, such a monitoring device can be referred to as a "meter" because of its measuring function; in some embodiments, it measures glucose concentrations in blood.

In some embodiments, a system can comprise a special syringe that is configured to not fit into regular valves and connectors, and an apparatus that allows anticoagulant to flow into the syringe.

Figure 28:
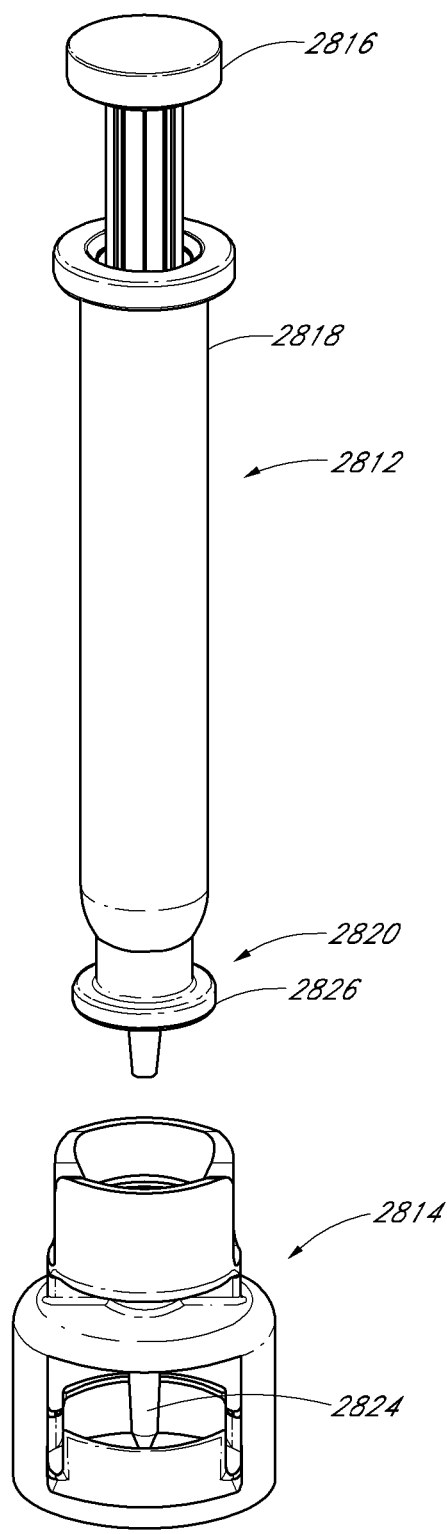
FIG. 28 illustrates a syringe embodiment and an adapter embodiment.

As illustrated in FIG. 28, some embodiments comprise a syringe 2812 and an adapter 2814. The syringe 2812 can have a plunger 2816, a body 2818, and a tip portion 2820. The tip portion 2820 can be configured to mate with the adapter 2814. The tip portion 2820 can have a collar 2826 that can be configured to maintain a connection between the syringe 2812 and the adapter 2814. The adapter 2814 can have a protrusion 2824 that can be configured to penetrate a container (e.g., it can pierce a seal on a heparin vial).

Figure 29:
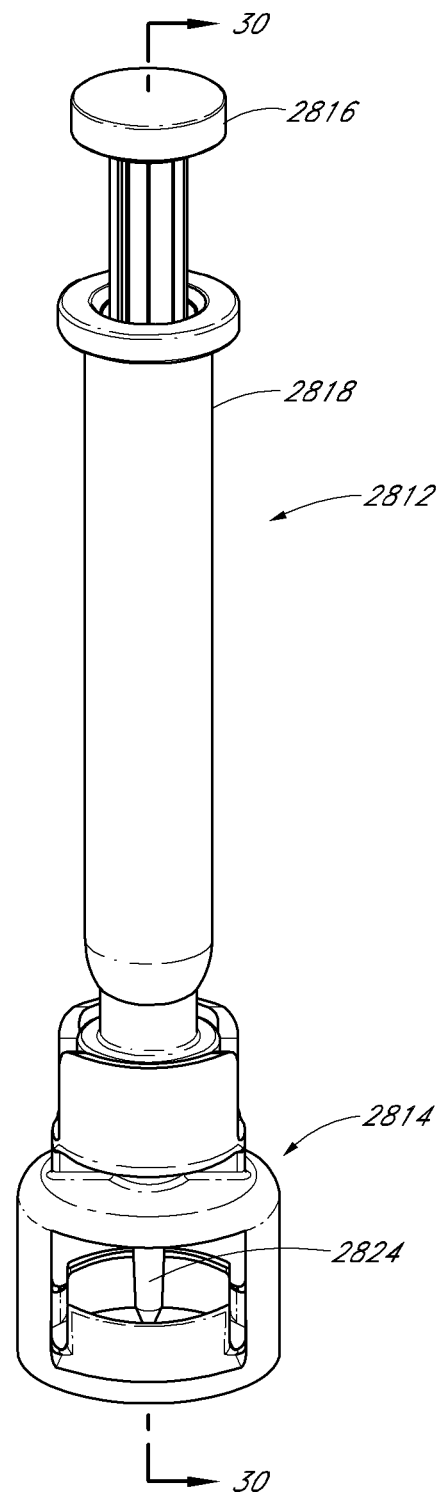
FIG. 29 shows the syringe and adapter of FIG. 28 connected to each other.

FIG. 29 illustrates a configuration where the syringe 2812 is connected to the adapter 2814. Indeed, the syringe 2812 can be supplied to a consumer pre-attached to the adapter 2814, in the illustrated configuration. Preferably, the syringe-adapter combination is supplied in a sterile state to a medical provider. Sterility can help reduce the risk of infection, and pre-connection can help reduce the possibility of misuse (e.g., for delivery of a substance directly to a patient, instead of into the system as designed).

Figure 30:
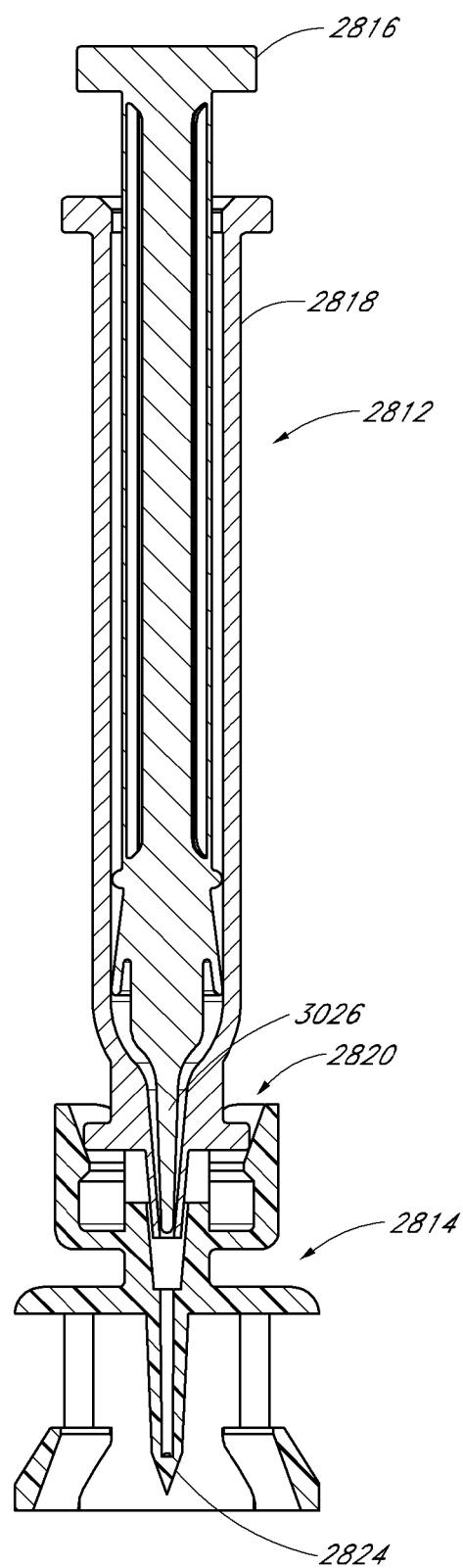
FIG. 30 shows a cross section through the syringe and adapter of FIG. 29 taken along the section line 30-30.

FIG. 30 shows a cross section through the syringe 2812 and the adapter 2814, along the section line 30-30 shown in FIG. 29. As illustrated, the plunger 2816 has an elongate nose portion 3026 that extends into the tip portion 2820 of the syringe 2812, thus helping to force fluid from the syringe 2812 and reducing potential dead space. Reduction of dead space can provide many advantages. For example, it can reduce the amount of fluid needed for the system by reducing the fluid that remains in the dead space during each cycle. Over time, the physical configuration of an elongate nose portion that reduces dead space can result in greatly reducing the amount of fluid used and/or wasted. If the fluid is an anticoagulant such as Heparin, for example, reducing dead space can allow a single container or vial of Heparin to last longer.

Figure 31:
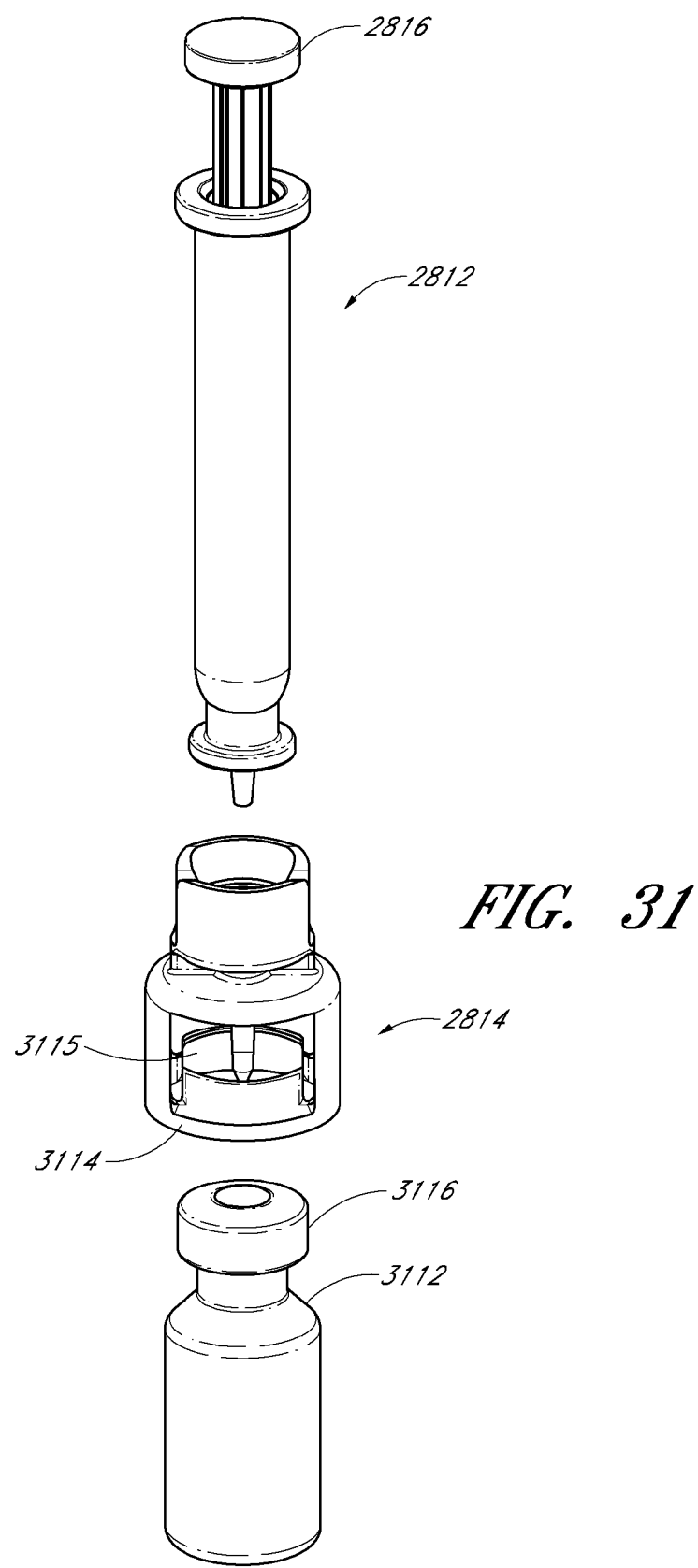
FIG. 31 shows an exploded view of the syringe and adapter of FIG. 28 with a vial.

FIG. 31 shows an exploded view of the syringe 2812, the adapter 2814, and a vial 3112. In some embodiments, a medical worker can receive a sterilized package comprising a syringe 2812 attached to an adapter 2814. The worker can then connect the adapter-syringe combination to the vial 3112. The vial can have a lip portion 3116 which can be configured to engage the latching tabs 3114, 3115 to help maintain a connection between the adapter 2814 and vial 3112.

Figure 32:
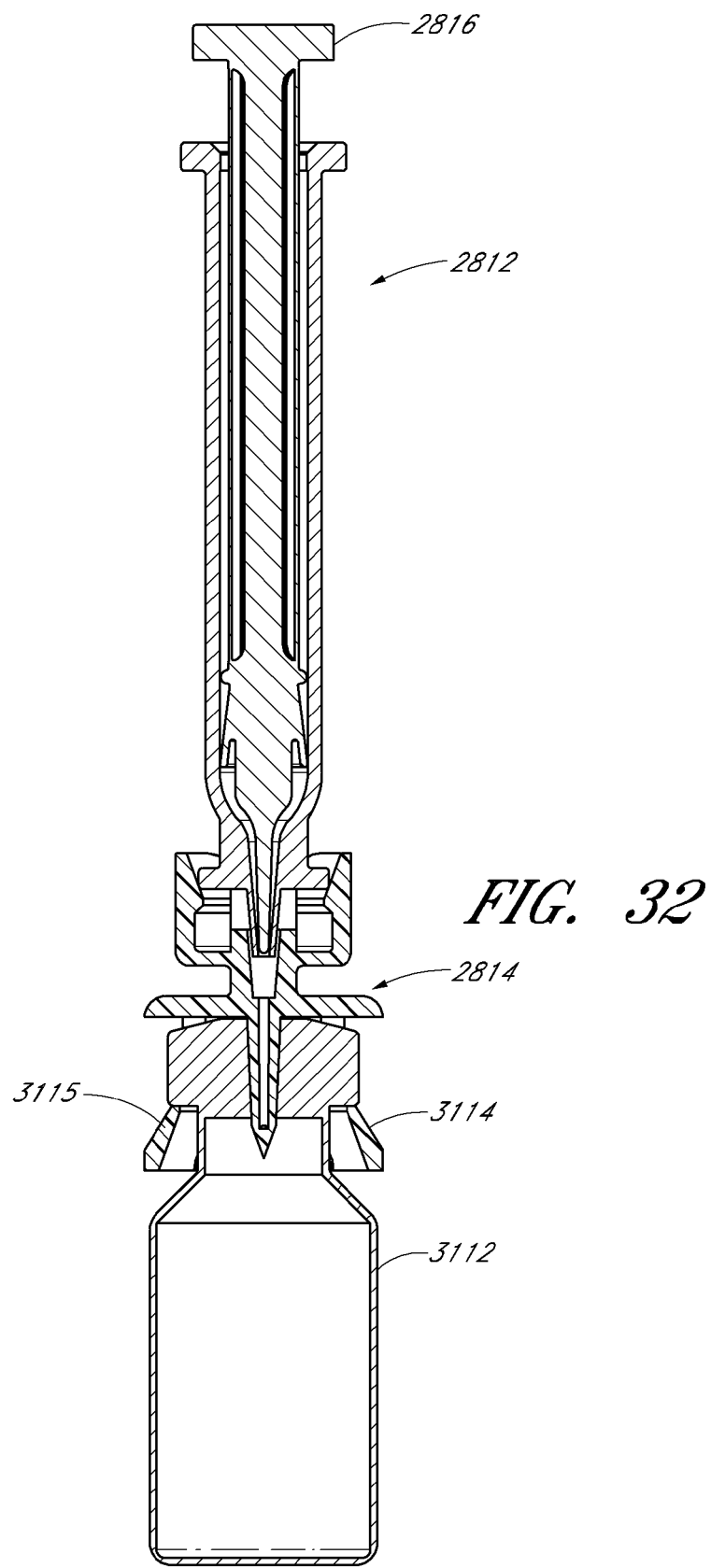
FIG. 32 shows a cross-section of the syringe, adapter, and vial of FIG. 31.

FIG. 32 shows a cross-section of the syringe 2812, the adapter 2814, and the vial 3112. Latching tabs 3114, 3115 that can be molded as part of the adapter 2814 can help make the connection relatively permanent so that it is difficult and/or impossible to remove the adapter 2814 from the vial 3112 once they are connected. Such a feature can help prevent re-use of the vial to deliver anticoagulant to a patient, for example.

Figure 33:
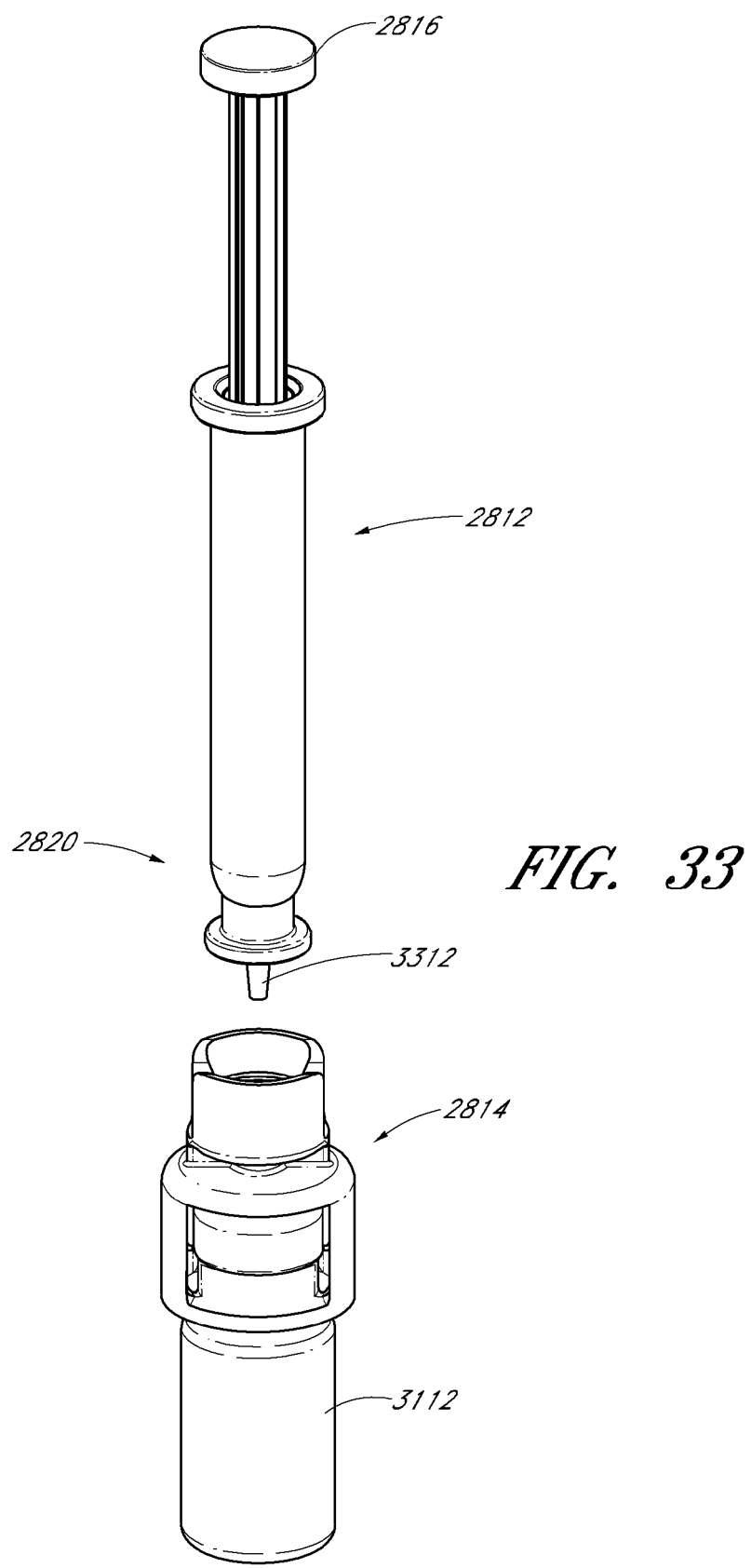
FIG. 33 illustrates the syringe separated from the adapter, with the plunger drawn back.

FIG. 33 illustrates how, after connection to the vial 3112, the plunger 2816 can be drawn back, transferring anticoagulant from the vial 3112 to the syringe 2812. The syringe 2812 can then be separated from the adapter 2814, which can remain with the vial 3112 as a deterrent to re-use of the vial 3112. A further safety feature can be the unusual configuration of the tip portion 2820, which can be different from standard connectors, thus deterring insertion into a standard luer fitting, tube, or port (or any other device for which the tip portion 2820 is not configured). Such a feature can also prevent a standard syringe from being attached to the vial-adapter combination, helping to deter re-use of a heparin vial, for example. In some advantageous embodiments, the tip 3312 of the syringe 2812 is not sharp and will not pierce the skin of a standard hospital infusion septum. This can help prevent accidental delivery of anticoagulant to a patient.

Figure 34:
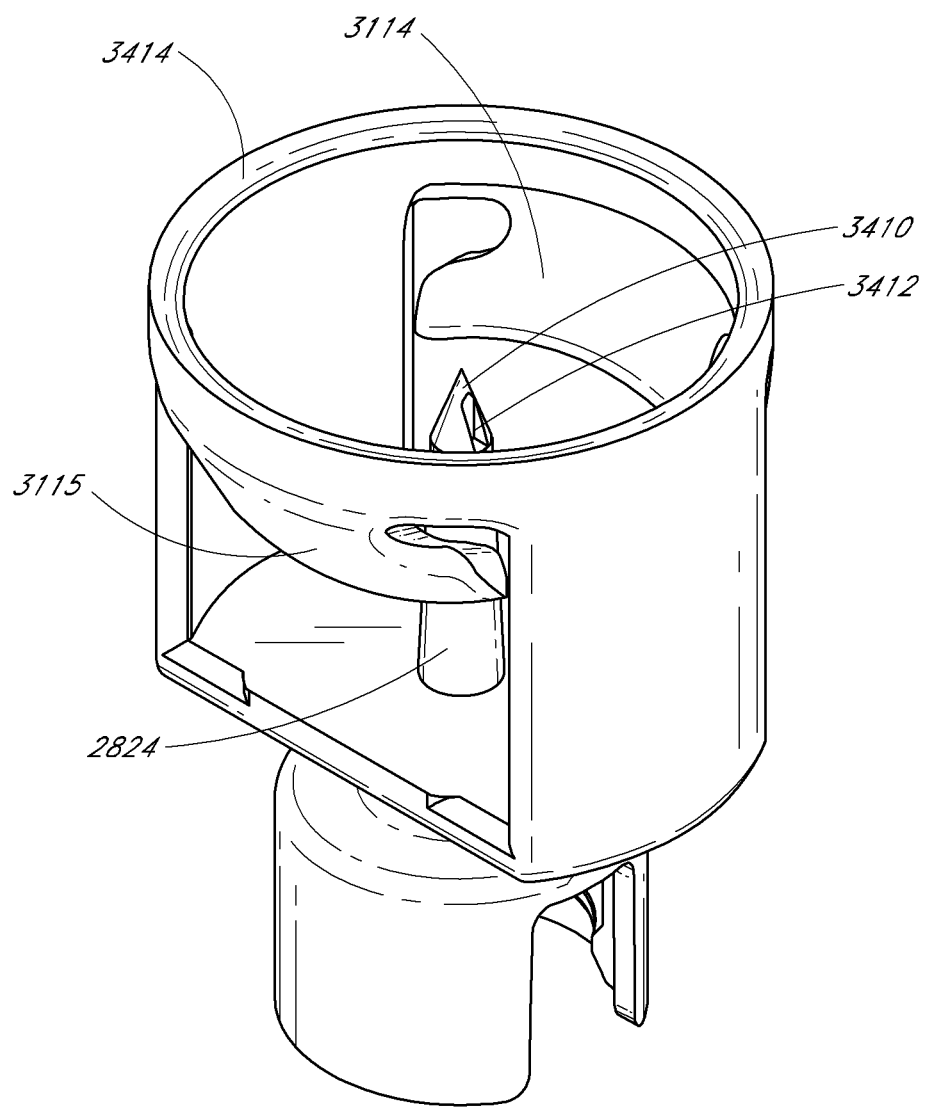
FIG. 34 illustrates an adapter embodiment.

FIG. 34 shows an embodiment of the adapter 2814. The adapter 2814 can have a canted surface 3414 at one end to guide the vial 3112 (not shown) into position on the adapter 2814. Latching tabs 3114, 3115 can be provided to engage the vial lip 3116. The adapter 2814 can have a protrusion 2824 that can be configured to penetrate a container (e.g., it can pierce a seal on a heparin vial). The protrusion can have a spike 3410 to facilitate piercing a container seal, and an intake port 3412 to allow passage of fluid between a container and the syringe 2812.

Figure 35:
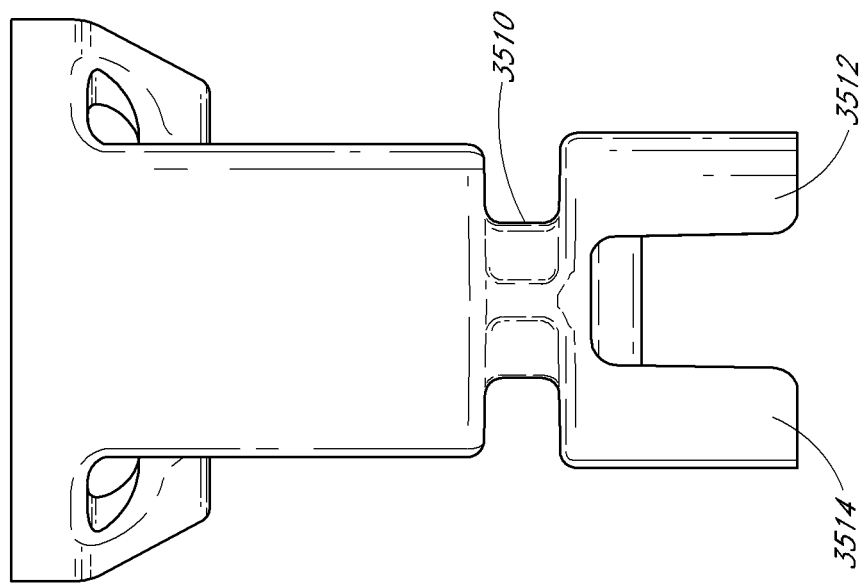
FIG. 35 is a front view of the adapter of FIG. 34, showing the latches that can grip the syringe.

FIG. 35 shows an embodiment of the adapter 2814, which can have an adapter neck 3510. The adapter 2814 can have a plurality of latches 3512, 3514 extending from the adapter neck 3510. The latches 3512, 3514 can be configured to be displaced temporarily as the syringe 2812 (not shown) is inserted into the adapter 2814. The displacement can be caused by the collar 2826 on the tip portion 2820 of the syringe 2812 coming into contact with a portion of the latches 3512, 3514. The displacement of the latches 3512, 3514 can be provided for with any suitable means, such as a spring, compliance of the material of which the adapter or a portion of the adapter is made, or other suitable means. In the embodiment illustrated in FIG. 35, the adapter 2814 can be made of a suitable material which allows for bending, such as plastic. The latches 3512, 3514 can be molded as part of the adapter 2814, thereby rigidly fixing them to the rest of the adapter 2814 such that they can be displaced in cantilever fashion when force is applied by the syringe 2812. The adapter can be configured to have an adapter neck 3510, which can allow for more displacement of the latches 3512, 3514 with less force and less strain on the latches 3512, 3514 or other portions of the adapter 2814. The number of latches 3512, 3514 can also be increased. In other embodiments, the adapter 2814 can have one continuous latch configured to surround the tip portion 2820 of the syringe 2812.

Figure 36:
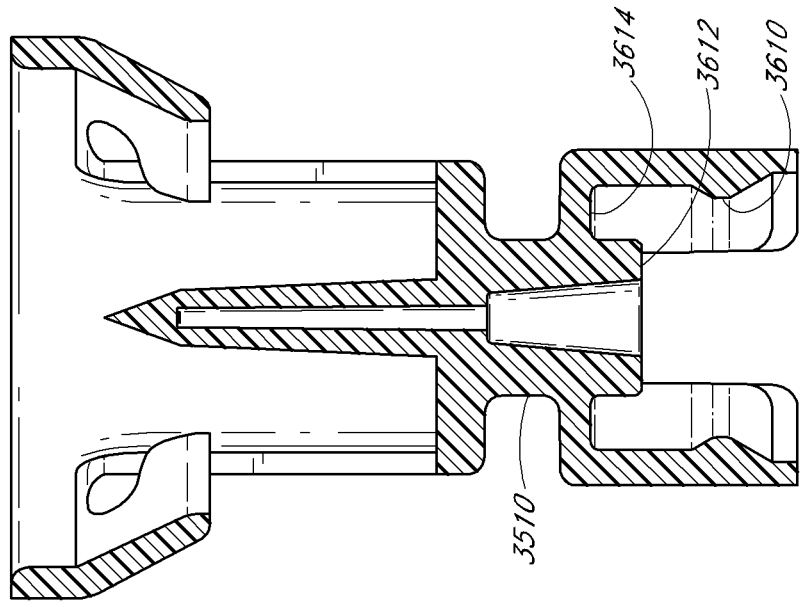
FIG. 36 shows a cross-section of the adapter of FIG. 35, showing the interior surfaces of the adapter that mate with the tip portion of the syringe.

FIG. 36 shows a cross-section of the adapter 2814 as shown in FIG. 35. The latches 3512, 3514 of the adapter 2814 can have a ridge 3610 configured to maintain a connection with the syringe 2812 (not shown), and can also allow for removal of the syringe 2812 if desired. The ridge 3610 can be present on one or more of the latches 3512, 3514 such that it surrounds the tip portion 2820 of the syringe 2812 when the syringe 2812 is connected to the adapter 2814. The adapter 2814 can be of various shapes, and is shown in FIG. 36 as circular. In this embodiment, the ridge 3610 can define a passage having a diameter less than the diameter of the collar 2826. Thus, when the tip portion 2820 of the syringe 2812 is inserted into the adapter 2814, the collar 2826 of the syringe 2812 will interfere with the ridge 3610. As the collar 2826 is pushed past the ridge 3610, the latches 3512, 3514 are displaced and/or portions of the syringe 2812 or ridge 3610 are deformed. Once the collar 2826 is forced past the ridge 3610, the latches 3512, 3514 can spring back into at-rest position and removal of the collar 2826 will be prevented by the ridge 3610 on the latches 3512, 3514. If desired, the syringe 2812 can be pulled out of the adapter 2814 opening or otherwise broken away from the adapter 2814. Various configurations of the ridge 3610 and collar 2826 can be used to vary the force needed to remove the syringe 2812 from the adapter 2814.

The adapter 2814 can also have a surface 3612 that can be configured to mate with the collar 2826 of the syringe 2812. The adapter 2814 can be configured such that the collar 2826 is engaged both by the ridge 3610 and the surface 3612 of the adapter 2814 once the syringe 2812 is inserted into the adapter 2814. The engagement of the surface 3612 and the collar 2826 can facilitate transfer of fluid between the container and the syringe 2812. The adapter 2814 can also have a recessed surface 3614, spaced apart from the surface 3612. The spacing of the recessed surface 3614 can create an annular cavity when the syringe 2812 is connected to the adapter 2814. The presence of this cavity can facilitate removal of the syringe 2812 from the adapter 2814 by decreasing the engagement surface area between the collar 2826 and the surface 3612.

Figure 37:
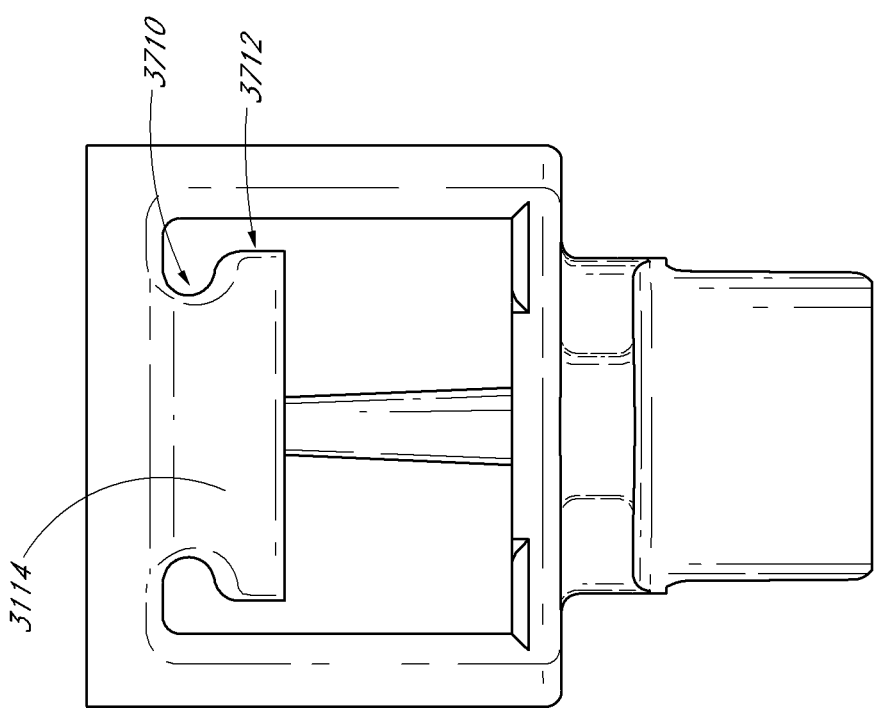
FIG. 37 is a side view of the adapter of FIG. 34, showing a latching tab.

FIG. 37 is a view of the adapter 2814 showing latching tab 3114. The latching tabs 3114, 3115 can have a neck portion 3710 and a head portion 3712. The cross-section of the neck portion 3710 can be less than the cross-section of the head portion 3712. The latching tabs 3114, 3115 can be configured to deflect as the vial 3112 (not shown) is forced through an opening of the adapter 2814. The smaller cross-section of the neck portion 3710 can allow for deflection of the latching tabs 3114, 3115 with less force and less strain to the materials. The head portion 3712 can be configured to have a larger cross-section in order to provide increased engagement surface with the vial lip 3116 once the vial 3112 is connected to the adapter 2814.

The latching tabs 3114, 3115, when not fully deflected, can define an opening whose diameter is smaller than the diameter of the vial lip 3116. Thus, as the vial 3112 is being pushed onto the adapter 2814, the deflection of the latching tabs 3114, 3115 allows the vial lip 3116 to pass by the latching tabs 3114, 3115, at which point the latching tabs 3114, 3115 will return to their undeflected position and can engage the vial lip 3116. Alternatively, the latching tabs 3114, 3115 can be configured to be in a slightly deflected position when the vial 3112 is connected to the adapter 2814. The latching tabs 3114, 3115 can be configured such that once the vial 3112 has been inserted into the adapter 2814, the vial lip 3116 exerts a compressing force on the latching tabs 3114, 3115 when the vial 3112 is attempted to be removed from the adapter 2814. Thus, the vial 3112 can be permanently held in place by the latching tabs 3114, 3115.

The configuration of the latching tabs 3114, 3115 can make it difficult to remove the vial 3112 from the adapter 2814. In some embodiments, a large amount of force is needed to remove the vial 3112 from the adapter 2814. A worker attempting to remove the vial 3112 from the adapter 2814 would recognize that the vial 3112 is not easily removed from the adapter 2814 and thus consider whether the vial 3112 is intended to be removed from the adapter 2814. In other embodiments, the tabs 3114, 3115 can be configured to retain a connection with the vial 3112 such that only a sufficient force to break the tabs 3114, 3115 from the adapter 2814 or to disform or break any part of the adapter 2814 or vial 3112 can separate the vial 3112 from the adapter 2814. In other embodiments, the amount of effort needed to separate the vial 3112 from the adapter 2814 is at least greater than the amount of effort needed to attach the vial 3112 to the adapter 2814, thus signaling to a worker that the vial 3112 should not be used with any devices other than the adapter 2814. All of these features can help prevent re-use of the vial to deliver anticoagulant to a patient, for example.

The latching tabs 3114, 3115 can be configured to allow an object to pry back the latching tabs 3114, 3115 if the vial 3112 needs to be removed from the adapter 2814. For example, a pointed tip of a tool could be inserted into the area where the head portion 3712 extends out beyond the neck portion 3710 of the latching tabs 3114, 3115 to facilitate removal of the vial 3112. In other embodiments, the wall of the adapter 2814 could be closed, thereby preventing access to the latching tabs 3114, 3115 and further preventing removal of the vial 3112 from the adapter 2814.

Figure 38:
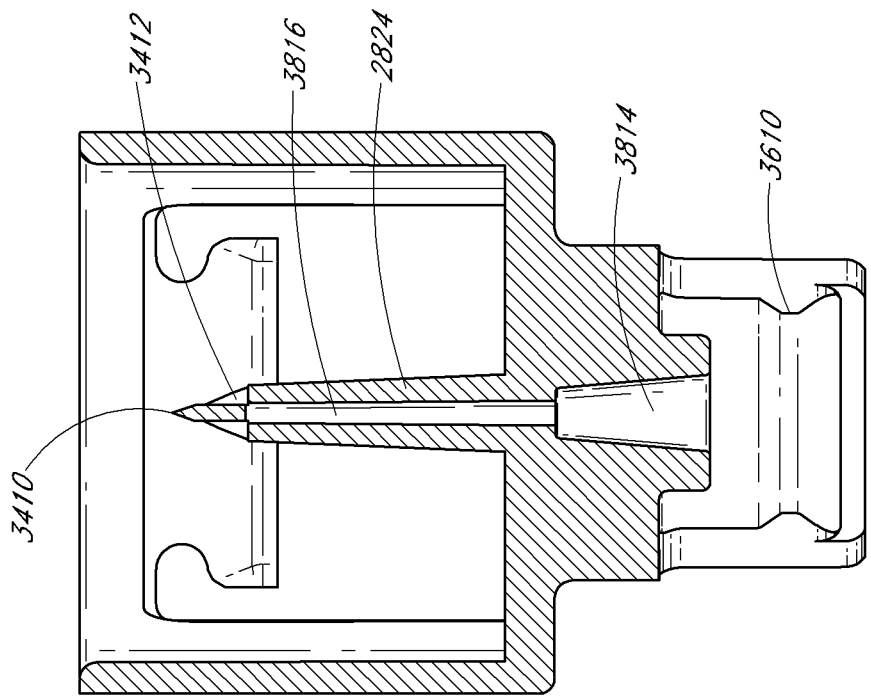
FIG. 38 shows a cross-section of the adapter of FIG. 37, showing the protrusion, spike, and intake port.

FIG. 38 shows a cross-section of the adapter 2814 of FIG. 37. The adapter 2814 can have a frusto-conical lumen 3814 that can be configured to mate with the tip 3312 (not shown) of the syringe 2812 (not shown). The adapter 2814 can also have an elongated lumen 3816 and an intake port 3412, which can both be in fluid connection with the frusto-conical lumen 3814 to facilitate fluid transfer between the vial 3112 and the syringe 2812. The protrusion 2824 can have a spike 3410 that can help to pierce a seal of a container. As the vial 3112 is inserted into the adapter 2814, the spike 3410 creates an opening in the vial 3112, and as the vial 3112 is further inserted into the adapter 2814, the protrusion 2824 of the adapter 2814, including the intake port 3412 or a plurality of intake ports, can occupy a space in the interior of the vial 3112. The protrusion 2824 can have a varying diameter, such that as the protrusion 2824 further penetrates the vial 3112 a close fit can be maintained between a seal of the vial 3112 and the protrusion 2824. The protrusion 2824 can be configured such that no portion of it extends beyond an end of the adapter 2814, to decrease the chance of other materials coming into contact with the protrusion 2824 and spike 3410. Both the frusto-conical lumen 3814 and the elongated lumen 3816 can be shaped such that conventional medical tools will be difficult or impossible to use to extract fluid from the vial 3112. In addition, the placing of the intake port 3412 to the side of the spike 3410 can prevent elongate objects such as syringe needles from being inserted through the elongated lumen and into the vial 3112, further preventing use of the contents of the vial for other purposes.

It is to be understood that the various features of the adapter 2814 can be modified and combined in different embodiments. For instance, the number of latching tabs 3114, 3115 or latches 3512, 3514 can be increased or decreased. The latching tabs 3114, 3115 and latches 3512, 3514 can accomplish their functions by being spring-loaded, providing an interference fit with the components of the syringe 2812 and vial 3112, or any other suitable mechanism. Cross-sections of the adapter 2814 can be circular, square, or any other suitable shape. The various interior contours of the adapter 2814 can be changed to modify interaction with the syringe 2812 and vial 3112 surfaces, as well as to modify the force needed to connect the syringe 2812 and vial 3112 to the adapter 2814 or disconnect the syringe 2812 and vial 3112 from the adapter 2814.

Figure 39:
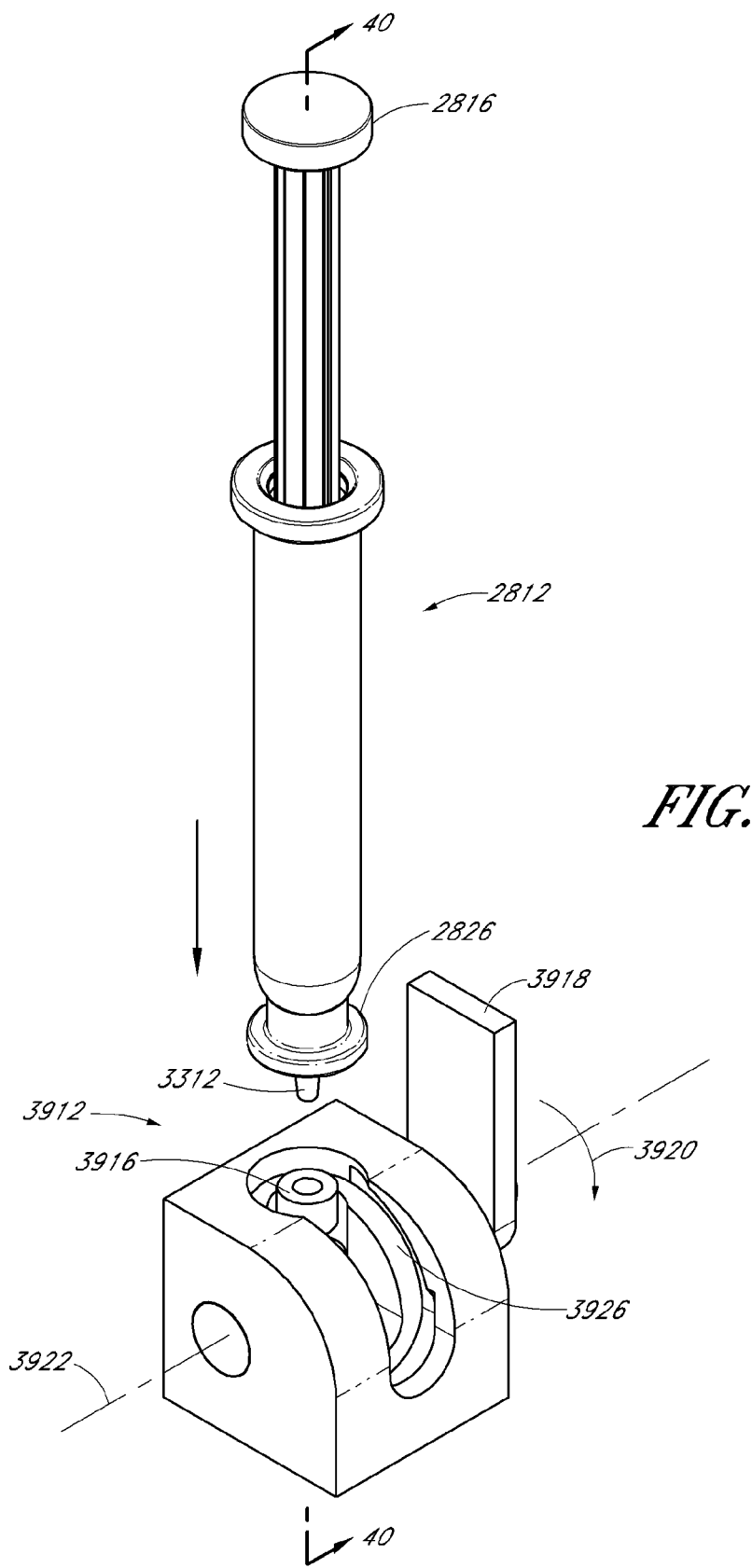
FIG. 39 illustrates the syringe and a dock configured to mate with the syringe.

FIG. 39 shows the syringe 2812 adjacent to a dock 3912. The syringe tip 3312 can be configured to mate with a receiving port 3916 in the dock 3912. The dock can be a manifold block that is part of a disposable cartridge which can be the disposable portion 804 of FIG. 8, for example. In some embodiments, the dock 3912 accomplishes several tasks. It can: 1) provide a fluid sealed mating to a heparin syringe; 2) lock the syringe in place preventing removal; and/or 3) provide a mechanical interlock that prevents insertion of an insertable portion (e.g., the disposable portion 804) unless the heparin syringe is properly and completely installed.

With further reference to FIG. 39, a rotating tab 3918 can be coupled to the receiving port 3916, and they can both rotate together in the direction of the arrow 3920, pivoting about the axis 3922. The collar 2826 can be configured to slide along the slot 3926 when the syringe 2812 is mated with the dock 3912 and the rotating tab 3918 is rotated. The slot 3926 can thus help lock the syringe 2812 and the dock 3912 together.

Figure 40:
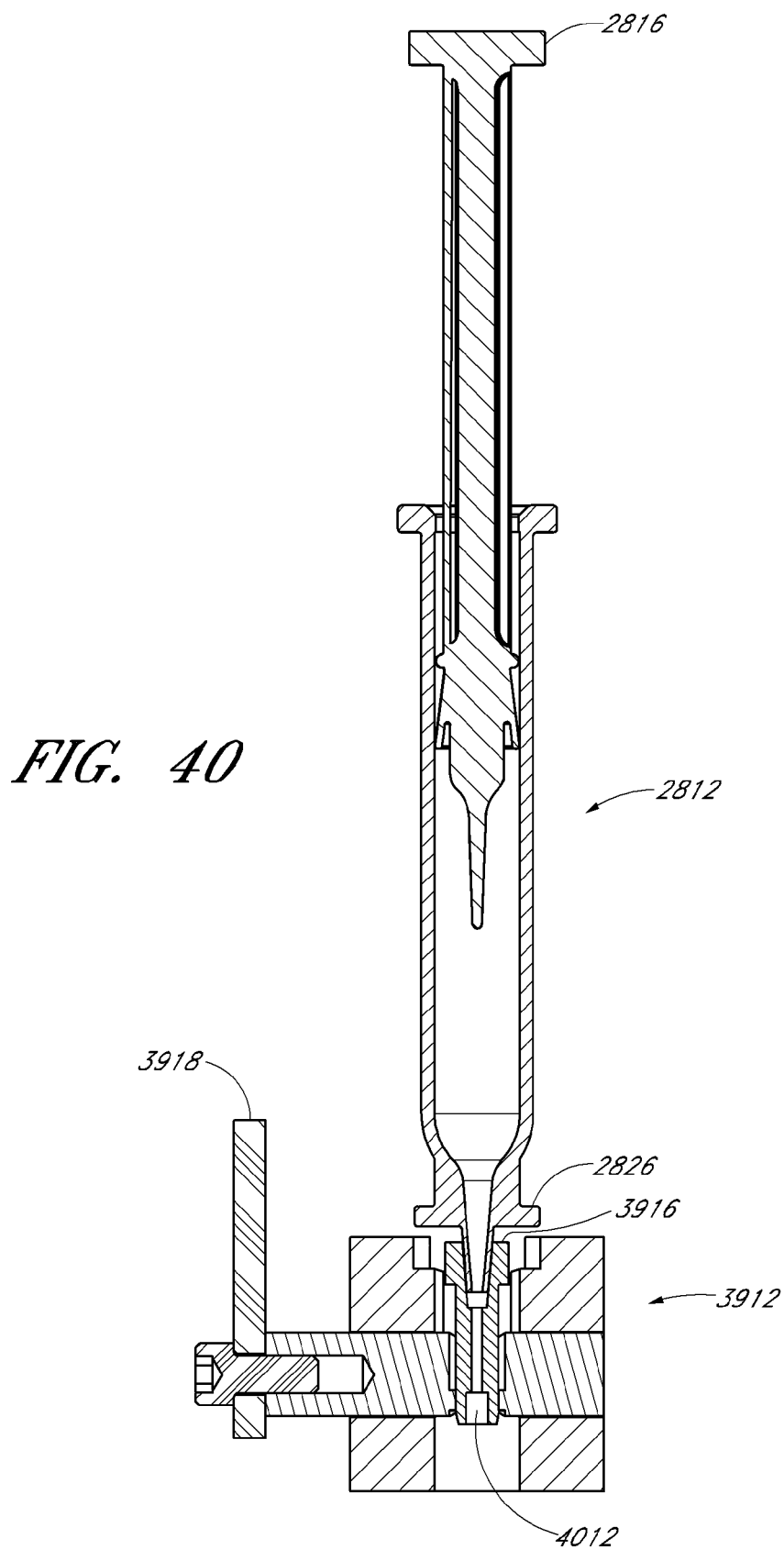
FIG. 40 shows a cross-section of the syringe 2812 and the dock 3912 as the syringe is being mated to the receiving port 3916.

FIG. 40 shows a cross section of the syringe 2812 and the dock 3912 as the syringe is being mated to the receiving port 3916. A flow passage 4012 can lead to the interior fluid passages of a monitoring system 102. This cross sectional view also shows how a fluid seal can be maintained through tapered fittings.

Figure 41:
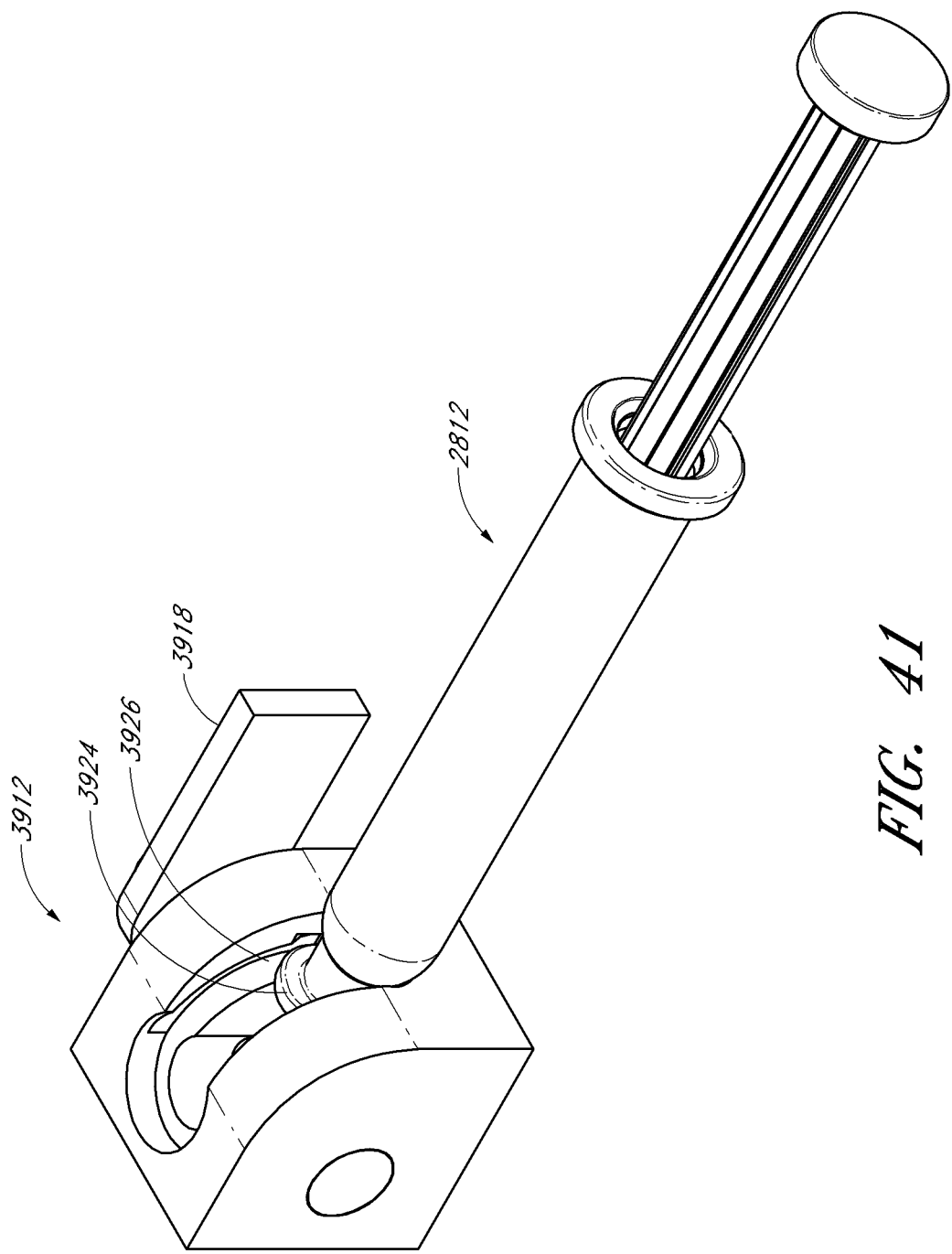
FIG. 41 shows the syringe mated to the dock when the syringe has been rotated into a connected position.

FIG. 41 shows the syringe 2812 and the dock 3912 in the locked configuration discussed above, after the tab 3918 has been rotated and the collar 2826 is held within the slot 3926. This position of the syringe 2812 relative to the dock 3912 can be referred to as the "in use" position. One advantage of the collar 2826 is that it can prevent improper installation. For example, in some embodiments, the syringe cannot be rotated into position if it is not properly inserted.

In embodiments where the dock 3912 is incorporated into a disposable portion 804, the syringe 2812 can also be incorporated into the disposable portion 804. Thus, the syringe-dock combination can serve as a pump that can be actuated by actuators in a system such as those described above. This configuration can obviate a need for transferring fluid (e.g., anticoagulant) from the syringe 2812 to another pump. The tab 3918 can provide a mechanical interlock that prevents complete insertion of a disposable portion 804 unless the tab 3918 is in the "in use" position.

Figure 42:
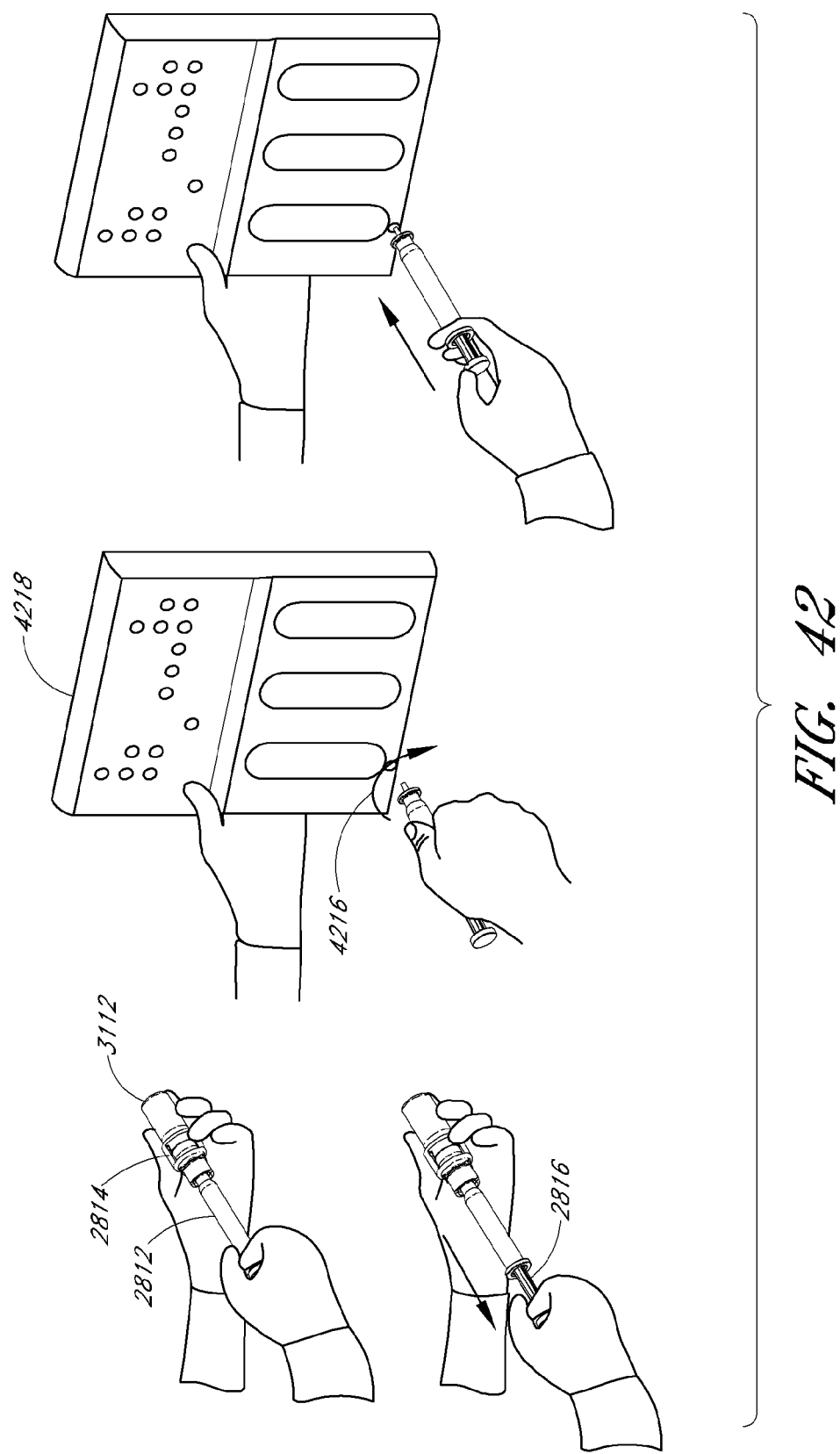
FIG. 42 shows how the syringe can draw fluid from a container through an adapter, separate from the adapter and container, and inject the fluid into a cartridge.

Some embodiments do not incorporate the syringe 2812 into the disposable portion 804. For example, FIG. 42 illustrates one way that the described system, sans dock 3912, can be used. The syringe 2812 has been connected to the adapter 2814, and the adapter-syringe combination has been connected to the vial 3112. The plunger 2816 is drawn back, drawing fluid into the syringe 2812. The syringe 2812 is then broken away or otherwise removed from the adapter 2814, and the syringe is brought to a port 4216 in a cartridge 4218. The syringe 2812 can be configured to be secured to the port 4216 (e.g., through a turning motion, for example). With the syringe 2812 in place, the plunger can be depressed, forcing the fluid into the cartridge 4218.

Figure 43:
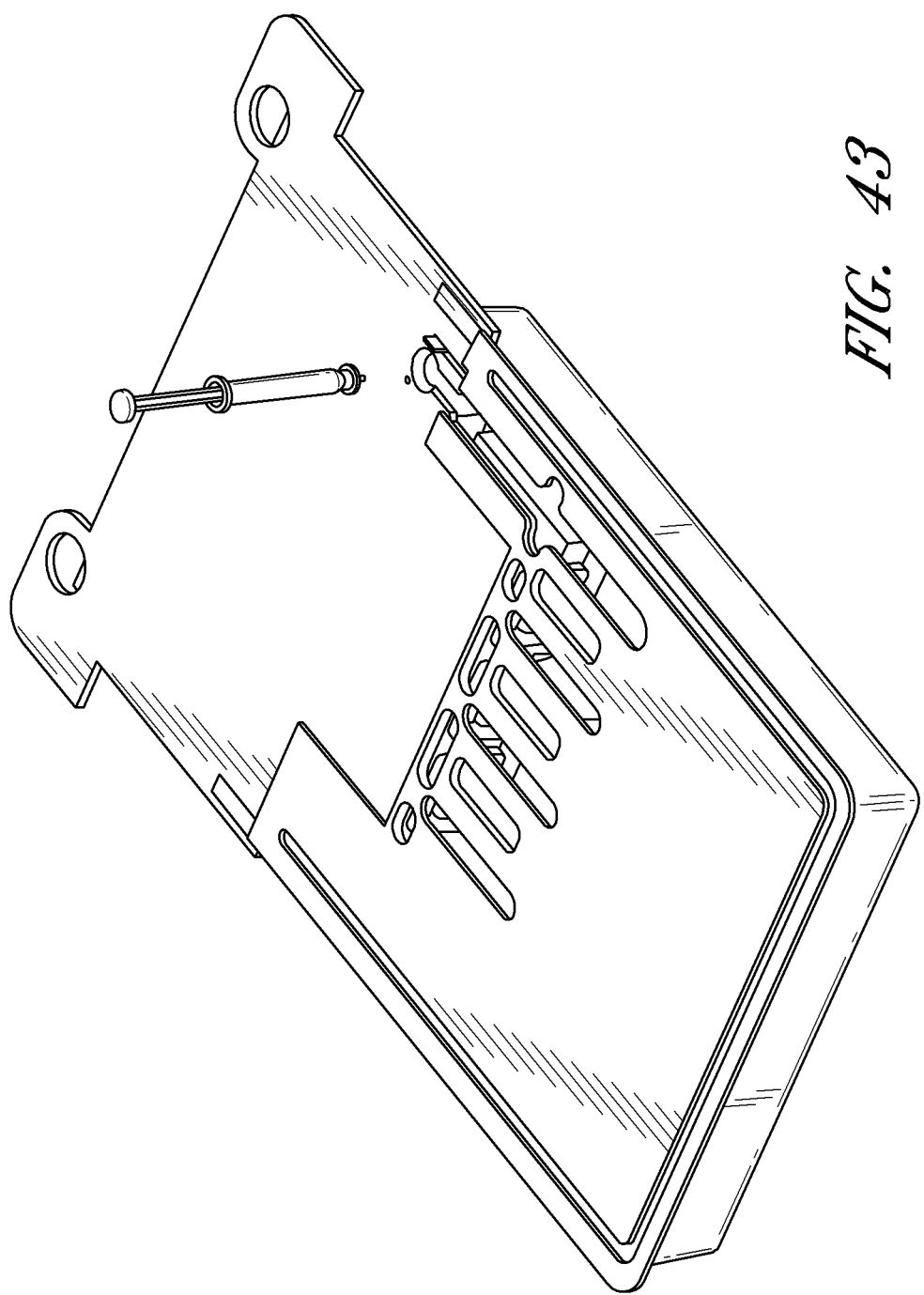
FIG. 43 shows a syringe and an embodiment of a cartridge with a dock and a syringe receptacle.

FIG. 43 shows a syringe and an embodiment of a cartridge with a dock and a syringe receptacle. A tab (which can be, for example, like the tab 3918 of FIG. 39) of the dock can be seen protruding from the cartridge.

Figure 44:
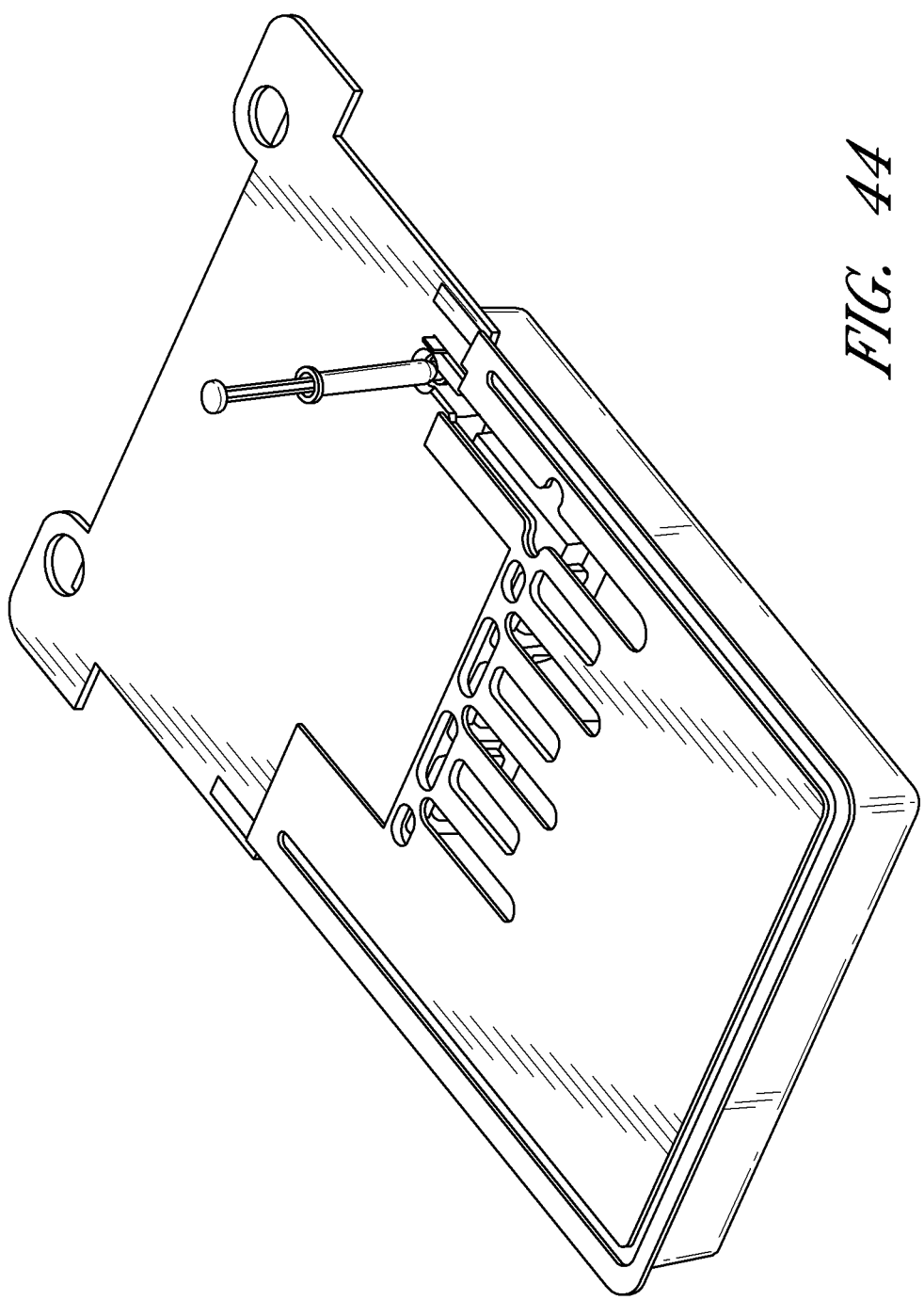
FIG. 44 shows the syringe mating with the dock in the cartridge of FIG. 43.

FIG. 44 shows the syringe mating with the dock in the cartridge of FIG. 43.

Figure 45:
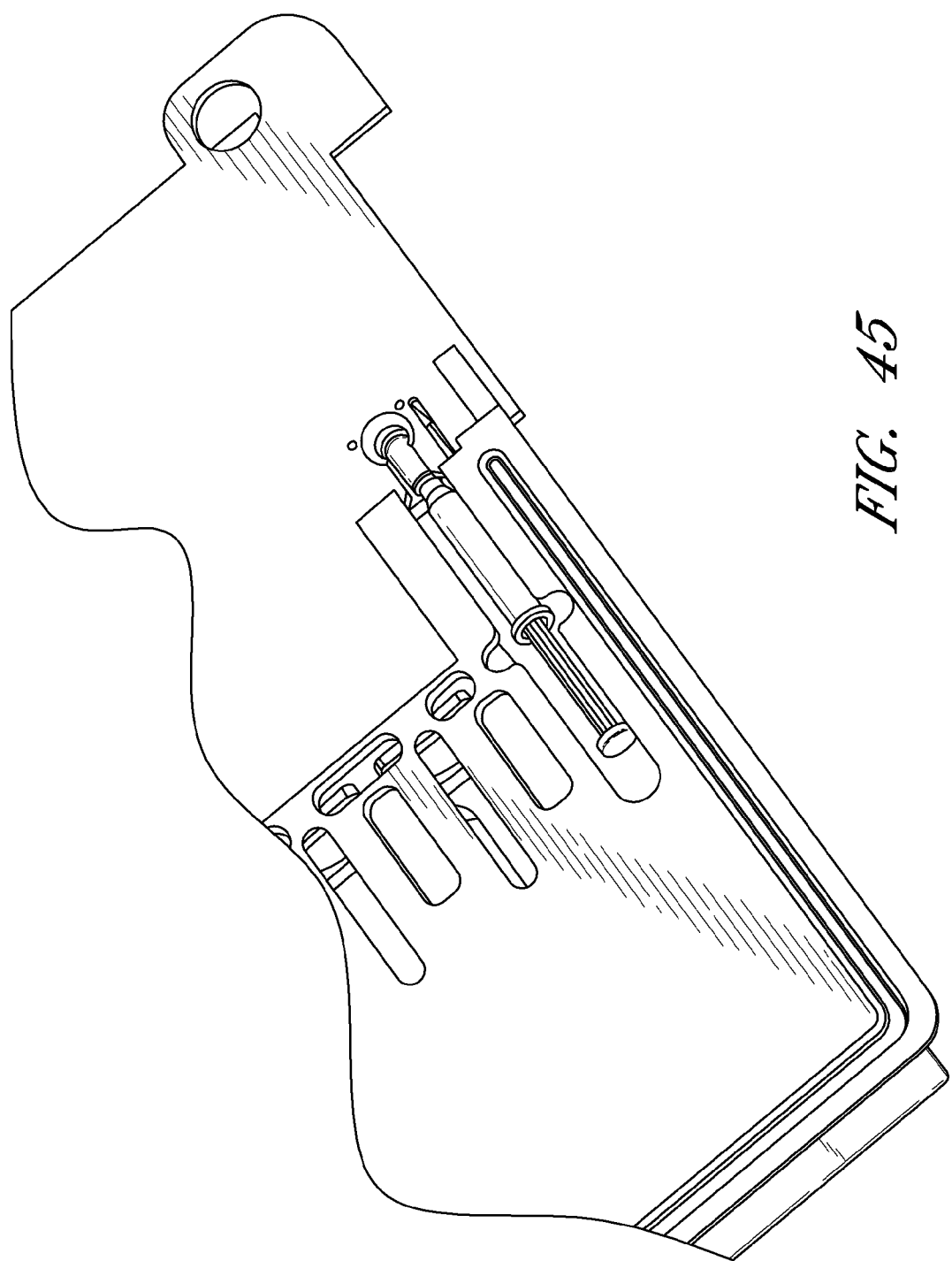
FIG. 45 shows the syringe connected to the dock and rotated down into the syringe receptacle in the cartridge of FIG. 43.

FIG. 45 shows the syringe connected to the dock and rotated down into the syringe receptacle in the cartridge of FIG. 43. The tab has been rotated down and can no longer be seen protruding from the dock. This configuration can incorporate the syringe into the cartridge, where it can serve as a portion of the disposable and can be actuated by a non-disposable actuator, for example.

In some embodiments, heparin is administered by a caregiver according to the following method. The example method is directed toward one possible implementation for anticoagulant handling in a monitoring device and is intended to illustrate certain aspects of the method and is not intended to limit the scope of possible anticoagulant handling methods. A heparin system is provided, which can contain both a syringe and an integrated, locking vial adaptor. The heparin system can be either packaged with a disposable cartridge that is removable from the monitoring device or provided separately, depending upon the medication handling preferences of the environment in which the device is used, e.g., hospital. A 10,000 unit vial of heparin (1 ml vial) is obtained from the hospital pharmacy. With the plunger of the syringe fully depressed, the heparin system (syringe and locking adapter) is pressed onto the heparin vial until the system is securely attached to the rim of the vial. The adapter can no longer be removed from the vial. The caregiver then draws up the entire contents of the heparin vial into the syringe. The syringe may have a "full" indicator on its barrel, which the user or caregiver can use to ensure that all the heparin was transferred from the vial to the syringe. The caregiver then firmly detaches the syringe from the adapter. The empty vial, still connected to the adapter, is then discarded into the appropriate waste container. The caregiver can then attach the heparin syringe into an opening on the rear of the disposable cartridge. The opening may be labeled "Heparin Port" to assist the caregiver in finding it. The heparin syringe is inserted into the opening and rotated towards the disposable cartridge, so that it is parallel with the cartridge. An "open" button can then be pressed on the monitoring device, to open a door. The caregiver can then insert the cartridge into its designated location. The door of the monitoring device is then closed.

Automated Setup and Instruction System

The monitoring device, e.g., the monitoring device 102, can provide instructions for use of the device. Medical devices are often provided with user's manuals or instructions for use (IFU) designed to aid an operator or user of the device. Hard copy manuals or instructions can be lost, stored in a location separate from the device, or cumbersome to follow during actual use. A worker may have trouble remembering the steps to take to set up or use the medical device, or it may be desirable that a worker is given real-time instructions regardless of whether the worker remembers the instructions from previous study or use. Real-time instructions may aid in reduction of errors or misuse of the device, not only by reminding workers how to use the device but by using sensors or user inputs to attempt to prevent proceeding to the next step of use until the previous steps have been successfully completed. Real-time instructions can also facilitate updates or changes to the instructions, possibly as a supplement to periodic training of workers using the device. The monitoring device 102 can comprise an automated setup instruction system. In some embodiments the automated setup instruction system comprises an in-service medical device wizard.

Figure 46:
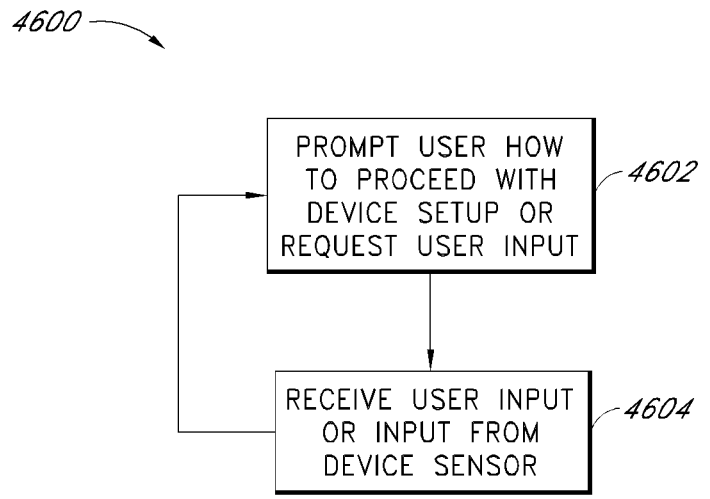
FIG. 46 illustrates schematically an example embodiment of a method of providing automated setup instructions for a medical device.

FIG. 46 illustrates schematically a method 4600 of providing automated setup instructions for a medical device using an embodiment of the system. In block 4602, the automated setup instruction system can prompt a user of the device how to proceed with setup or use of the device. The prompt can be a visual prompt, audio prompt, or other suitable user prompt. In block 4604, the automated setup instruction system can receive input from a user of the device or from one or more sensors. The input from the user can be an answer to a query from the automated setup instruction system or a command to continue to provide the next set of instructions. The device can also have a sensor configured to automatically detect the configuration of components of the medical device, data regarding the environment in which the device is used, or other information. Input from the user or from the sensor can indicate that the prior step has been completed, or perhaps is not necessary. Once the input is received, the method 4600 returns to block 4602 and prompts the user on the next step to be performed. In some embodiments, no input is needed to proceed to the next step, e.g., the automated setup instruction system proceeds to the next step after an amount of time has passed or according to other suitable measures.

Figure 47:
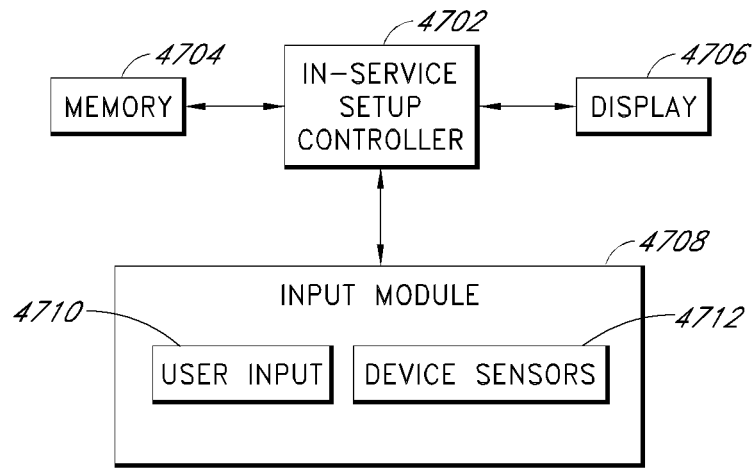
FIG. 47 is a block diagram of an embodiment of a system for providing automated setup instructions.

FIG. 47 schematically illustrates one embodiment of the automated setup instruction system 4700. The setup instruction system 4700 can include a computer memory module 4704 and a display 4706. The memory module 4704 can be configured to store setup information and protocols that are specific to the medical device. The display 4706 can be configured to be visible to a medical device user when the user is preparing the medical device for use in a medical setting. The setup instruction system 4700 can also include an automatic in-service medical device setup controller 4702. The controller 4702 can be configured to access the memory module 4704 according to the stored protocols and determine what should be displayed to the user on the display. The controller 4702 can further be configured to provide sequential instructions to the medical device user by displaying text and/or graphics on the display. The setup instruction system 4700 can also include an input module 4708. The input module 4708 can include an interface for accepting user input 4710 or input from one or more device sensors 4712. User input 4710 can relate to user-participation aspects of the device setup protocols. The user input

4710 can be an answer to a query displayed to the user on the display 4706 regarding specific preferences of the user concerning use of the device, the specific environment in which the device is to be used, or other relevant information. The user input 4710 can also include a command to continue to provide the next set of instructions on the display. The medical device can also have one or more device sensors 4712 configured to automatically detect device status information. Device status information can include the configuration of components of the medical device, data regarding the environment in which the device is used, or other information. Input can be communicated by the input module 4708 to the controller 4702 to enable the controller 4702 to determine which setup information to display on the display 4706. The input from the input module 4708 can indicate that the prior step has been completed or is not necessary, that there is a problem which needs correction, that a change in setup is required, or other information needed by the controller 4702 to properly guide the user in setting up the device.

In some embodiments, the automated setup instruction system can use the display 104, display system 414, or user interface 2400 of the monitoring device 102 to prompt a user on how to use the device once it is powered on. After some initial prompts, the user may be prompted on how to setup the device to monitor a patient. Setup can begin with loading heparin into a removable portion of the device, e.g., the removable portion 710 in FIG. 7 or disposable portion 804 in FIG. 8.

Figure 48:
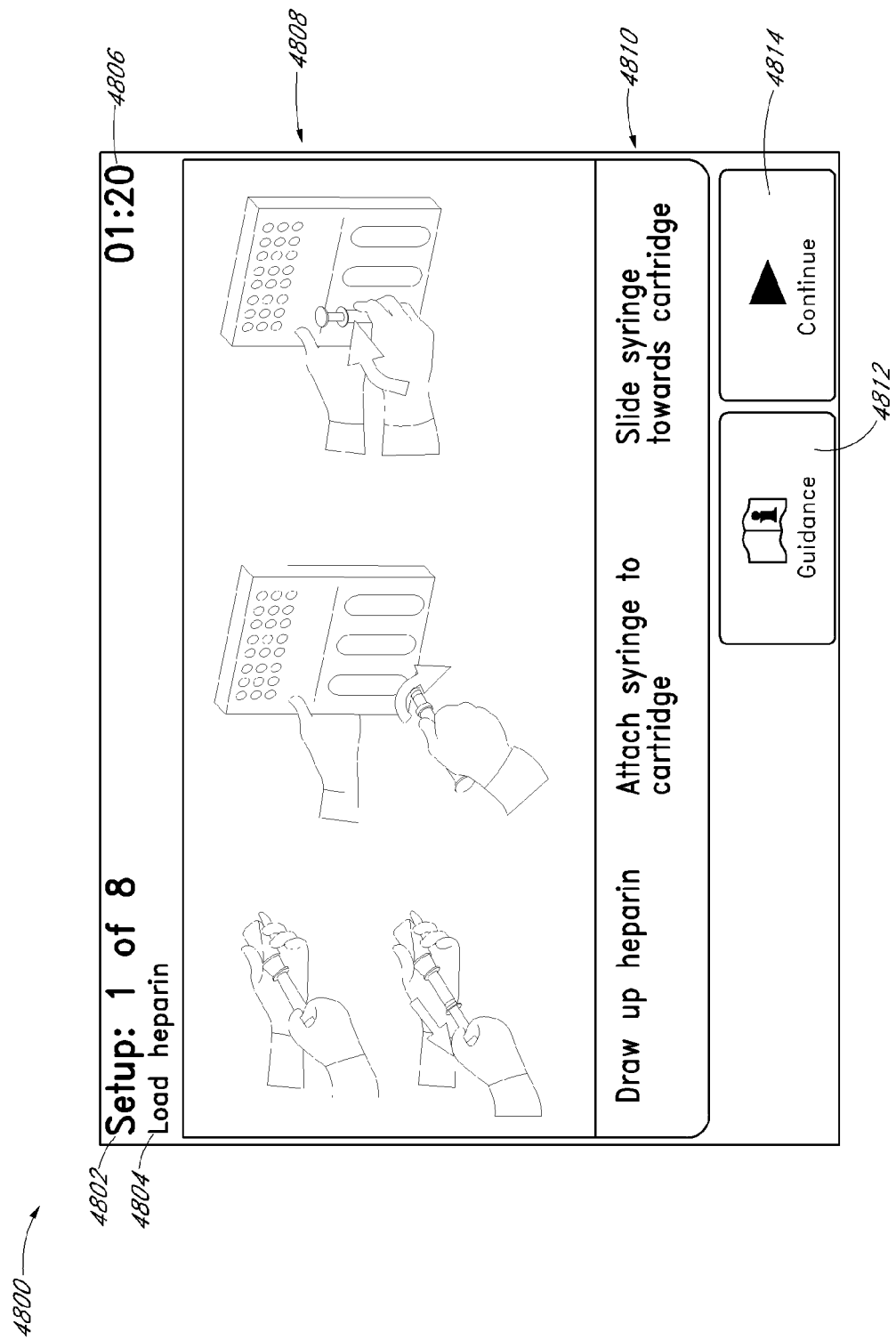
FIG. 48 schematically illustrates the visual appearance of the display of an embodiment of an automated setup instruction system.

FIG. 48 schematically illustrates the visual appearance of the display of an embodiment of the automated setup instruction system used with a medical device, e.g., the monitoring device 102. In this example embodiment, the automated setup instruction system prompts a user to load heparin into a removable portion of the device. In FIG. 48, the automated setup instruction system displays prompts or queries using a display or user interface 4800, which can be the user interface 2400 described above. The user interface 4800 may show progress information 4802, which can include labels for various stages of use (e.g., "Setup") as well as the current step and total number of steps in the stage (e.g., "1 of 8"). The user interface 4800 can also display a step description 4804, which can include a general description of the step being performed. For example, in FIG. 48 the step description 4804 being displayed is "Load heparin." The user interface 4800 also can include the current date and/or time 4806. A graphical display portion 4808 can display graphic prompts depicting performance of various sub-steps. A textual display portion 4810 can display text prompts, which can describe the sub-steps to a user of the device. Sub-steps may include more detail about specific steps to be taken in accomplishing the goals of the current step. For example, in FIG. 48, the user is prompted to "Draw up heparin," "Attach syringe to cartridge," and "Slide syringe towards cartridge" in order to perform the step of loading heparin. The user interface 4800 can also include a help button 4812, which may be an actuatable button on a touch screen labeled as "Guidance" in FIG. 48. Once the help button 4812 is actuated, additional information about the current step being performed can be displayed, which may include troubleshooting information. A continue button 4814 can also be shown on user interface 4800. The continue button 4814 can be actuated by the user when the steps described have been performed. In some embodiments, one or more sensors or switches in a monitoring device 102 can sense when a particular step has been performed and can automatically continue without input from the user. The user interface can then display the next step to be performed by the user, or indicate to the user that one or more actions should be performed before proceeding to the next step. For example, a sensor can be used to sense whether or not a door on the monitoring device 102 has been properly shut, or whether fluid is able to flow through one or more tubes of the device. The automated setup instruction system can prompt the user to close or open a door, or to examine a particular location of the device to determine if any of the tubing is pinched.

The automated setup instruction system can be used to prompt a user of a medical device to perform any number of steps in preparing or using the device. For example, the setup of the monitoring device 102 in FIG. 1 may include steps in addition to loading heparin into a removable portion. These steps can include, for example, loading the removable portion into the device, priming the removable portion with saline, adding a patient to be monitored, selecting a monitoring setup, reviewing analyte settings, selecting glucose alarm behavior, and attaching the device to a patient. As discussed, various aspects of the automated setup instruction system may require input from the user to continue to the next step. These inputs can include passwords or codes only known by someone with authority to perform various steps in the monitoring process. In some embodiments, initial use of the device will require a login, which may include a security password, to prevent unauthorized use of the device. The device can also track login information to determine which users performed which steps at various times. A user can log out to prevent further use of the device until another user logs in, or the device can have a timer that automatically locks the device.

Figure 49:
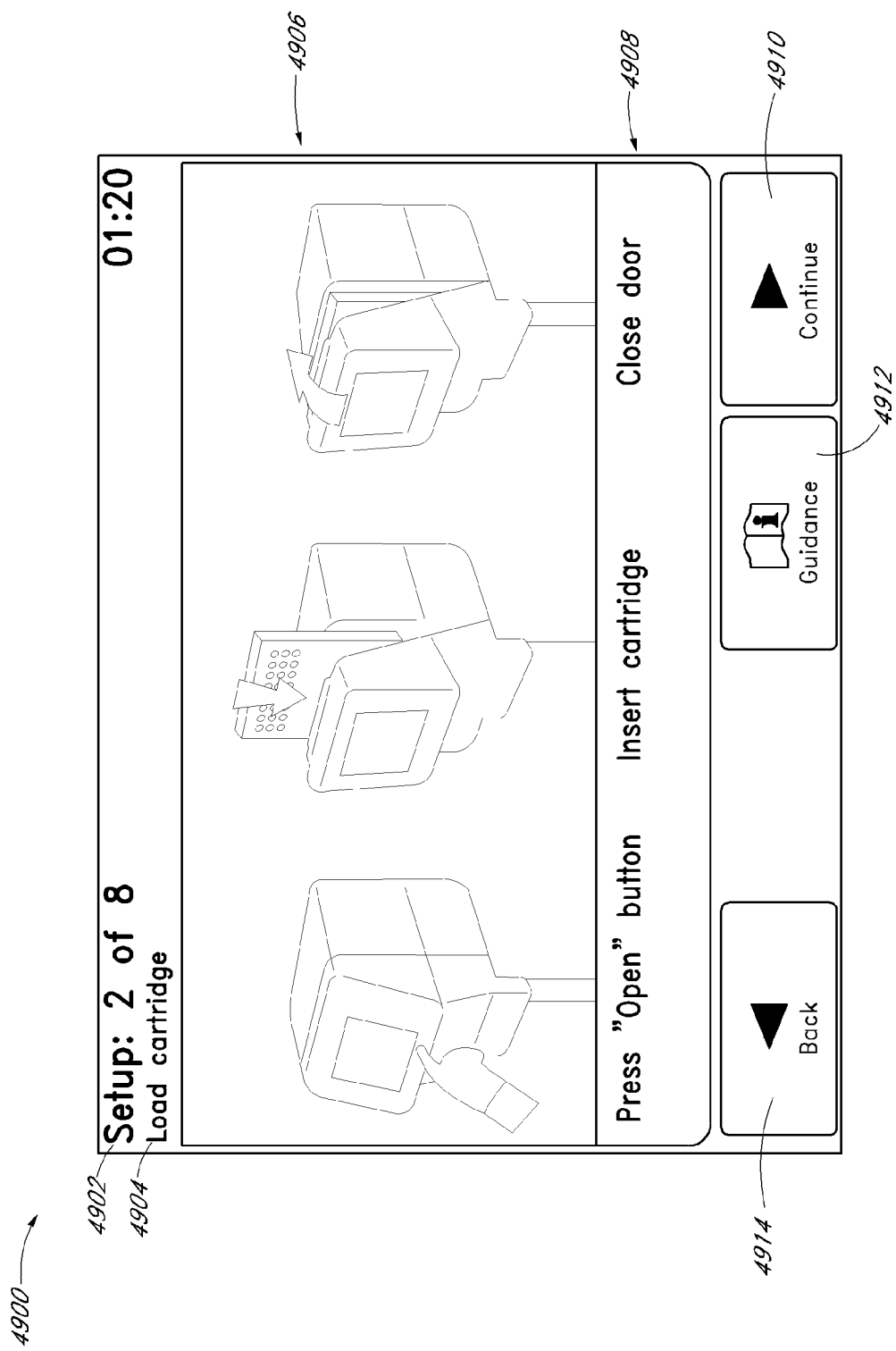
FIG. 49 schematically illustrates the visual appearance of the display of an embodiment of an automated setup instruction system.

FIG. 49 schematically illustrates the visual appearance of the display 4900 of an embodiment of the automated setup instruction system used with a medical device, e.g., the monitoring device 102. In this example embodiment, the automated setup instruction system prompts a user to load a removable portion into the device. The display 4900 indicates progress information 4902, or "Setup: 2 of 8" as shown in FIG. 49. A step description 4904 is displayed as "Load cartridge" in FIG. 49. A graphical display portion 4906 of the display 4900 visually depicts various sub-steps to be performed. A user of the device can rely on the depictions in the graphical display portion 4906 to accomplish the current step, and can also refer to text prompts shown in a textual display portion 4908 of the display 4900. In FIG. 49, the text prompts include "Press 'Open' button," "Insert Cartridge," and "Close door." The user can actuate touch-screen buttons at the bottom of the display 4900, which can include a "back" button 4914 which can cause the display to return to previous steps performed, a help button 4912 which can display additional information about the current steps being performed or provide access to a searchable user guide stored on the device, and a "continue" button 4910 which can be actuated by a user when the steps have been completed to indicate to the automatic setup instruction system that the next step should be displayed. As discussed, one or more sensors can be used to detect whether or not the cartridge has been properly inserted or whether or not the "Close door" step has been properly completed. The automated setup instruction system can be configured to continue automatically when the sensors indicate the steps have been performed. In some embodiments, the automated setup instruction system can alert the user that certain steps have not been properly performed if the user actuates the "continue" button 4910 and the sensors indicate the steps have not been properly completed.

Figure 50:
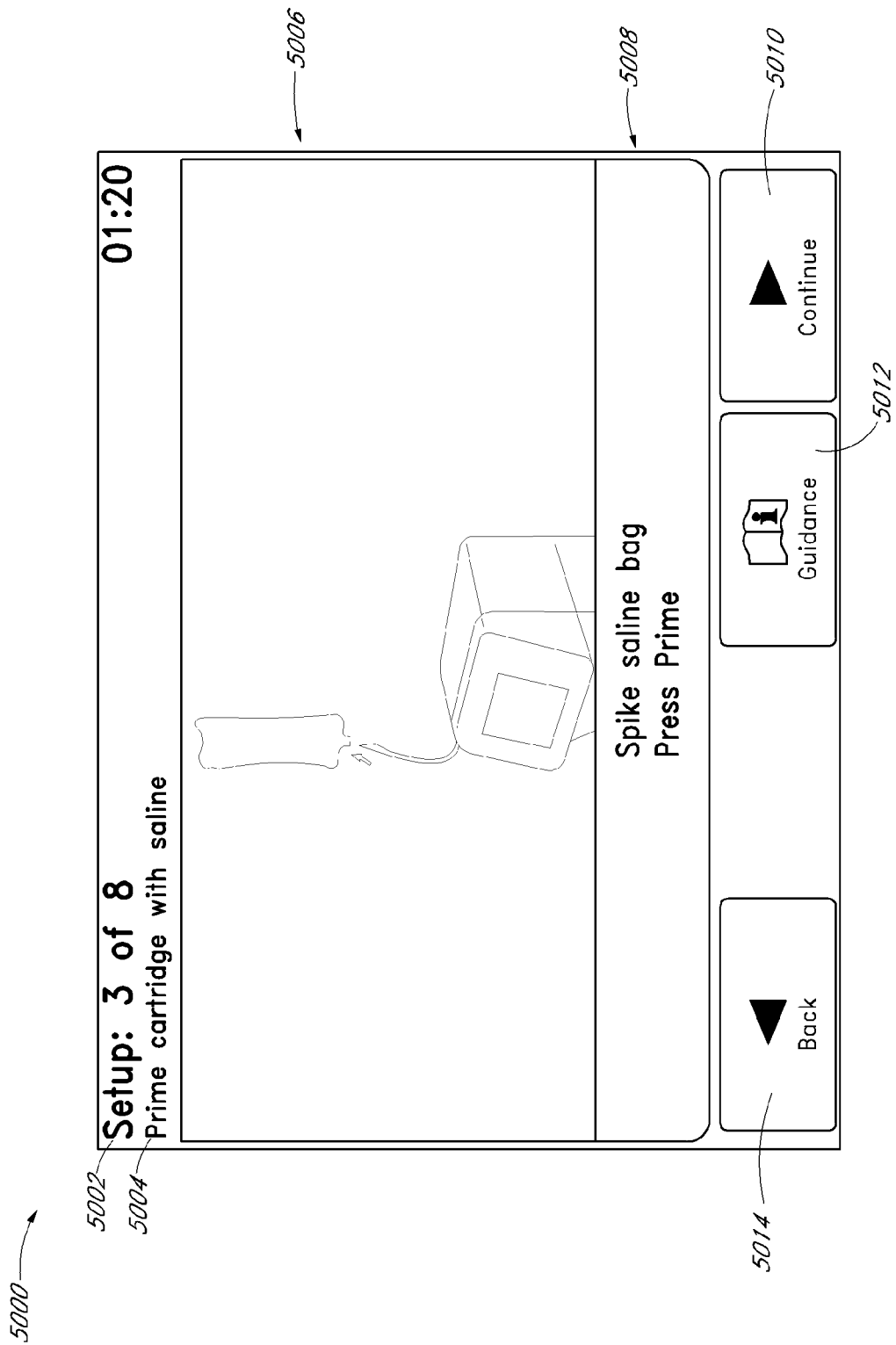
FIG. 50 schematically illustrates the visual appearance of the display of an embodiment of an automated setup instruction system.

FIG. 50 schematically illustrates the visual appearance of the display 5000 of an embodiment of the automated setup instruction system used with a medical device, e.g., the monitoring device 102. In this example embodiment, the automated setup instruction system prompts a user to prime a removable portion of the device with saline. The display 5000 indicates progress information 5002, or "Setup: 3 of 8" as shown in FIG. 50. A step description 5004 is displayed as "Prime cartridge with saline" in FIG. 50. A graphical display portion 5006 of the display 5000 visually depicts various sub-steps to be performed. A user of the device can rely on the depictions in the graphical display portion 5006 to accomplish the current step, and can also refer to text prompts shown in a textual display portion 5008 of the display 5000. In FIG. 50, the text prompts include "Spike saline bag" and "Press Prime." The user can actuate touch-screen buttons at the bottom of the display 5000, which can include a "back" button 5014 which can cause the display to return to previous steps performed, a help button 5012 which can display additional information about the current steps being performed or provide access to a searchable user guide stored on the device, and a "continue" button 5010 which can be actuated by a user when the steps have been completed to indicate to the automatic setup instruction system that the next step should be displayed.

Figure 51:
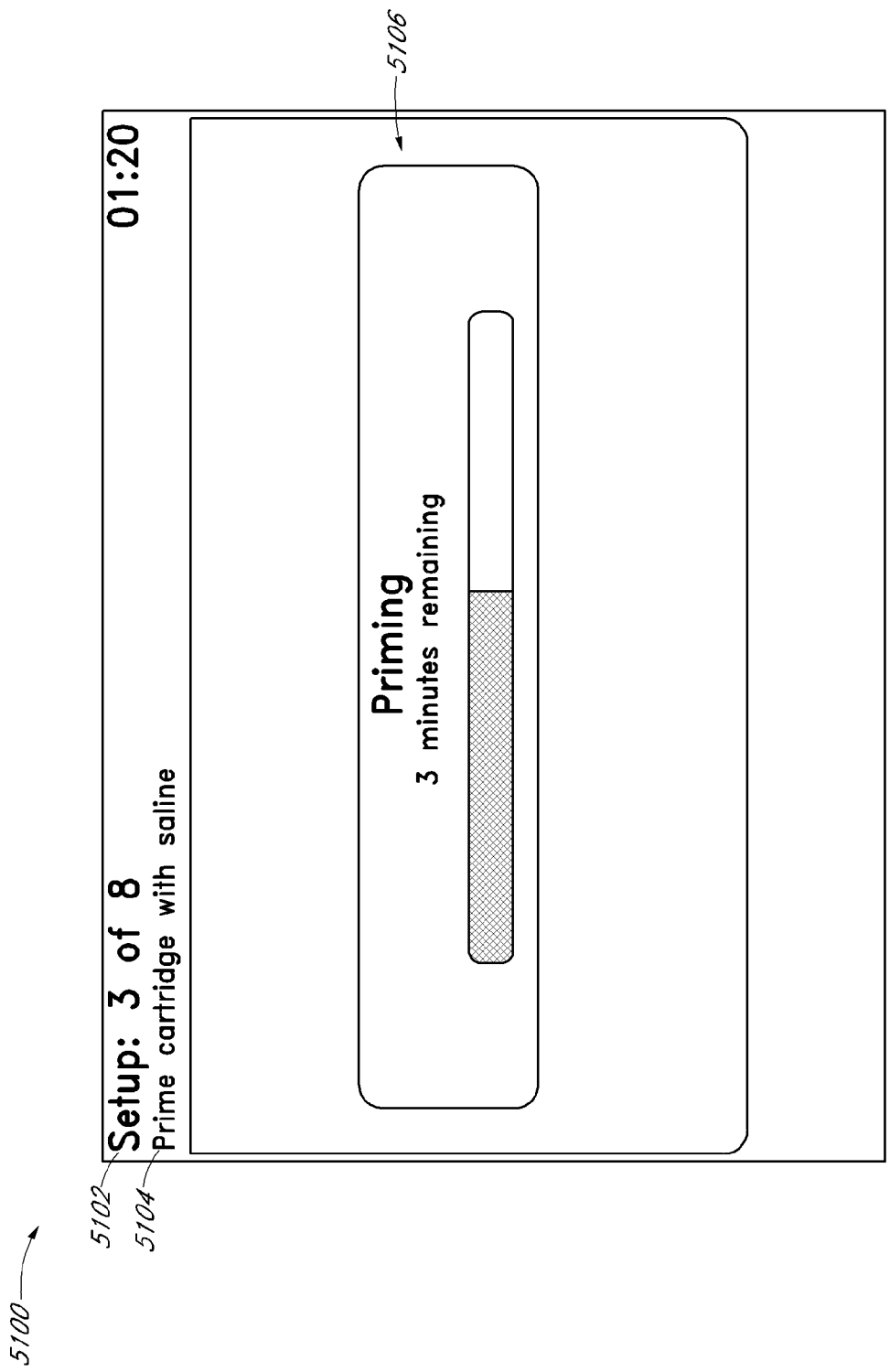
FIG. 51 schematically illustrates the visual appearance of the display of an embodiment of an automated setup instruction system.

FIG. 51 schematically illustrates the visual appearance of the display 5100 of an embodiment of the automated setup instruction system used with a medical device, e.g., the monitoring device 102. In this example embodiment, the automated setup instruction system indicates progress in automatically priming the cartridge with saline. The display 5100 indicates progress information 5102, or "Setup: 3 of 8" as shown in FIG. 51. A step description 5104 is displayed as "Prime cartridge with saline" in FIG. 51. Once the user has followed the instruction to press the "Prime" button as in FIG. 50, the medical device can automatically prime the cartridge with saline. A progress display portion 5106 can indicate to the user that the device is busy priming the cartridge, and can also display the estimated time remaining to perform this step. The background of the progress display portion 5106 can include a faded depiction of the figure displayed in the graphical display portion 5006 in FIG. 50, to indicate that the progress is related to that step and that the device is busy and not actively instructing the user to perform any steps.

Figure 52:
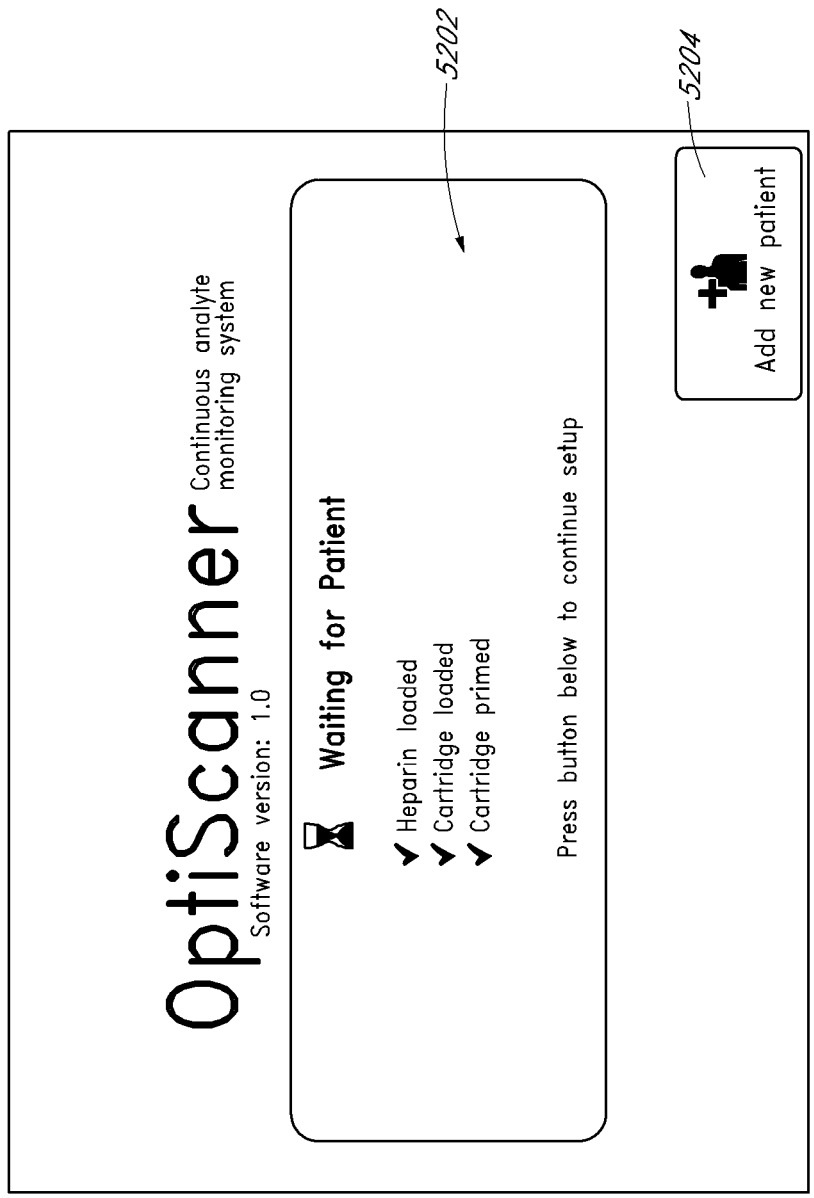
FIG. 52 schematically illustrates the visual appearance of the display of an embodiment of an automated setup instruction system.

FIG. 52 schematically illustrates the visual appearance of the display 5200 of an embodiment of the automated setup instruction system used with a medical device, e.g., the monitoring device 102. In this example embodiment, the automated setup instruction system indicates to a user that a patient can now be added to the monitoring device. The display 5200 displays status information 5202, which can include a list of setup steps that have already been performed and text indicating that the device is "waiting" for a patient before proceeding to finalize setup. An "Add new patient" button 5204 can be displayed, which can be an actuatable touch-screen button which prompts the automated setup instruction system to proceed to the next step when actuated.

Figure 53:
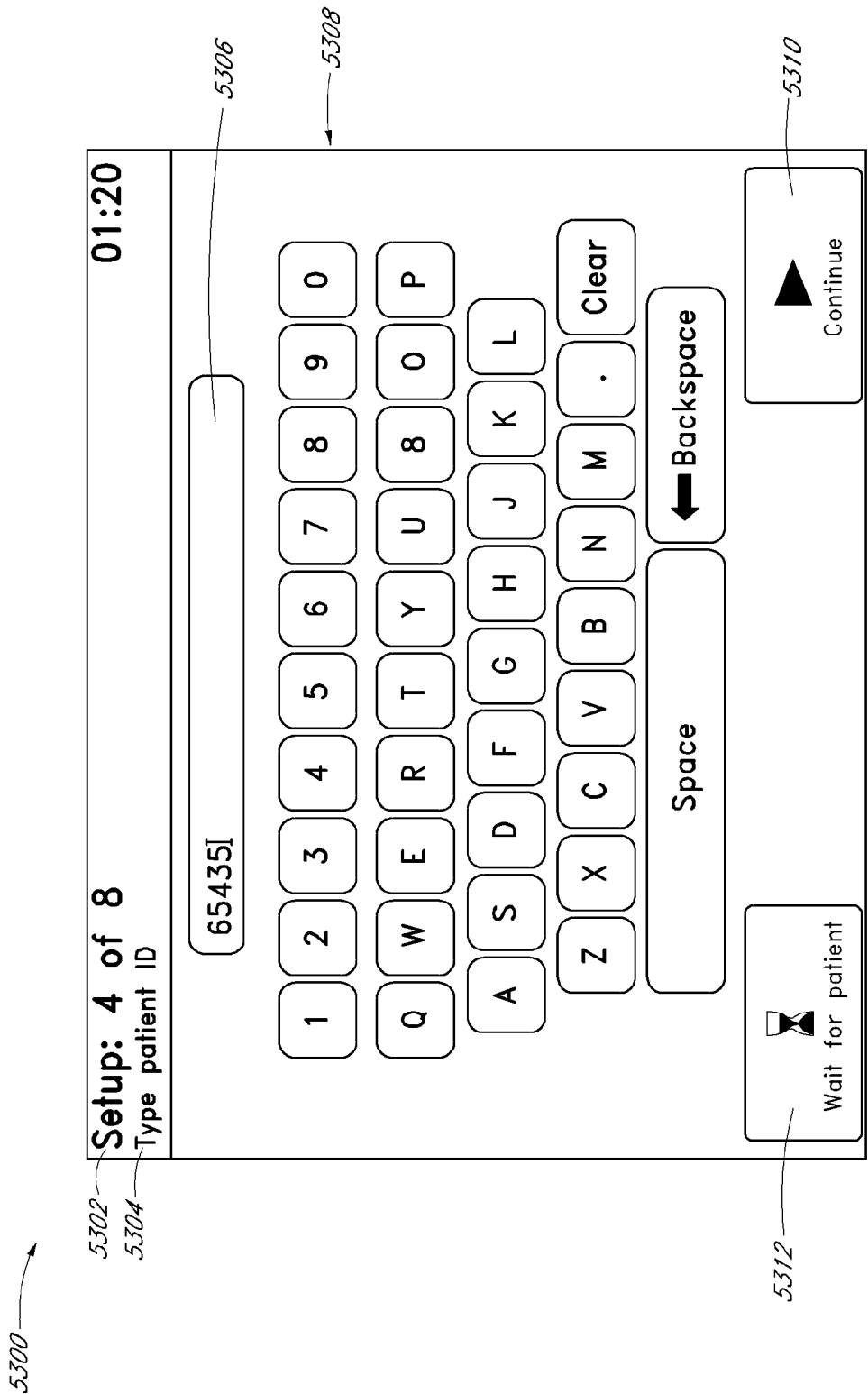
FIG. 53 schematically illustrates the visual appearance of the display of an embodiment of an automated setup instruction system.

FIG. 53 schematically illustrates the visual appearance of the display 5300 of an embodiment of the automated setup instruction system used with a medical device, e.g., the monitoring device 102. In this example embodiment, the automated setup instruction system prompts a user to enter a patient identification code, which may be a code assigned to a patient by a hospital to track medical services rendered or associate the patient with additional data stored by the hospital. The display 5300 indicates progress information 5302, or "Setup: 4 of 8" as shown in FIG. 53. A step description 5304 is displayed as "Type patient ID," which in FIG. 53 instructs a user of the device to type the identification code of the patient to be monitored by the device. A text window 5306 of the display 5300 displays text typed by the user. A user of the device can type the patient ID using a touch-screen keyboard 5308. A "Wait for patient" button 5312 can be included on the display 5300, and can be an actuatable touch-screen button which returns the device to the state displayed in FIG. 52 to indicate to a user that the device is ready for a patient to be connected to be monitored. Once the patient ID has been entered, a user can actuate a "continue" button 5310 to proceed to the next setup step. In some embodiments, a user can be prompted to scan a wristband of a patient to determine or confirm the patient identification code.

Figure 54:
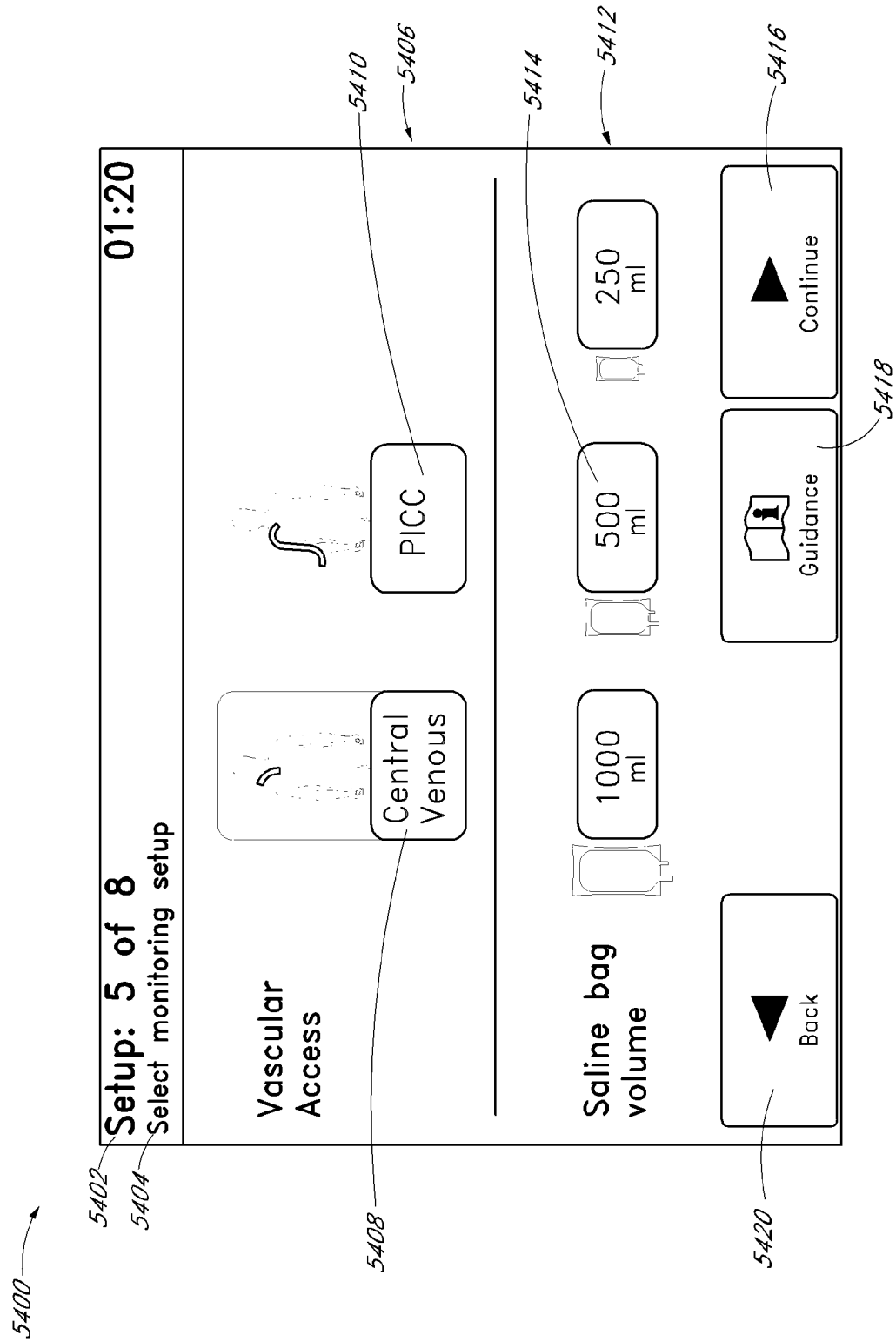
FIG. 54 schematically illustrates the visual appearance of the display of an embodiment of an automated setup instruction system.

FIG. 54 schematically illustrates the visual appearance of the display 5400 of an embodiment of the automated setup instruction system used with a medical device, e.g., the monitoring device 102. In this example embodiment, the automated setup instruction system prompts a user to select a monitoring setup. The display 5400 indicates progress information 5402, or "Setup: 5 of 8" as shown in FIG. 54. A step description 5404 is displayed as "Select monitoring setup" in FIG. 54. In a vascular access selection portion 5406, a user can select a vascular access mode that will be used to connect the patient to the monitoring device. In the display 5400 of FIG. 54, a user can actuate either a "Central Venous" button 5408 or a "PICC" button 5410, which can indicate whether a central catheter or peripherally inserted central catheter will be used to draw blood from the patient. Graphics associated with each of the buttons 5408, 5410 can supplement the textual description of the vascular access mode to aid a user in quickly choosing between the different options. In FIG. 54, for example, a graphic associated with a "Central Venous" button 5408 can show a short tubular object representing a catheter entering a patient's body near the chest. A graphic associated with a "PICC" button 5410 can show a long tubular object representing a catheter entering a patient's body in the arm and traveling to the patient's chest area. If in the display 5400 as shown in FIG. 54, the "Central Venous" button 5408 has been actuated, this can be indicated by a change in color of the button or other graphics depicting a depressed button on a touchscreen. In a saline bag volume selection area 5412 of the display 5400, a user is prompted to select from a number of options of saline bag volumes, which can be 1000 ml, 500 ml, and 250 ml, each with a corresponding touchscreen button and graphic showing a relatively large, medium, and small-sized saline bag. A user could press on a touchscreen, for example, the 500 ml button 5414 as shown in FIG. 54. The monitoring device 102 can use the information selected in this setup phase to set additional settings of the device. A user can actuate a "back" button 5420 to revert back to the previous instruction screen, a "guidance" button 5418 to access a searchable on-screen user guide or additional information about this setup step, or a "continue" button 5416 to proceed to the next step.

Figure 55:
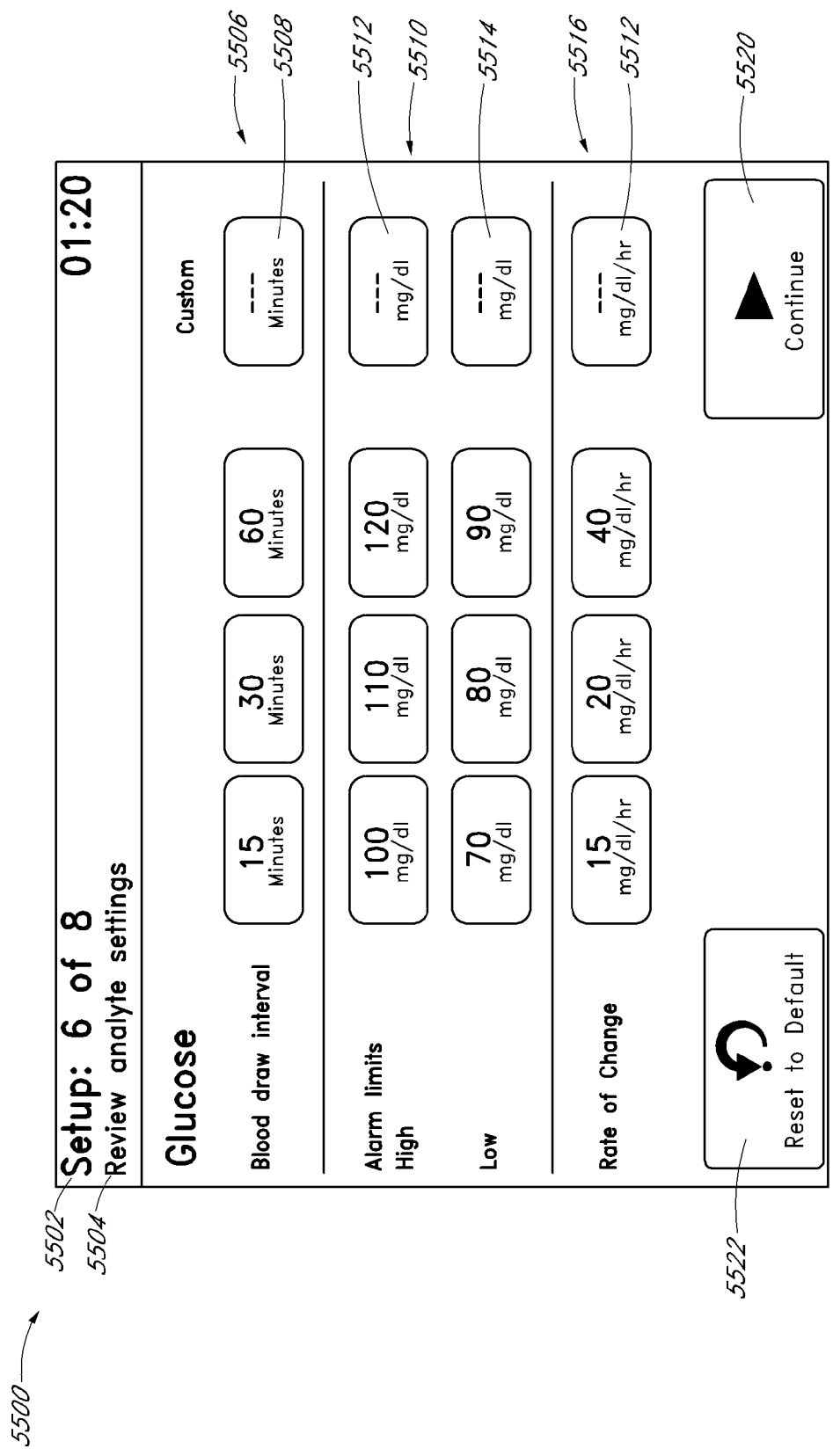
FIG. 55 schematically illustrates the visual appearance of the display of an embodiment of an automated setup instruction system.

FIG. 55 schematically illustrates the visual appearance of the display 5500 of an embodiment of the automated setup instruction system used with a medical device, e.g., the monitoring device 102. In this example embodiment, the automated setup instruction system prompts a user to review and/or select analyte monitoring settings. The display 5500 indicates setup progress information 5502, or "Setup: 6 of 8" as shown in FIG. 55. A step description 5504 is displayed as "Review analyte settings" in FIG. 55, which indicates to a user of the device to select settings that will determine how the device operates to monitor analytes of a patient. The display 5500 indicates that glucose is the analyte to be monitored. In a blood draw interval selection portion 5506 of the display 5500, a user can view options for time intervals between blood draws by the monitoring device 102. Each option, for example 15 minutes, 30 minutes, or 60 minutes as shown in FIG. 55, can be selected by actuating a touchscreen button labeled with the desired time interval. Alternatively, a user can actuate a custom interval button 5508 to specify a time interval different from the discrete options automatically displayed. When the custom interval button 5508 is actuated, a pop-up dialog with a number keypad can be displayed on the display 5500 to allow a user to enter a desired blood draw interval. Similarly, a user can select high and low alarm limits in an alarm limit selection area 5510. Again, a user can choose between discrete options that can be generated by the automated setup instruction system, or custom limits by actuating a custom high alarm limit button 5512 and/or custom low alarm limit button 5514. As with the custom interval button 5508, a pop-up dialog with numeric keypad can be displayed to enable the user to specify a custom value. As with other options selected during setup, the automated setup instruction system can communicate these settings to other systems in the monitoring device to alter the way in which analyte monitoring is performed. By selecting a high alarm limit of 110 mg/dL, for example, a user can expect an alarm of the monitoring device 102 to sound or display when measured or estimated glucose concentration exceeds this value. In a rate of change selection area 5516 of the display 5500, a user can select from displayed values of glucose rate of change or actuate the custom rate of change button 5518 to set a custom value. A "back" button 5522 can be actuated to return to the previous screen of the display or previous instruction step. A "continue" button 5520 can provide an input to the automated setup instruction system to continue to the next set of setup instructions.

Figure 56:
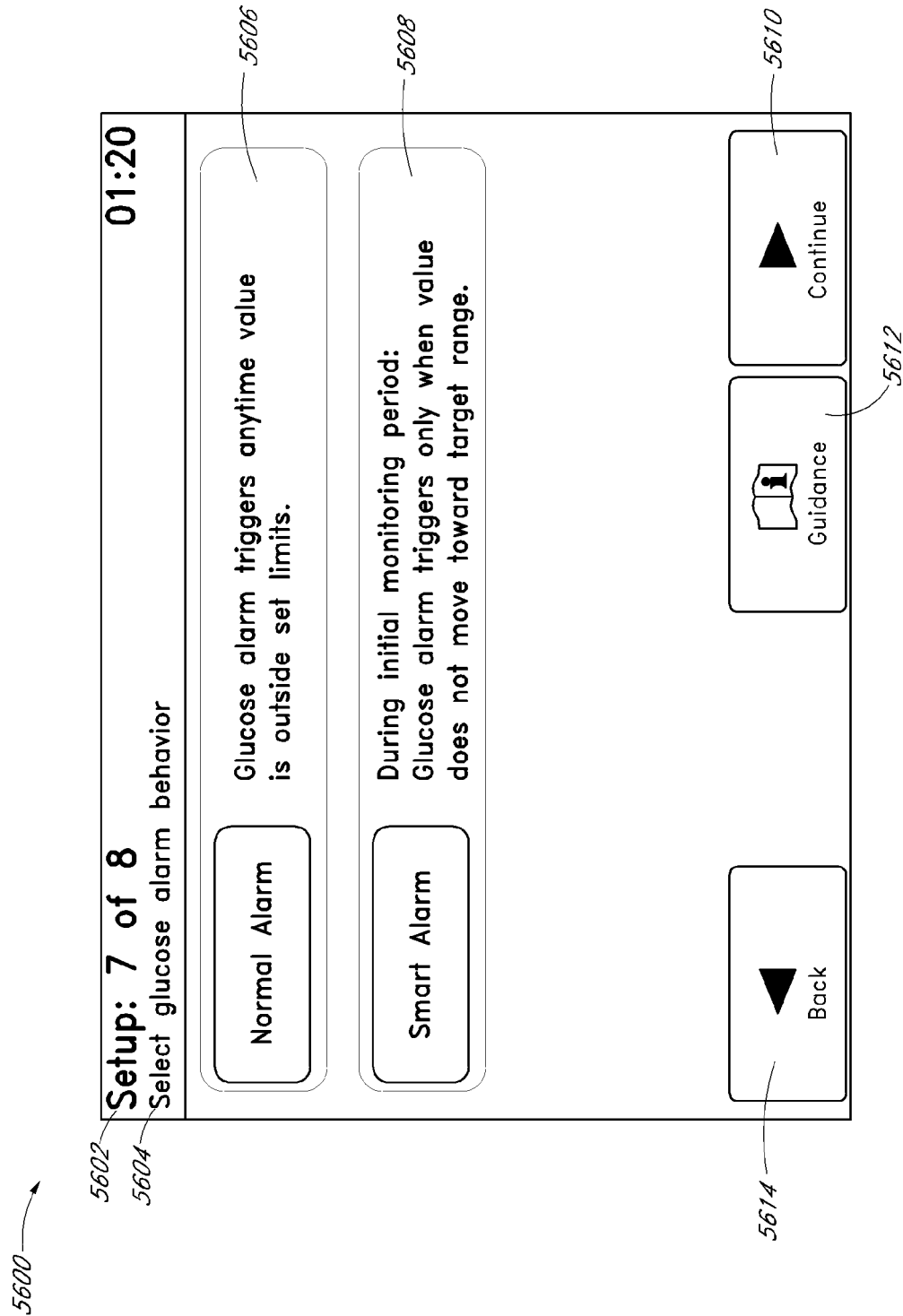
FIG. 56 schematically illustrates the visual appearance of the display of an embodiment of an automated setup instruction system.

FIG. 56 schematically illustrates the visual appearance of the display 5600 of an embodiment of the automated setup instruction system used with a medical device, e.g., the monitoring device 102. In this example embodiment, the automated setup instruction system prompts a user to select glucose alarm behavior. The display 5600 indicates setup progress information 5602, or "Setup: 7 of 8" as shown in FIG. 56. A step description 5604 is displayed as "Select glucose alarm behavior" in FIG. 56, which indicates to a user of the device to select from among different types of behavior of an alarm that can be automatically triggered by certain measured glucose levels. A normal alarm section 5606 of the display 5600 can include a brief description of the "normal" alarm along with an actuatable button to select this alarm behavior. For example, as shown in FIG. 56, the "normal" alarm behavior is described as follows: "Glucose alarm triggers anytime value is outside set limits." A smart alarm section 5608 of the display 5600 can include a brief description of a "smart" alarm along with an actuatable button to select this alarm behavior. For example, as shown in FIG. 56, the "smart" alarm behavior is described as follows: "During initial monitoring period: Glucose alarm triggers only when value does not move toward target range. A user can actuate a "back" button 5614 to revert back to the previous instruction screen, a "guidance" button 5612 to access a searchable on-screen user guide or additional information about this setup step, or a "continue" button 5610 to proceed to the next step.

Figure 57:
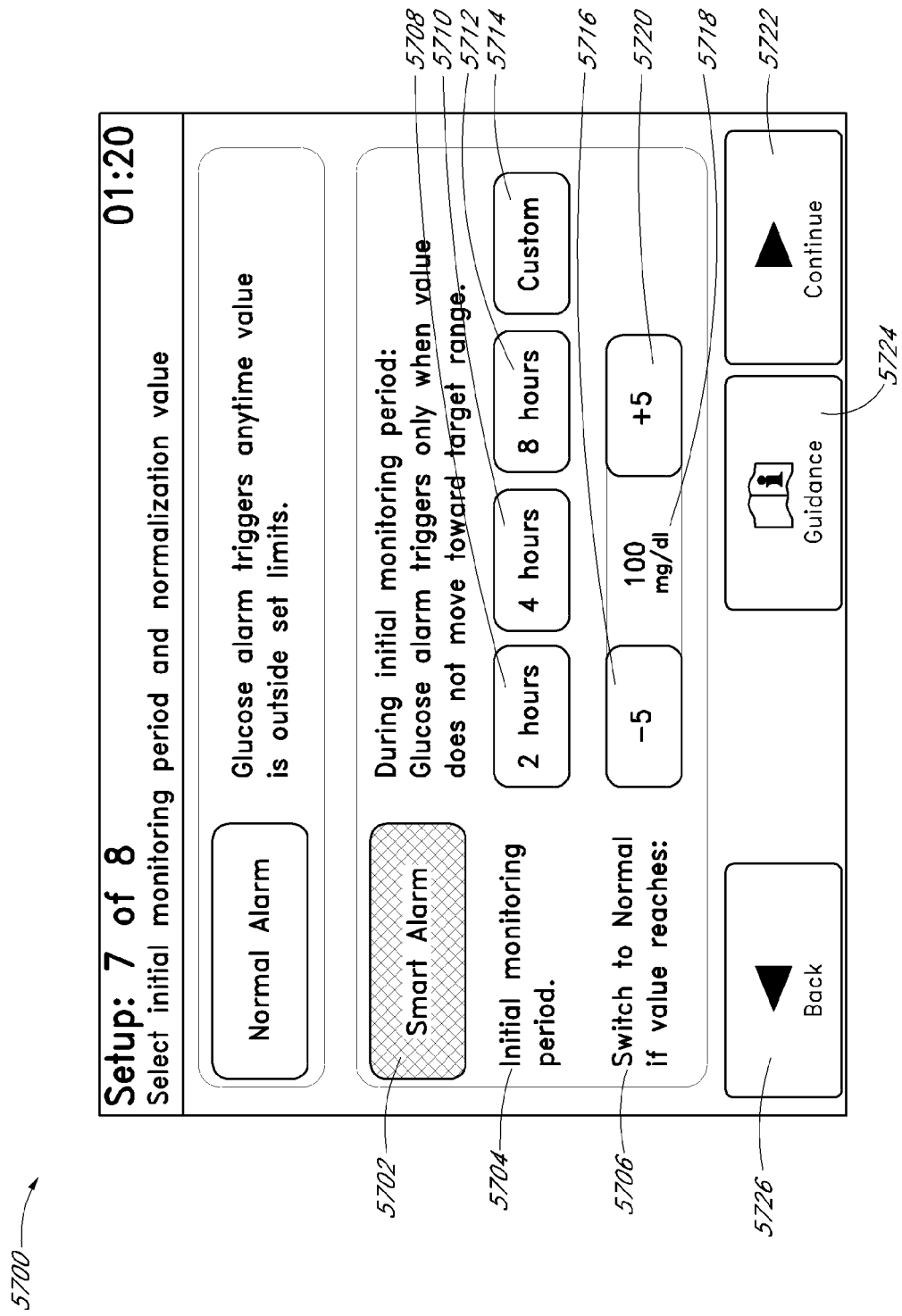
FIG. 57 schematically illustrates the visual appearance of the display of an embodiment of an automated setup instruction system.

FIG. 57 schematically illustrates the visual appearance of the display 5700 of an embodiment of the automated setup instruction system used with a medical device, e.g., the monitoring device 102. In this example embodiment, the automated setup instruction system prompts a user to select additional preferences relating to the smart alarm discussed with reference to FIG. 56. In FIG. 57, the smart alarm button 5702 has been actuated, as indicated by the shading of the button 5702. An initial monitoring period selection prompt 5704 indicates to a user that one of the touchscreen buttons, e.g., 2 hour button 5708, 4 hour button 5710, 8 hour button 5712, or custom monitoring period button 5714 in FIG. 57, can be actuated to select an initial monitoring period in which the smart alarm will only trigger when the measured glucose values of a patient do not move toward a specified target range. A switch prompt 5706 can also be included on display 5700 to allow a user to specify a glucose value that, if reached, will switch the alarm behavior from "smart" to "normal." As shown in FIG. 57, the switch prompt can include the following text: "Switch to Normal If value reaches:". Next to the switch prompt can be a "−5" button 5716, a switch value display 5718, and a "+5" button 5720 which can be selectively actuated to specify the alarm switch value. For example, if the current switch value display 5718 shows 100 mg/dL as shown in FIG. 57, the "−5" button 5716 can be actuated once to change the switch value to 95 mg/dL or the "+5" button can be actuated once to change the switch value to 105 mg/dL. As with other screens, a user can actuate a "back" button 5726 to revert back to the previous instruction screen, a "guidance" button 5724 to access a searchable on-screen user guide or additional information about this setup step, or a "continue" button 5722 to proceed to the next step.

Figure 58:
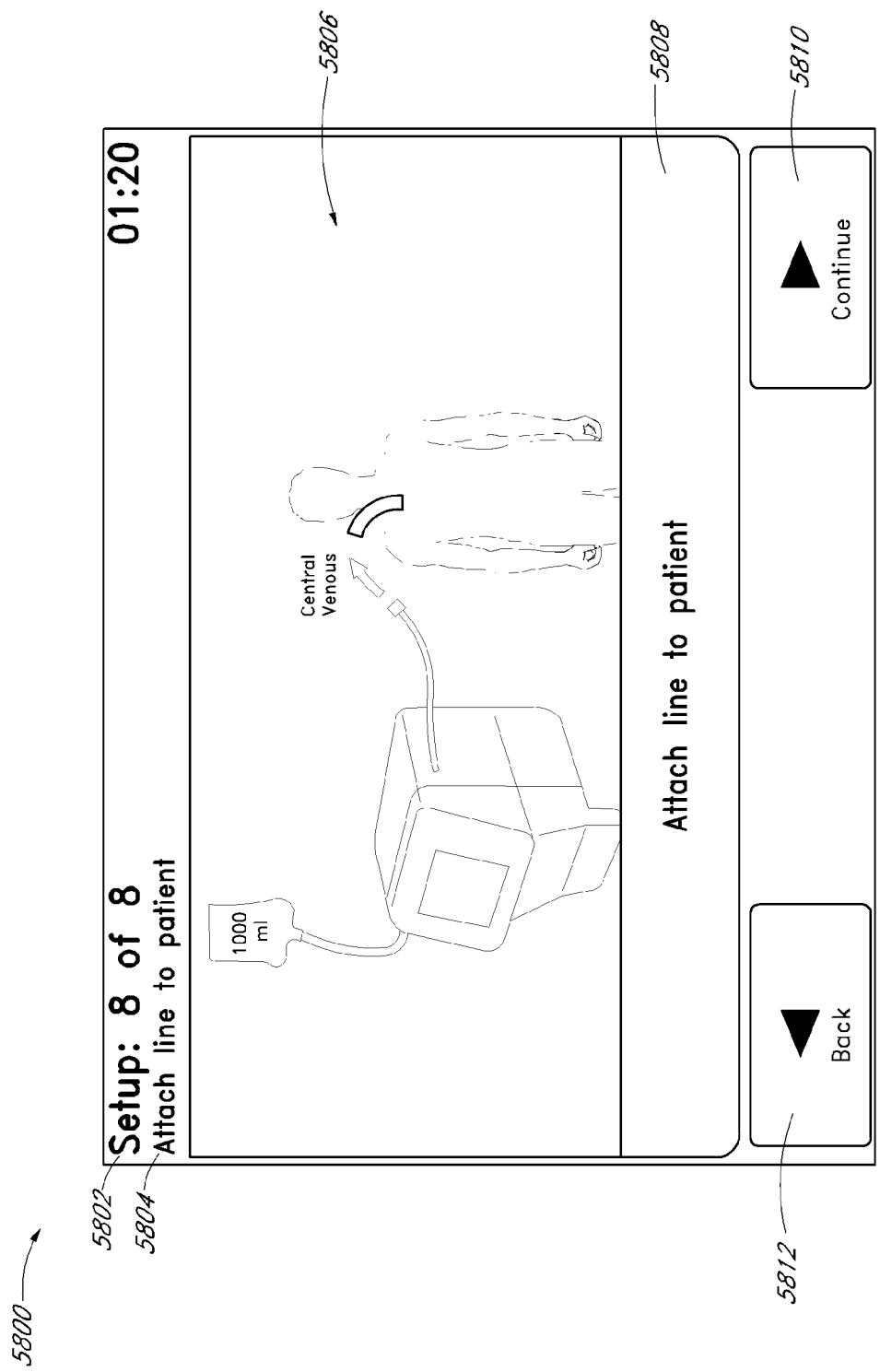
FIG. 58 schematically illustrates the visual appearance of the display of an embodiment of an automated setup instruction system.

FIG. 58 schematically illustrates the visual appearance of the display 5800 of an embodiment of the automated setup instruction system used with a medical device, e.g., the monitoring device 102. In this example embodiment, the automated setup instruction system prompts a user to attach a tubing line to a patient. The display 5800 indicates setup progress information 5802, or "Setup: 8 of 8" as shown in FIG. 58. A step description 5804 is displayed as "Attach line to patient" in FIG. 58. A graphical display portion 5806 of the display 5800 visually depicts the current step to be performed. In FIG. 58, the monitoring device is displayed near a patient with a tube running from the device to the patient's chest area, along with the text "Central venous" as a reminder that the central venous vascular access mode was selected. A user of the device can rely on the depictions in the graphical display portion 5806 to accomplish the current step, and can also refer to text prompts shown in a textual display portion 5808 of the display 5800. In FIG. 58, the text prompt is the same as the step description 5804: "Attach line to patient." A user can actuate a "back" button 5812 to revert back to the previous instruction screen or a "continue" button 5810 to complete setup and prepare for monitoring.

Figure 59:
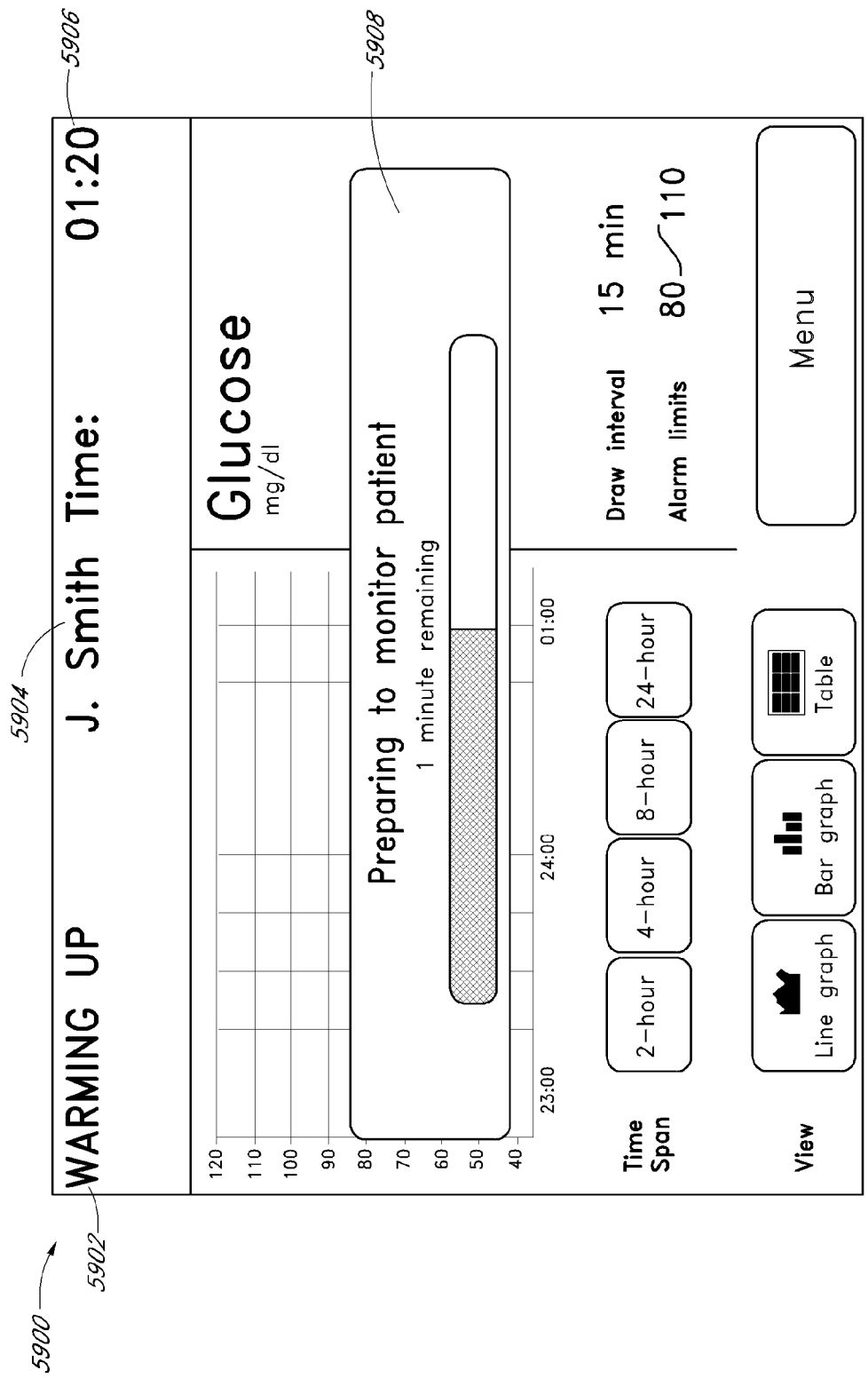
FIG. 59 schematically illustrates the visual appearance of the display of an embodiment of an automated setup instruction system.

FIG. 59 schematically illustrates the visual appearance of the display 5900 of an embodiment of the automated setup instruction system used with a medical device, e.g., the monitoring device 102. In this example embodiment, the automated setup instruction system alerts a user that the device is preparing to monitor a patient. A status description 5902 can be displayed to indicate that the device is "warming up." The patient's name 5904 can also be displayed as shown in FIG. 59, if desired. The current time 5906 can be displayed. The display 5900 can also include a progress window 5908, which can be a pop-up dialog. The progress window 5908 can have text indicating that the device is "busy" performing a certain task, e.g., "preparing to monitor patient" in FIG. 59, an estimated time for completing the task, e.g., "1 minute remaining," and a visual depiction of the progress, e.g., an area that is progressively shaded in as the task progresses, e.g., as shown in FIG. 59. In the background of the progress window 5908 can be display information normally displayed while the device is monitoring a patient. The background can be greyed out or faded to further indicate the device is not yet monitoring but preparing to monitor. The indication that the device is "busy" alerts the user that no additional input to the automated setup instruction system is currently required, while allowing the device to assimilate any settings selected during the setup process and perform any initialization of hardware or software needed to begin monitoring a patient. When the preparation is complete, the progress window 5908 can disappear, and the device can begin monitoring a patient, displaying information to a user, and performing other functions described herein.

As used herein, the term "anti-coagulant" is a broad term, and is used herein to refer to any fluid introduced into a medical system. Anti-coagulants can be heparin in any of its chemical forms or derivatives, or any other chemical having a tendency to reduce blood clotting or coagulation of organic fluids.

Reference throughout this specification to "some embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

Embodiments of the disclosed systems and methods may be used and/or implemented with local and/or remote devices, components, and/or modules. The term "remote" may include devices, components, and/or modules not stored locally, for example, not accessible via a local bus. Thus, a remote device may include a device which is physically located in the same room and connected via a device such as a switch or a local area network. In other situations, a remote device may also be located in a separate geographic area, such as, for example, in a different location, building, city, country, and so forth.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may be comprised of connected logic units, such as gates and flip-flops, and/or may be comprised of programmable units, such as programmable gate arrays, application specific integrated circuits, and/or processors. The modules described herein are preferably implemented as software modules, but may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with patients, health care practitioners, administrators, other systems, components, programs, and so forth.

A number of applications, publications, and external documents may be incorporated by reference herein. Any conflict or contradiction between a statement in the body text of this specification and a statement in any of the incorporated documents is to be resolved in favor of the statement in the body text.

Although described in the illustrative context of certain preferred embodiments and examples, it will be understood by those skilled in the art that the disclosure extends beyond the specifically described embodiments to other alternative embodiments and/or uses and obvious modifications and equivalents. Thus, it is intended that the scope of the claims which follow should not be limited by the particular embodiments described above.

What is claimed is:

1. A medical device and automated setup instruction system comprising:
   a fluid system comprising:
      a non-disposable subsystem including at least one of a valve, a sensor or a pump;
      a first disposable subsystem including at least one of a tube, a fitting or a waste bladder; and
      a second disposable subsystem including a disposable cartridge configured to hold and prepare a sample of bodily fluid for analysis;
   a display configured to be visible to a medical device user when the user is preparing the medical device for use in a medical setting;

a computer memory configured to store setup information and protocols that are specific to the medical device;

an input module configured to receive input relating to device setup, the input module comprising:

one or more sensors configured to detect configuration of components of the medical device and/or data regarding the environment in which the device is used;

one or more direct user input portions configured to accept input from the user relating to user-participation aspects of the device setup protocols; and an automatic in-service medical device setup controller configured to access the computer memory according to the stored protocols and provide, on the display, sequential instructions to the medical device user to setup and/or use the device, wherein the setup controller determines based on input received from the input module to display a portion of the setup information stored on the computer memory, wherein the automatic in-service medical device setup controller is configured to provide instructions directed towards at least one of: attaching the medical device to a source of bodily fluid, loading the second disposable subsystem into the medical device, priming the second disposable subsystem with saline, selecting medical device settings determining operating conditions of the medical device or selecting different alarm settings.

2. The system of claim 1, wherein the setup controller is configured to provide the sequential instructions to the user in real-time.

3. The system of claim 1, wherein the setup controller is configured to provide setup instructions sequentially to the user.

4. The system of claim 1, wherein the setup controller is configured to provide setup instructions to the user by displaying text and/or graphics on the display.

5. The system of claim 1, wherein the user input comprises an answer to a query displayed to the user on the display or a command to continue to provide the next set of instructions on the display.

6. The system of claim 1, wherein the user input comprises a password, a code or a security information.

7. The system of claim 1, wherein the setup controller is configured to prompt the user to take one or more actions based on the input received from the input module related to the status of the medical device.

8. The system of claim 7, wherein the setup controller is configured to provide audio or visual prompts.

9. The system of claim 1, wherein the setup controller is configured to display a status of the medical device based on the input received from the input module.

10. The system of claim 1, further comprising an analyte monitoring system configured to determine concentration of an analyte in the sample of bodily fluid, wherein the analyte is glucose.

11. The system of claim 10, wherein the setup controller is configured to provide a signal to the analyte monitoring system to begin monitoring a patient upon completion of the setup.

12. The system of claim 1, further comprising a fluid controller configured to:

withdraw bodily fluid from the source of bodily fluid using the fluid system;

obtain the sample of bodily fluid from the withdrawn bodily fluid using the non-disposable subsystem;

direct the sample of bodily fluid through the first disposable subsystem towards the second disposable subsystem; and direct the sample of bodily fluid from the second disposable subsystem towards an element of the first disposable system after analysis.

13. The system of claim 1, wherein the first disposable subsystem is fluidically connected to the second disposable subsystem.

* * * * *